United States Patent [19]
Jadvar et al.

[11] Patent Number: 5,010,888
[45] Date of Patent: Apr. 30, 1991

[54] METHOD AND APPARATUS FOR DETECTION OF POSTERIOR ISCHEMIA

[75] Inventors: Hossein Jadvar, Ann Arbor, Mich.; Robert C. Arzbaecher, Chicago, Ill.

[73] Assignee: Arzco Medical Electronics, Inc., Vernon Hills, Ill.

[21] Appl. No.: 267,459

[22] Filed: Nov. 4, 1988

Related U.S. Application Data

[63] Continuation-in-part of Ser. No. 173,367, Mar. 25, 1988.

[51] Int. Cl.[5] .......... A61B 5/04
[52] U.S. Cl. .......... 128/696; 128/419 PG; 128/787
[58] Field of Search .......... 128/695, 696, 697, 699, 128/700, 702, 703, 704, 705, 706, 707, 419 PG, 419 D, 787

[56] References Cited

U.S. PATENT DOCUMENTS

| | | | |
|---|---|---|---|
| 164,184 | 6/1875 | Kidder | 128/419 P |
| 1,056,336 | 3/1913 | Hurdman | 128/783 |
| 3,326,207 | 6/1967 | Egan | 128/698 |
| 3,339,542 | 9/1967 | Howell | 128/736 |
| 3,703,900 | 11/1972 | Holznagel | 128/419 P |
| 3,716,059 | 2/1973 | Welborn et al. | 128/419 D |
| 3,951,136 | 4/1976 | Wall | 128/DIG. 4 |
| 4,088,138 | 5/1978 | Diack et al. | 128/419 D |
| 4,090,518 | 5/1978 | Elam | 128/203.14 |
| 4,176,660 | 12/1979 | Mylrea et al. | 128/671 |
| 4,304,239 | 12/1981 | Perlin | 128/642 |
| 4,304,240 | 12/1981 | Perlin | 128/671 |
| 4,349,030 | 9/1982 | Belgard et al. | 128/419 PG |
| 4,351,330 | 9/1982 | Scarberry | 128/419 D |
| 4,432,375 | 2/1984 | Angel et al. | 128/705 |
| 4,467,813 | 8/1984 | Schomburg | 128/702 |
| 4,473,078 | 9/1984 | Angel | 128/419 D |
| 4,475,555 | 10/1984 | Linder | 128/670 |
| 4,476,872 | 10/1984 | Perlin | 128/642 |
| 4,517,984 | 5/1985 | Perlin | 128/642 |
| 4,574,807 | 3/1986 | Hewson et al. | 128/419 PG |
| 4,640,298 | 2/1987 | Pless et al. | 128/419 D |
| 4,683,890 | 8/1987 | Hewson | 128/419 PG |
| 4,706,688 | 11/1987 | Michael et al. | 128/419 D |
| 4,729,384 | 3/1988 | Bazenet | 128/691 |
| 4,735,206 | 4/1988 | Hewson | 128/419 D |

OTHER PUBLICATIONS

CRC (Cardiac Resuscitator Corp.), "The Heart Savers", PACE AID 52.
R. Arzbaecher, A Pill Electrode for the Study of Cardiac Arrhythmia, 9-10/1978.
PACE, vol. 8, Use of the Pill Electrode for Transesophageal Atrial Pacing, 7-8, 1985, Janice M. Jenkins, MacDonald Dick, Steve Collins, Wm. O'Neill, R. M. Campbell, D. J. Wilber.
R. D. Fletcher, M.D., R. C. Saunders, M.D.; The Heart; Arzco Medical Electronics, Inc.
FIG. 2 Prior Art.
FIG. 3 Prior Art.
E. M. Kavan, M.D., R. R. Colvin, M.D.; Clinical Use of Esophageal ECG Electrod During Surgery; Anethesia and Analgesia, vol. 44, No. 1, Jan.-Feb. 1986.
IEEE Transactions on Biomedical Engineering, vol. BME-25, No. 4, Jul. 1978, pp. 377-380.
TELECOR, Medtronic, Inc.; Now . . . a Convenient Yet Simple Method for Monitoring Heart Sounds, Cardiac Rate, and Care Temperature.
Esophageal Monitoring Probes: Diagnostic Instrument Corporation.
H. R. Andersen, P. Pless; Trans-Esophageal Pacing; PACE, vol. 6, Jul.-Aug. 1983, pp. 674-679.
(List continued on next page.)

*Primary Examiner*—Francis Jaworski
*Assistant Examiner*—George Manuel
*Attorney, Agent, or Firm*—Dressler, Goldsmith, Shore, Sutker & Milnamow, Ltd.

[57] ABSTRACT

An apparatus for automatically detecting a posterior ischemia includes a multi-element esophageal electrode coupled to an artifact suppressing circuit and a cardiac stimulator. Output from the artifact suppressing circuit, the detected QRS wave, is processed in analog and digital filters. The processed signal is analyzed to automatically determine the presence or absence of the posterior ischemia.

42 Claims, 12 Drawing Sheets

OTHER PUBLICATIONS

H. R. Andersen, P. Pless; Trans-Oesophageal Dual--Chamber Pacing: International Journal of Cardiology, pp. 745-748; 1984.

Cardiac Pacing; Excerpta Medica; Experience with an Electrical Conductive Rubber Electrode for Esophageal Pacing in Infants, H. Meisner, S. Paek, R. Schober, W. Heimisch, pp. 493-498.

Mitsui et al., An Esophageal Balloon Electrode for Cardiac Pacing; pp. 282-287.

Sabino Iliceto, M.D., et al.; Detection of Coronary Artery Disease by Two-Dimensional Echocardiography and Transesophageal Atrial Pacing; JACC vol. 5, No. 5, May 1985, pp. 1185-1197.

James G. M. Hamilton, et al.; The Ventricular Deflections in Myocardial Infraction; The American Heart Journal, pp. 414-424.

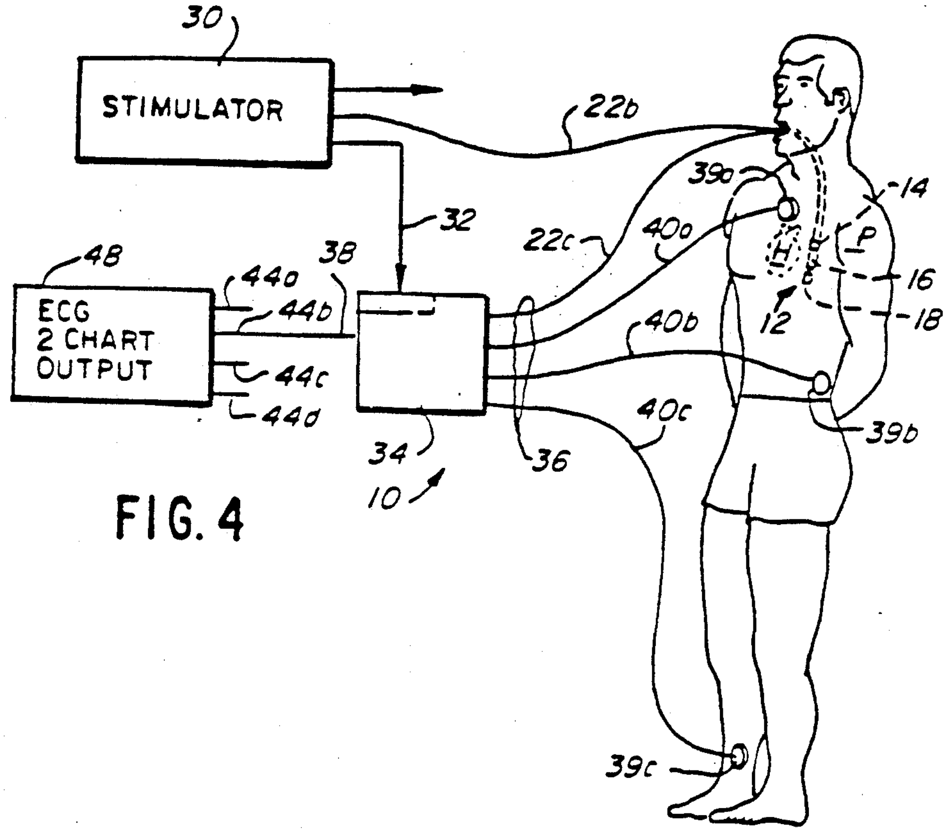
FIG. 4
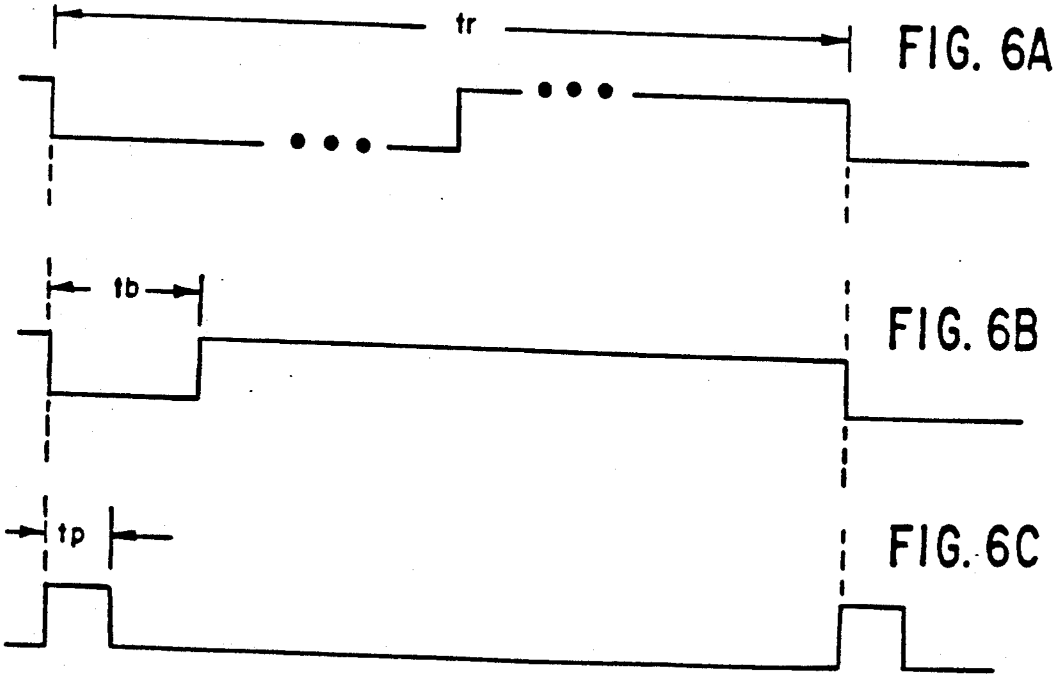
FIG. 6A
FIG. 6B
FIG. 6C

METHOD AND APPARATUS FOR DETECTION OF POSTERIOR ISCHEMIA

CROSS-REFERENCE TO RELATED APPLICATION

This application is a continuation-in-part of copending application U.S. Ser. No. 173,367 filed on Mar. 25, 1988.

FIELD OF THE INVENTION

The invention pertains to an apparatus and a method of non-invasively detecting a selected heart condition. More particularly, the invention pertains to stressing the heart with transesophageal heart pacing, sensing selected heart generated electrical signals and analyzing the sensed signals.

BACKGROUND OF THE INVENTION

Cardiovascular disease is a very serious threat to life and health in the U.S. It accounts for one-half of all deaths in the U.S.

Coronary artery disease is recognized as the leading cause of heart disease. It is the principle cause of death after age of 40 in men and after age of 50 in women.

Coronary artery disease kills and disables people in their most productive years. It accounts for $8.6 billion spent in 1981 for medical care. Coronary artery disease causes about 800,000 new heart attacks each year and an additional 450,000 recurrences.

It is estimated that a 30-year old American male would survive to age 79 rather than 73 if coronary artery disease could be eliminated. In 1982, there were 640,000 coronary deaths in the U.S. In the age range 35 to 64 about 75% of all cardiac deaths are due to coronary artery disease. Sudden, unexpected, out of hospital coronary deaths that occur too rapidly to allow arrival at the hospital while the patient is still alive account for more than one-half of all coronary fatalities.

Examination of the incidence, prevalence, mortality, and history of coronary artery disease suggests the need for a preventive approach. Correction of predisposing factors and innovative advances in diagnosis and therapy can make a major impact at least in reduction of coronary artery disease. This is essential since when a region of the myocardium, the heart muscle, is irreversibly damaged no current therapy can be expected to restore full heart function.

Early detection of coronary artery disease is important in reducing the extent of myocardial injury. Modern techniques of cardiology such as coronary angiography, thallium perfusion imaging, echocardiography, and radionuclide ventriculography permit highly sensitive and specific tests of myocardial ischemia (reduced blood supply to myocardial tissue), myocardial infarction (complete lack of blood supply causing death of myocardial tissue), and wall motion abnormalities secondary to coronary artery disease.

Unfortunately, the above noted methods are either invasive or expensive. As a result, ordinary electrocardiography and analysis of the resulting electrocardiograph (ECG) remains a very widely used, noninvasive tool in preliminary diagnosis of myocardial ischemia. Evidence of coronary artery disease is frequently identified by changes in the configuration of a certain portion of the ECG signal designated as the ST-segment. These changes manifest themselves clearly when the heart is under stress. The sensitivity and specificity of the ECG in detection of coronary artery disease can be increased by simultaneously stressing the heart.

There are several forms of stressing the heart which can be used to assess patients with chronic ischemic heart disease. These include dynamic exercise, isometric exercise, pharmacological stress, and atrial pacing.

For the past 50 years, the results of using exercise induced stress in combination with a simultaneously recorded ECG for both diagnostic and prognostic purposes have been the subject of intense research. However, not all patients are able to exercise. This can be due to obesity, poor physical condition, neuropathy, respiratory limitation, claudication, arthritis, paraplegia, lower limb amputation, diabetes, unstable angina, or risk of complication and physical incapacity in patients with recent myocardial infarction.

Cardiac stress induced by isometric exercise is often inadequate in provoking ischemic events. Pharmacological stress induced by intravenous drugs such as dipyridamole or dobutamine is commonly associated with cardiac or non-cardiac side effects, unknown pharmacokinetics for individual patients, and long delays in taking full effect. It is also ineffective in eliciting an adequate electrocardiographic response.

Transesophageal atrial pacing-induced stress in conjunction with two-dimensional echocardiography or radionuclide ventriculography has been reported to be a safe and accurate method in diagnosing ischemia. It is especially useful in patients who cannot perform an adequate exercise stress test. Iliceto S., Sorino M., D'Ambrosio G., et al. "Detection of Coronary Artery Disease By Two-Dimensional Echocardiography and Transesophage Atrial Pacing", *J. Am Coll. Cardiol,* 5(5):1188-97,1985.

ST elevation in esophageal ECG has also been shown by Kates R.A., Zaiden J.R., and Kaplan J.A. "Esophageal Lead For Intraoperative Electrocardiographic Monitoring", published in *Anesth. Analog.*, 61:781-5, 1982.

Transesophageal pacing offers the advantages of direct control over the heart rate and an increased control over the degree of myocardial stress which is noninvasive. Further, it does not depend on the physical condition of the patient, and is not subjected to the wide variability in heart rates and blood pressure responses commonly associated with dynamic exercise.

The esophageal route also provides a vantage point to detect posterior ischemia. The mortality rate associated with posterior abnormalities has been estimated at 15%. Electrocardiographic diagnosis of posterior abnormalities such as ischemia is often difficult or equivocal. This is because no surface lead records the electrical activity of the posterior cardiac wall directly.

Under the best of conditions, the posterior wall of the left ventricle is hidden from the chest electrodes by the anterior wall. Electrodes located on the back of the patient are not of much use because of their distance from the heart and because of the intervening high resistivity lungs.

In contrast to the body surface, the esophagus provides a vantage from which to view the posterior aspects of the heart at close range and without intervening active or resistive tissue. Studies have shown that the esophageal ECG recorded at the ventricular level is as specifically diagnostic of posterior myocardial abnormalities as the precordial ECG is diagnostic of anterior wall abnormalities. Hamilton J.G.M., Nyboer J., "The Ventricular Deflections in Myocardial Infarction: An Electrocardiographic Study Using Esophageal and Precordial Leads", *Am. Heart J.*, 15:414–25, 1938.

Nevertheless, the use of the esophageal ECG has not become popular for at least two reasons. First, all studies reported to the present time have used an electrode mounted at the end of a stomach tube, with considerable discomfort to the patient. Second, excessive amounts of baseline variation are present, due to the esophageal motion produced by respiration, peristalsis and cardiac contraction. These variations make it difficult to make accurate measurements, of small ST-segment shifts associated with ischemia.

Computer implementation of automatic detection of the ST-segment changes in the surface ECG and the esophageal ECG is highly desired. The goal of such a system is to provide an operator independent, reliable, and reproducible tool to aid clinicians in detection and management of myocardial ischemia of the total heart (anterior and posterior surfaces). Several algorithms have previously been implemented in computerized electrocardiographs to analyze the surface ECG during an exercise stress test. However, these methods have been ineffective in processing the unique surface ECG recorded during a transesophageal pacing procedure. This is because the presence of large pacing artifacts alters the shape of the sensed signals and complicates computerized ECG analysis.

Furthermore, to date, there has been no algorithm usable to analyze the esophageal ECG for detection of posterior ischemia. This has mainly been due to the technical difficulties that have been associated with noninvasive, high quality recording of the esophageal ECG, especially during transesophageal pacing.

Thus, there continues to be a need for apparatus and methods which make possible the processing of the unique surface ECG which can be recorded during a transesophageal pacing procedure. Preferably, such an apparatus and method will be relatively inexpensive and at the same time effective to block generated artifacts from interfering with the operation of the electrocardiograph.

SUMMARY OF THE INVENTION

A method and an apparatus are provided for detecting a selected heart condition in the person. In accordance with the present invention, a sensing electrode is used which can be positioned adjacent a posterior surface of the person's heart. The sensing electrode can be swallowed by the person and will be located in the esophagus adjacent the posterior surface of the heart.

The person's heart can then be stressed. This can be accomplished by having the individual physically exercise or by applying heart stressing electrical signals to the patient. The heart stressing, electrical signals can be generated by a cardiac stimulator.

The sensing electrode can detect electrical signals generated by the person's heart in response to stressing same. These signals can be filtered and processed.

The filtered and processed signals can then be analyzed to determine the presence or absence of selected heart conditions. An indicium indicative of the presence or absence of the selected condition can subsequently be generated.

An apparatus for automatically detecting the selected heart condition includes a swallowable multi-element electrode structure. The electrode structure can be positioned in the person's esophagus for receiving and transmitting electrical signals. Placement in the esophagus positions the electrode structure adjacent the posterior surface of the heart.

Stimulator circuitry can be coupled to selected of the elements of the electrode structure for supplying selected heart stressing electrical signals thereto. Detecting circuitry can be coupled to other elements of the electrode structure for detecting stress generated electrical signals from the heart.

The detected signals can be processed to eliminate variations due to artifacts as well as non-diagnostic patient characteristics. The processed signals can then be analyzed, utilizing measurement circuitry, to determine the presence or the absence of the selected heart condition. Indicium generating circuitry indicative of the presence or absence of the selected heart condition is coupled to the measuring circuitry.

Further, in accordance with the invention, the QRS complex of the person's heart can be detected and analyzed under stress conditions for the presence posterior ischemia. The use of a multi-element swallowable electrode which can then be positioned in the esophagus adjacent the posterior surface of the heart provides a particularly useful vantage point for the detection of such conditions.

Baseline wander or variation of electrical signals from the electrode structure due to peristalsis, respiration or cardiac contractions can be minimized or eliminated by means of a passive 10 Hertz high pass filter. Low frequency components eliminated by the high pass filter can be restored by inverse filtering the signal using a digital filter. The output of the inverse filter can be further processed using a digital linear phase 1 Hertz high pass filter. Such filters can be implemented using a programmed computer.

The digital output from the high pass filter, the processed signal, can be then measured for the purpose of determining the presence or absence of the selected heart condition. Measurement circuitry can also be implemented as a programmed digital computer. The measurement circuitry detects the R wave from the stimulated heart and determines that the R pulses have a spacing in time consistent with the pacing frequency of the stimulator. The peak values of the R wave are determined using the measurement hardware and software. The values of the QRS complex, a selected period of time before the peak, on the order of 60 milliseconds, and a selected period of time after the peak, on the order of 80 milliseconds, are measured.

The measurement circuitry can then subtract the two measured values. In an instance where the selected condition is a posterior ischemia, the difference between the two measured values will exceed a preselected threshold. In normal individuals without a posterior ischemia condition, the difference between the selected values is essentially zero. Variation from a difference on the order of zero can be an indicator of the presence of a posterior ischemia.

In order to minimize the effects of artifacts generated by the stimulated circuitry, an artifact or transient suppressor circuit can be coupled in series between the detecting elements of the electrode structure and the high pass 10 hertz input filter.

The suppressor includes circuitry for detecting an immediately pending transient. Circuitry is included for maintaining the value of an output electrical signal on the output line at a value substantially equal to the value of an input data signal on the input data line immediately prior to the initiation of the transient. The transient is thus blocked from the output data line. Circuitry is also included for determining when to cease maintaining the output value at the pre-transient input value.

Where a transesophageal pacer is being used in combination with an esophageal pacing electrode, the transient suppressing circuitry can detect when the pacing unit generates a pacing initiating leading edge of an electrical signal. The detecting circuitry of the transient suppressor can include a mono-stable multi-vibrator which is triggered by the leading edge of the pacing signal. One or more sample and hold amplifiers can be used as isolation devices between the input data signal line or lines and the output data signal line or lines.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 4 is an overall system block diagram in accordance with the present invention;

FIGS. 6A, 6B and 6C are graphs of voltages of function of time illustrative of the operation of the artifact suppressor of FIG. 5;

DETAILED DESCRIPTION OF THE PREFERRED EMBODIMENT

Figure 1:
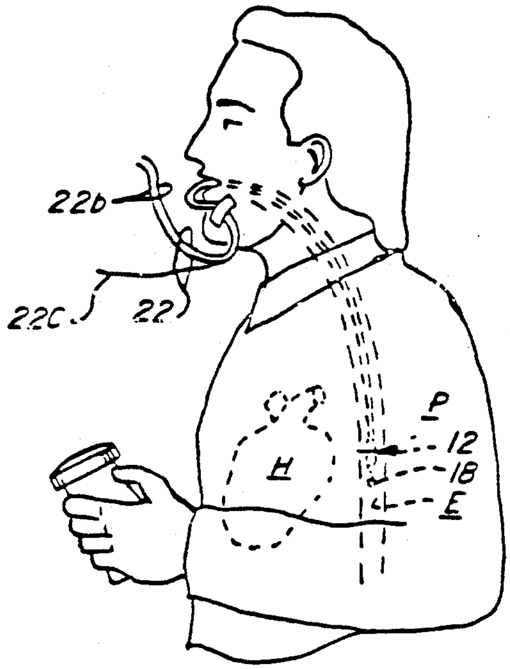
FIG. 1 is a side view of a patient with a previously positioned esophageal electrode.

While this invention is susceptible of embodiment in many different forms, there is shown in the drawing and will be described herein in detail a specific embodiment thereof with the understanding that the present disclosure is to be considered as an exemplification of the principles of the invention and is not intended to limit the invention to the specific embodiment illustrated.

FIG. 1 illustrates a patient P connected to a system 10 in accordance with the present invention. The system 10 incorporates a three element esophageal electrode 12. The electrode 12 is illustrated in FIG. 1 located in the esophagus E and behind the heart H of the patient P. It will be understood that the esophageal electrode 12 can be located appropriately with respect to the heart H to function as intended by adjusting the vertical position of the electrode 12 in the esophagus E.

The electrode 12 carries three conductors 14, 16 and 18. In this regard, two alternate esophageal electrodes 12 and 12*a* are illustrated in FIGS. 2 and 3.

Bipolar esophageal electrodes are known in the prior art and one form thereof is described and disclosed in commonly assigned, copending U.S. Pat. Application entitled Improved Esophageal Electrocardiography Electrode, Ser. No. 930,748 filed Nov. 13, 1986. The disclosure of that application is incorporated herein by reference.

Figure 2:
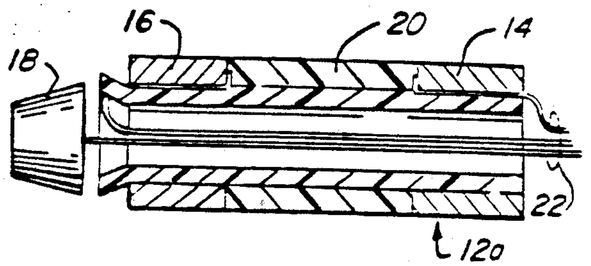
FIG. 2 is a view in section of an esophageal electrode with three elements.
Figure 3:
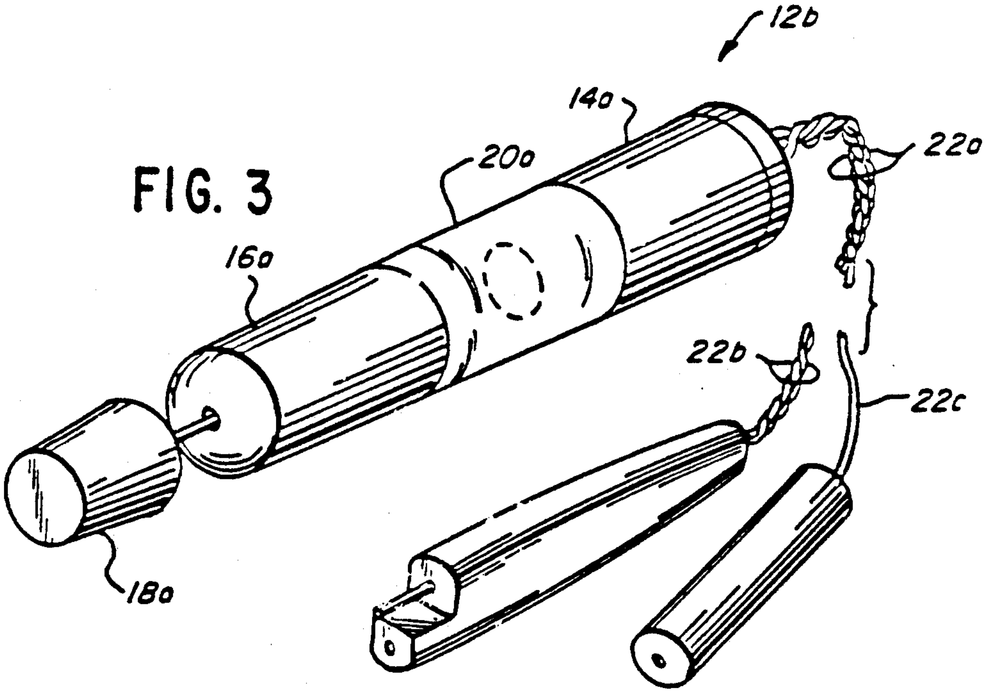
FIG. 3 is a view in perspective of an alternate embodiment of a three element esophageal electrode.

With respect to FIGS. 2 and 3, three element esophageal electrodes can be formed with a variety of different structures. However, in accordance with FIGS. 2 and 3, such electrodes will include a body portion 20 or 20*a* which carries two spaced apart primary or pacing electrodes 14, 16 or 14*a*, 16*a*. The use of electrodes 14 and 16, or 14*a* and 16*a* is well known in connection with transesophageal pacing as described in the above-noted copending patent application.

The electrodes 12*a* or 12*b* each are provided with a three conductor cable 22 or 22*a*. The cable 22 or 22*a*, in addition to being used to position the electrode 12 or 12*a* in the esophagus E provides electrical connection therewith.

Two of the conductors of the cable 22*a*, associated with pacing electrodes 14 and 16, form a two conductor cable 22*b*. The third conductor associated with the third electrode 18, is available as a single conductor 22*c*.

FIG. 4 illustrates the elements of the system 10 coupled to the patient P. In addition to the three element electrode 12, the system 10 includes a transesophageal cardiac stimulator or pacer 30 of a conventional type. For example, the pacer or stimulator 30 could be an Arzco Medical Electronics, Inc. Model 7.

As is conventional, the stimulator or pacer 30 is coupled via the two conductor cable 22*b* to the two electrodes 14 and 16 for transesophageal pacing. The stimulator or pacer 30 is also coupled via a communication cable 32 to a stimulator artifact suppressor 34.

As will be discussed further subsequently, the artifact suppressor 34 includes a plurality of inputs 36 and a plurality of outputs 38. The inputs 36 can vary based on the type of application in which the suppressor 34 is being used.

In an embodiment where the suppressor 34 is being used in combination with the three element electrode 14, the inputs 36 include the conductor 22*c* coupled to the third conductor 18 of the esophageal electrode 12. The inputs 36 also include a surface electrode 39*a* located on the manubrium of the patient P and coupled by a conducting member 40a to the suppressor 34.

The set of inputs 36 also includes a connection to a surface electrode 39b at the C5 anatomical position of the patient. The C5 electrode is coupled via a conducting member 40b to the respective input of the suppressor 34.

Finally, the inputs 36 include a connection to a surface electrode 39c coupled to the right leg of the patient which serves as the system electrical ground. The right leg electrode is coupled via a conducting member 40c to a respective input of the suppressor 34. The surface electrodes 39b and 39c at the C5 position and the right leg position are conventional electrode positions used in connection with electrocardiography.

Conventional electrocardiographs have a total of 10 inputs which include inputs from a right leg surface electrode, a right arm surface electrode, (in the present instance replaced by the manubrium electrode connection), a left arm surface electrode, (replaced in the present system by the connection to the third electrode 18 in the esophageal electrode), a left leg surface electrode (replaced in the present system with a connection to the C5 anatomical electrode) and standard chest electrodes C1–C6. The system 10 is useful with standard electrocardiographs for the purpose, when utilizing a three element esophageal electrode such as electrode 12, for providing a two channel-system usable in detecting posterior and anterior cardiac wall abnormalities.

The system 10 is particularly useful with patients who are unable to perform an adequate exercise stress test. In this system, the stimulator 30 in conjunction with electrodes 14 and 16 of the esophageal electrode 12 can be used to pace the heart at elevated rates for diagnostic purposes without any necessity of having the patient physically exercise at the same time.

Further with respect to FIG. 4, the four inputs to the artifact suppressor 34 on conductors 22c, 40a, 40b and 40c are processed by the artifact suppressor 34. The processed results can be transmitted by the output data lines 38 implemented as a cable 44 having at least four conductors 44a, 44b, 44c and 44d to the electrocardiograph 48. The four conductors of the cable 44 are coupled respectively to the left arm, the right arm, the left leg and the right leg inputs of the electrocardiograph 48. A two chart output results which can be used for anterior and posterior analysis of the heart H.

It will be understood that the electrocardiograph 48 is a conventional 10 lead electrocardiograph of the type known to those skilled in the art as well as practicing clinicians. However, with respect to the system 10 of FIG. 4 only four of the input leads to the electrocardiograph 48 are being used.

The input dynamic range of typical electrocardiographs can be as large as ± 10 mV. On the other hand, assuming a typical pacing current of 20 mA and a patient equivalent impedance of 1000 ohms, the potential that is developed in the esophagus can be as high as 20 V which is outside the input dynamic range of standard electrocardiographs. Due to this inherent limitation of electrocardiographs, it is necessary to suppress the large pacing artifacts. Suppression can be obtained by different methods. For example, during the delivery of the stimulation pulse, the inputs of the recording amplifier of the electrocardiograph can be shorted together or disconnected from the signal source. However, in these cases switching artifacts appear since the amplifier is switched from a nonzero output to a zero output. These switching artifacts are often large, and hence, the above do not offer a satisfactory solution to the problem. In accordance with the present invention, the suppressor 34 provides an improved and more satisfactory solution.

Figure 5:
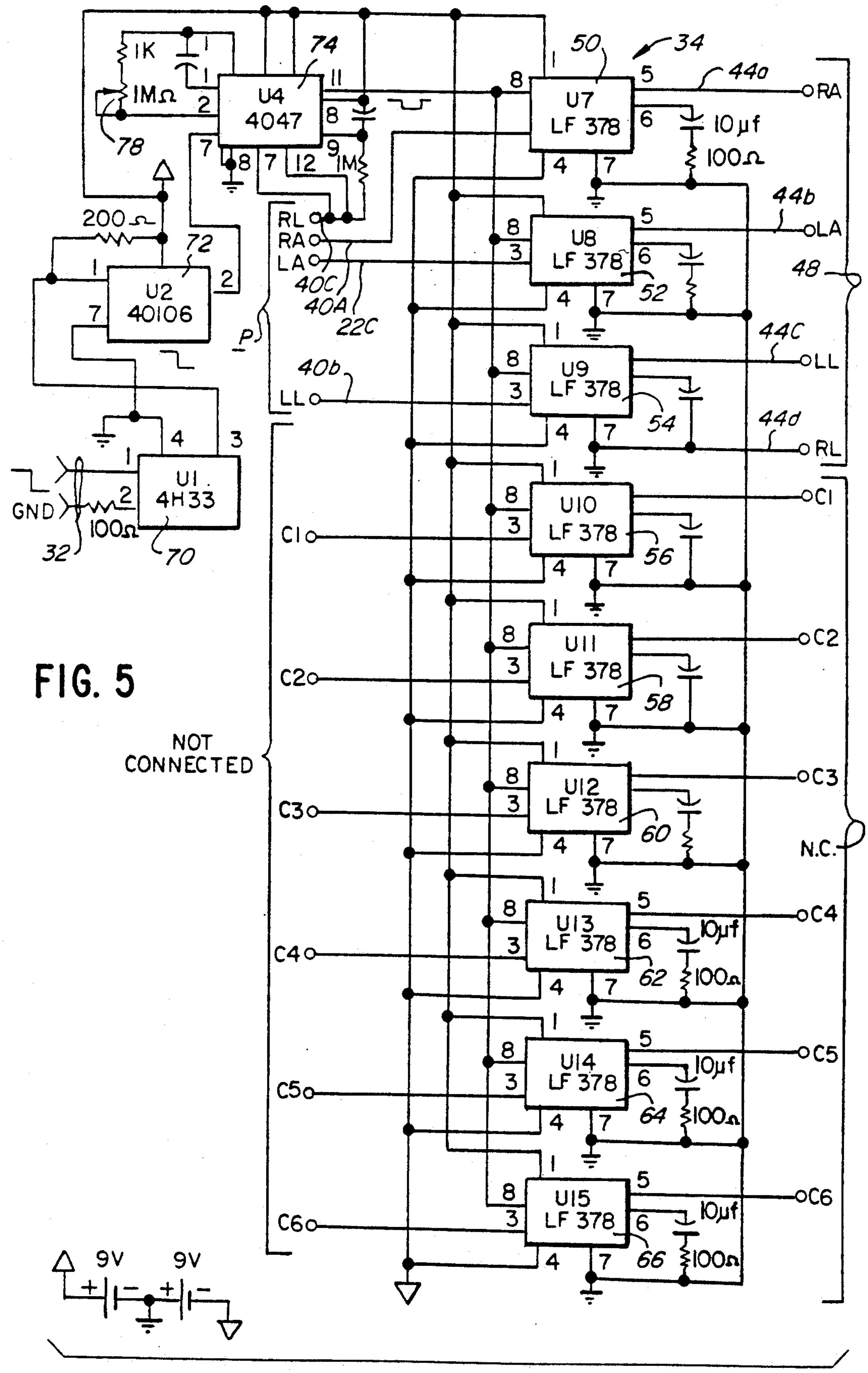
FIG. 5 is a detailed electrical schematic of an artifact suppressor in accordance with the present invention.

FIG. 5 is a detailed schematic diagram of the suppressor 34. The circuitry of FIG. 5 suppresses large pacing artifacts before those signals can enter the electrocardiograph 48. Hence, saturation of the electrocardiograph 48 is avoided. Since the suppressor 34 is located between the input data lines 36 and the output data lines 38, the integrity of the signals on the lines 36 will be maintained.

National Semiconductor LF398 sample and hold circuits 50–66 are used to block artifacts on the input lines 36 from appearing on the output lines 38. Each sample and hold amplifier operates as a unity gain follower (gain error < 0.004%) in the sample mode. Each has fast acquisition time (<10 μs), high input impedance (10G ohms), wide bandwidth (100 kHz), low output impedance (0.5 ohms), very low output noise (50 to 30 nV $Hz^{\frac{1}{2}}$in the sample mode, and 130 to 50 nV $Hz^{\frac{1}{2}}$in the hold mode, in the frequency range 1 to 100 Hz), and differential sample-hold logic threshold of 1.4V. As a result, the integrity of the signals on the input lines 36 is not compromised by the suppressor 34 which is located between the patient P (signal source) and the electrocardiograph 48.

The circuitry in the suppressor 34 receives inputs on the cable 32 from the transesophageal cardiac stimulator 30. The stimulator 30 is capable of delivering square wave constant current pulses of up to 40 mA in amplitude, 10 ms in width, and 600 pulses per minute across impedances of up to 3000 ohms.

As FIG. 5 illustrates, a down going pacing signal S3, from the stimulator 30 is coupled via the cable 32 and an optoisolator 70 to a Schmitt trigger 72. The down going output of the Schmitt trigger 72 switches the mono-stable multi-vibrator 74.

The down going output pulse of the mono-stable multi-vibrator 74 provides a control signal 76 for the sample and hold circuits 50–66. When this signal is high about 9 volts, the circuits 50–66 are in a sample mode. When it is low about zero volts, the circuits 56–66 are in a hold mode.

In the sample mode, the outputs of the circuits 50–66 closely follow their corresponding input signals. In the hold mode, the values of the input signals just before switching are held and the outputs are equal to the corresponding, held input values.

It has been found that the combination of a hold capacitor value of 10 μF in series with a 100 ohm resistor yields optimal results taking into account droop rate and other factors. The hold duration is controlled by varying the pulse width of the output of mono-stable multi-vibrator 74 which is determined by a 1 mohm potentiometer 78. This control provides a range of hold duration or blanking period from 0 to 100 ms.

FIG. 6 illustrates a plurality of graphs of voltages as a function of time which further explain the operation of the suppressor 34. In graph FIG. 6A, the pacing signal S3 generated in the stimulator 30 on the cable 32 is illustrated. The pacing signal has a period on the order of 100–1000 milliseconds. The graph of FIG. 6B illustrates the output of the mono-stable multi-vibrator 74 on the line 76, is the hold signal. The hold signal or blanking signal can be adjusted to have a duration between 0 to 100 milliseconds.

The graph of FIG. 6C, illustrates the pacing signal generated by the stimulator 30.

In the system of FIG. 5, the pacing function is initiated when the signal S3 on the line 32 makes the down going transition thereon which triggers the mono-stable multi-vibrator 74, best illustrated in FIG. 6C. It will be understood that a prefacing window could be introduced by delaying the application of the signal on the line 32 to the esophageal electrode 12. This could readily be accomplished by introducing a second mono-stable multi-vibrator into the circuitry 34. This second mono-stable multi-vibrator will be driven by the output of the Schmitt trigger 72. The second multi-vibrator could be provided with a relatively short delay period, on the order of 5 milliseconds. Output from the second mono-stable multi-vibrator could then be fed back to the stimulator 30 to trigger the pacing signal on the conductors 22*b*. In such an instance, the sample and hold control signal on the line 76 will go low on the order of 5 milliseconds before the pacing signal is initiated on the cable 22*b*.

Figure 7A:
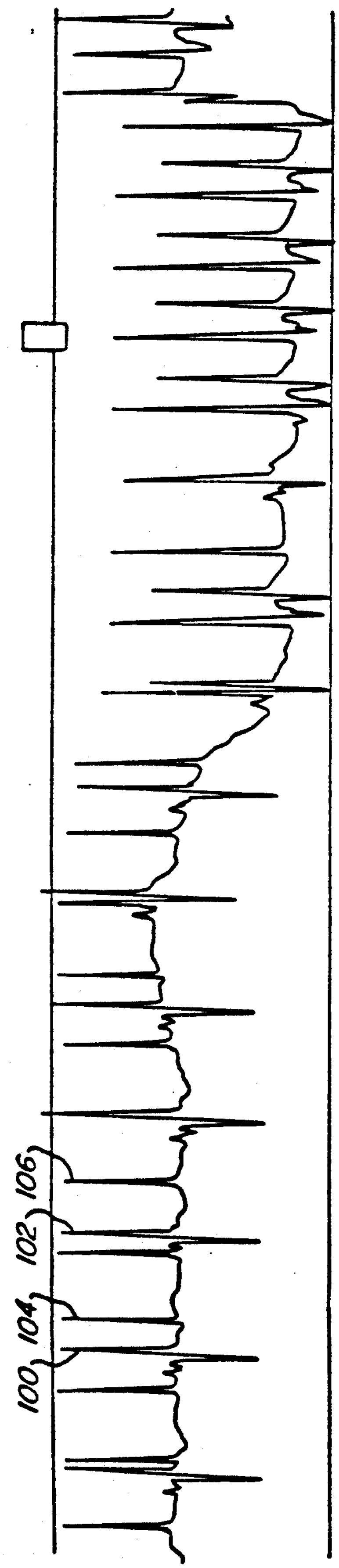
FIGS. 7A and 7B represent a two chart electrocardiograph illustrating pacing artifact and baseline variations as pacing current is varied.
Figure 7B:
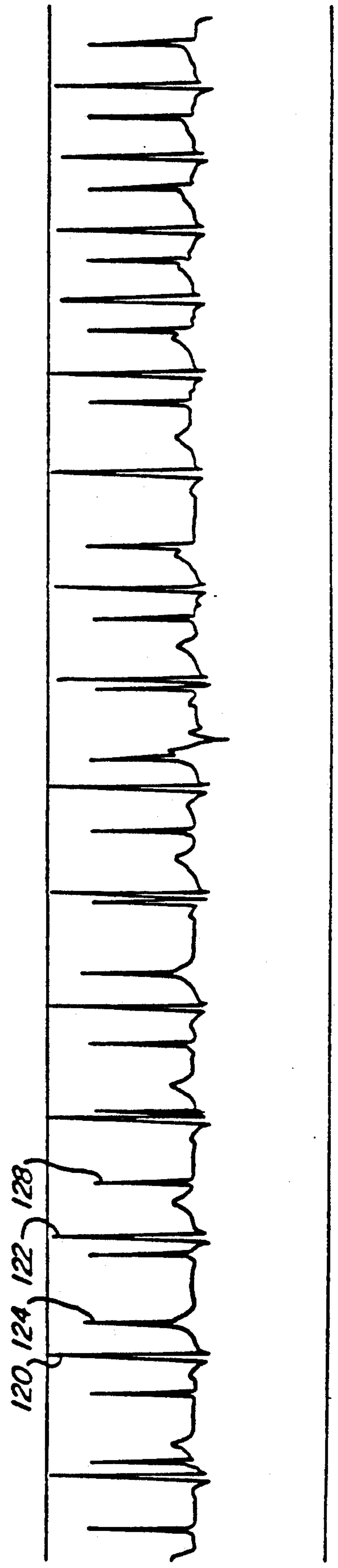

FIGS. 7A and 7B illustrate the type and magnitude of artifacts generated by the stimulator 30 as the operation of that unit has been known from the prior art. FIG. 7A is one chart off of the ECG 48 illustrating signals on the esophageal/manubrium lead combination 22*c*/40*a*. Pulses 100 and 102 of the graph of FIG. 7A illustrate a QRS signal as is known in the prior art. Immediately following the QRS signal, pulses 104 and 106 are pacing artifact signals generated in response to pacing output from the stimulator 30. In addition to the artifact pulses 104 and 106 which are injected between the diagnostically useful QRS pulses 100 and 102, the baseline of the signal in FIG. 7A drifts substantially as pacing current is increased.

In FIG. 7B, a plot of the combination of the C5 anatomical electrode and the manubrium electrode is illustrated. Once again, the QRS pulses, such as pulses 120 and 122 are followed by pacing artifact pulses 124 and 126.

Figure 8A:
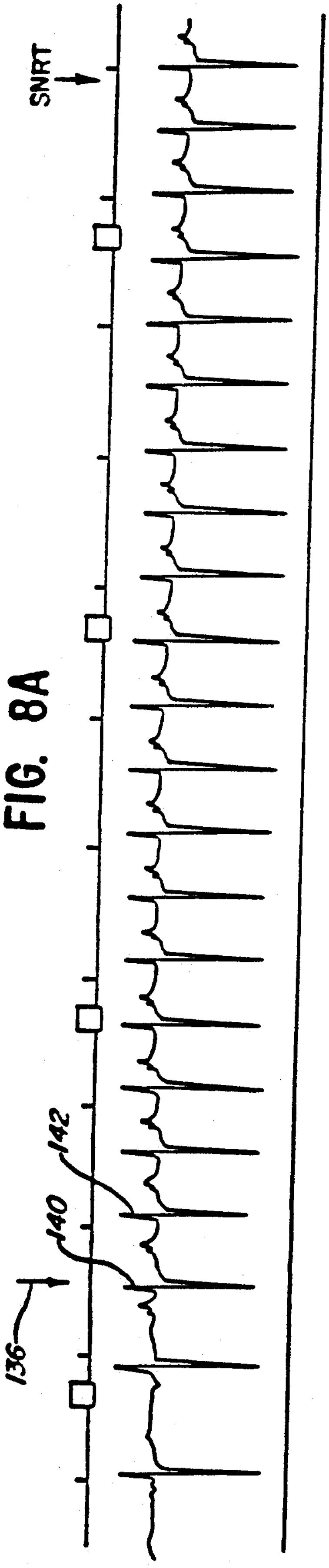
FIG. 8A is a diagram of an electrocardiograph as in FIG. 7A illustrating the suppression effects of the artifact suppressor of FIG. 5 at a pacing rate of 120 beats/minutes.
Figure 8B:
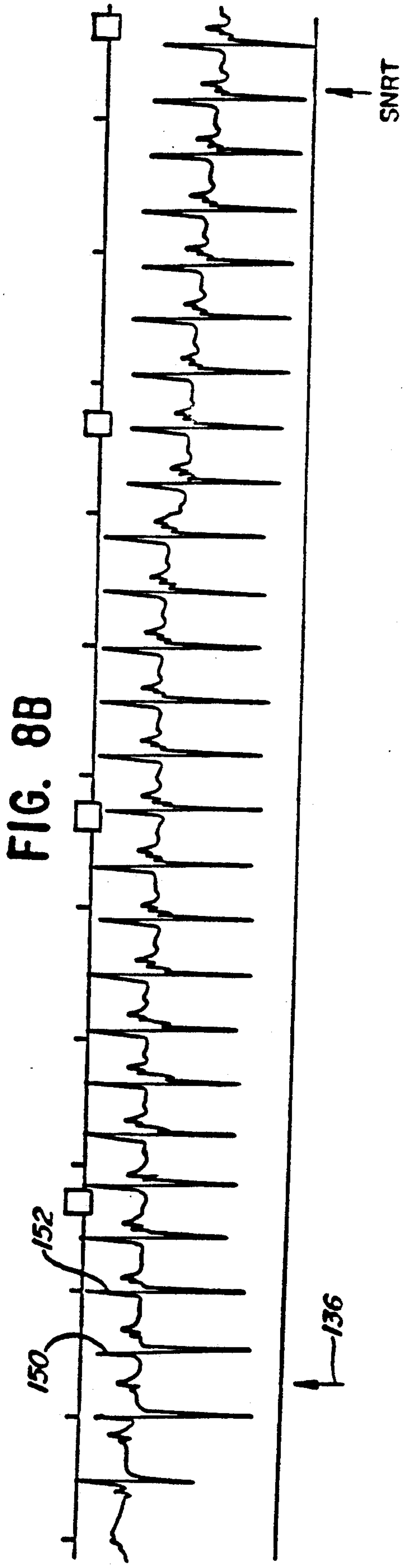
FIG. 8B is a diagram of an electrocardiograph as in FIG. 8A illustrating the suppression effects of the artifact suppressor of FIG. 5 at a pacing rate of 150 beats/minute.

In contradistinction to the graphs of FIG. 7 which were prepared without using the suppressor 34, graphs from FIG. 8A and 8B utilizing the same electrode combinations but with the suppressor 34 present as in FIG. 4 display complete blanking of the artifact effects as well as steady baseline.

In FIGS. 8A and 8B the patient's heart beat has been captured by the stimulator 30 at a time indicated at 136. Capture heart rate corresponded to 120 beats per minute.

With respect to FIG. 8A, the QRS signals, 140 and 142 are being generated in response to the pacing signals from the stimulator 30 at a rate of 120 beats per minute. FIG. 8A corresponds to FIG. 7A in that it is a chart of the esophageal/manubrium electrode input combination to the electrocardiograph 48.

FIG. 8B illustrates a corresponding electrode combination as in FIG. 7A of the esophageal/manubrium electrode input combination. The chart of FIG. 8B also exhibits complete blanking of the pacing generated artifacts and a steady baseline. The QRS pulses are clearly illustrated as pulses 150 and 152 also corresponding to a captured heart rate at 150 beats per minute.

Figure 9:
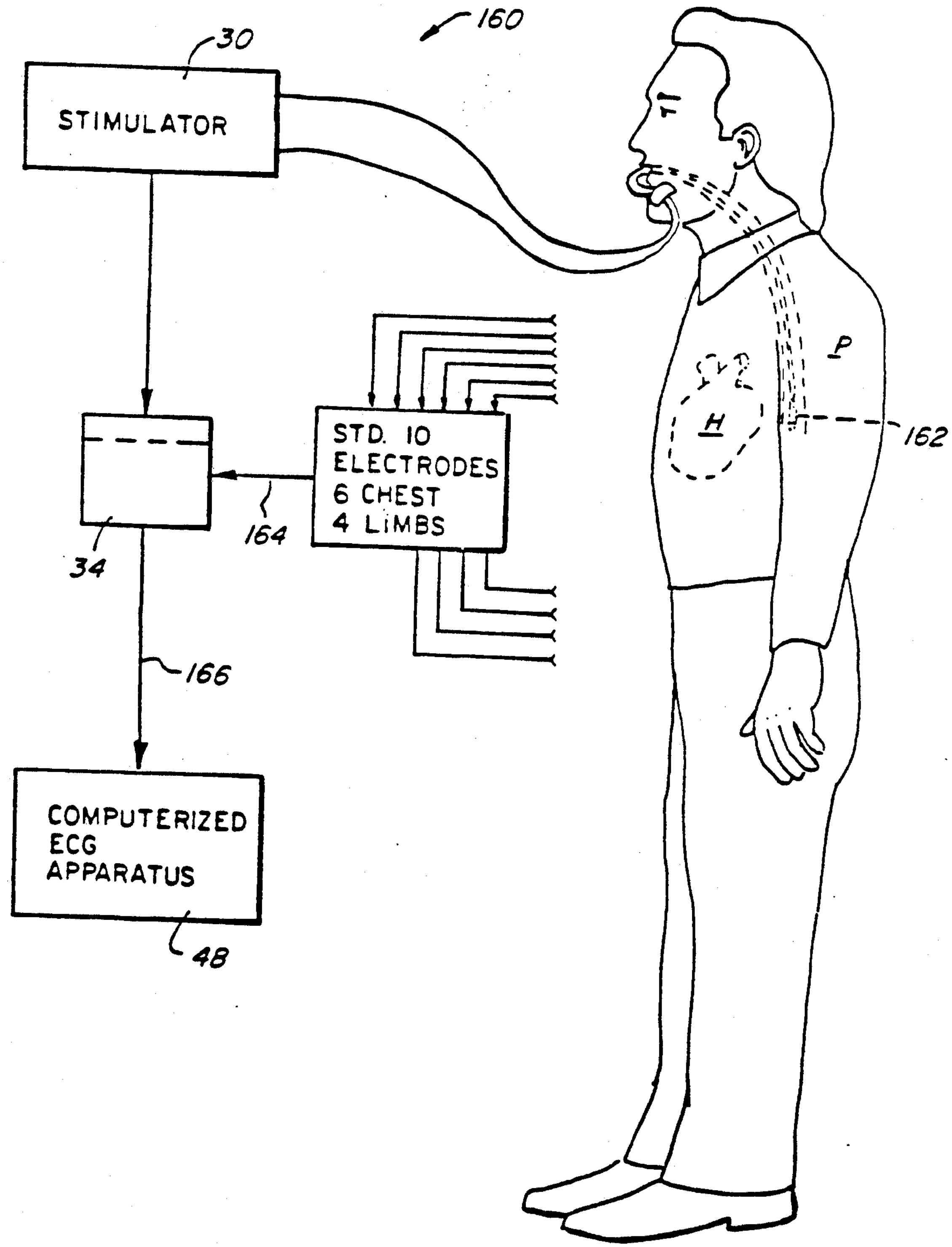
FIG. 9 is an overall block diagram of an alternate system incorporating the artifact suppressor of FIG. 5.

The suppressor 34 can also be used in a system 160 as in FIG. 9. In the system 160, the stimulator 30 is used in combination with a standard two element esophageal electrode 162 of a known type. In accordance with the system 160, the standard 10 electrocardiograph electrodes are located on the patient P as is conventional in connection with electrocardiography.

A standard 10 electrode patient cable 164 can be used. The 10 electrodes are coupled through the 10 inputs of the suppressor 34 as illustrated in FIG. 5. In the embodiment of the system 160, all 10 electrodes are connected to corresponding inputs to the suppressor 34. A standard 10 conductor cable 166 is used to couple the output lines of the suppressor 34 to the electrocardiograph 48.

If desired, the electrocardiograph 48 could be a conventional analyzing, computerized system often used for analyzing exercise stress, ECG. Such devices are especially suited for providing immediate analysis of a set of input signals. However, they are completely unable to analyze input signals in the presence of pacing artifacts, such as the artifacts illustrated in FIGS. 7A and 7B. Hence, the system 160 of FIG. 9 enables the esophageal stimulator 30 to be used in combination with a computerized electrocardiograph and obtain the immediate benefits of the automated analysis that such units provide.

Figure 10A:
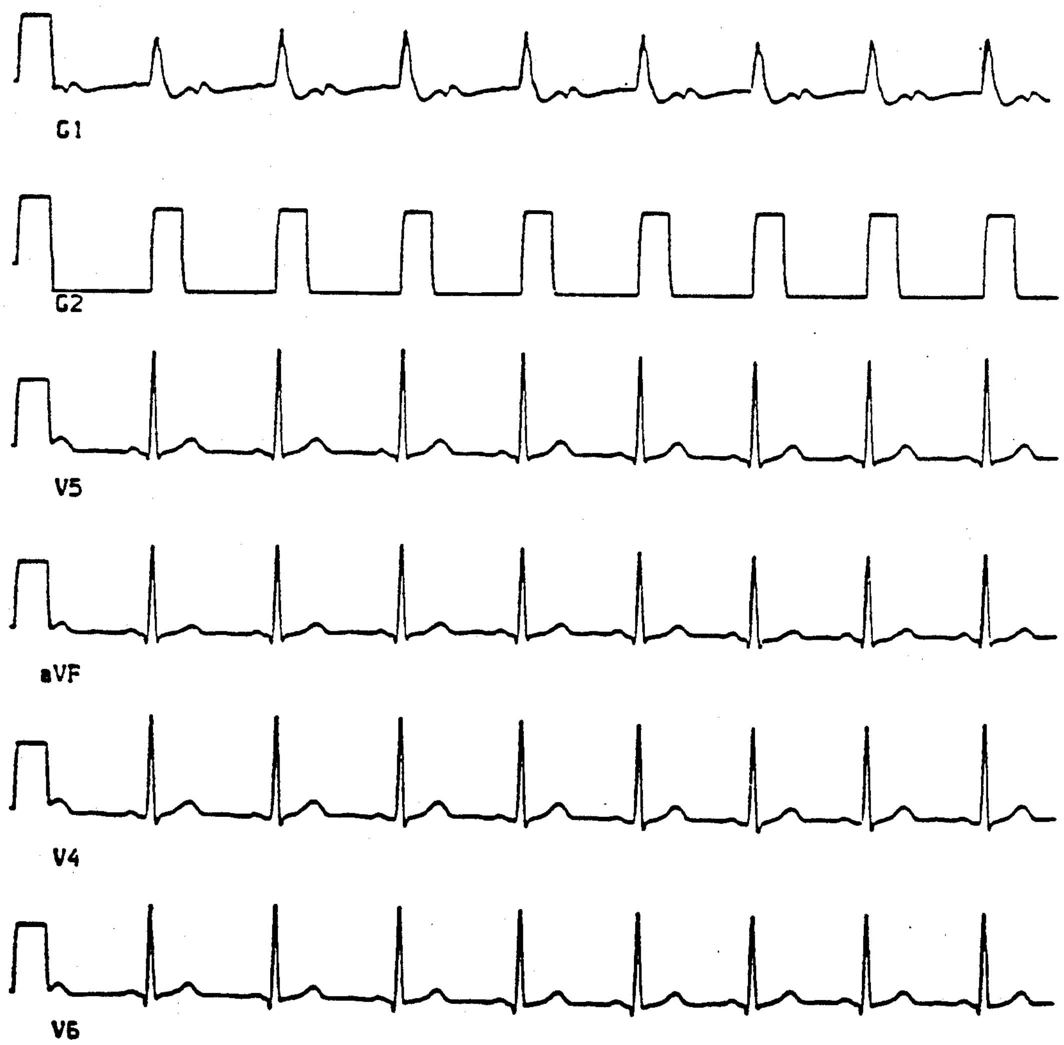
FIGS. 10A-D illustrate electrocardiographs taken under various operating conditions.

FIG. 10A is a chart generated by a commercially available computerized exercise electrocardiograph system (Marquette CASE-12). The unit was coupled to a patient as is conventional with surface electrodes, no pacing of any type was used.

FIG. 10A illustrates, from bottom to top, a signal from the surface lead conventionally identified as V6, a signal from the surface lead conventionally identified as V4, a signal from the surface lead conventionally identified as aVF, a signal from the surface lead conventionally identified as V5, a signal G2 from the internal trigger logic of the unit indicative of QRS complexes in the surface leads is formed from thresholding the top signal G1.

Signal G1 is in turn conventionally formed by squaring several surface leads, adding them and taking the square root of the result. For each occurrence of a QRS complex in the surface leads, a pulse is present in the signal G2. These pulses confirm the presence of a QRS complex. The computerized system uses this information to locate the ST-segment for ST measurements believed to be important in diagnosis of coronary artery disease.

In FIG. 10A, the associated, unpaced heart rate of the patient was sensed as 79 beats per minute.

Figure 10B:
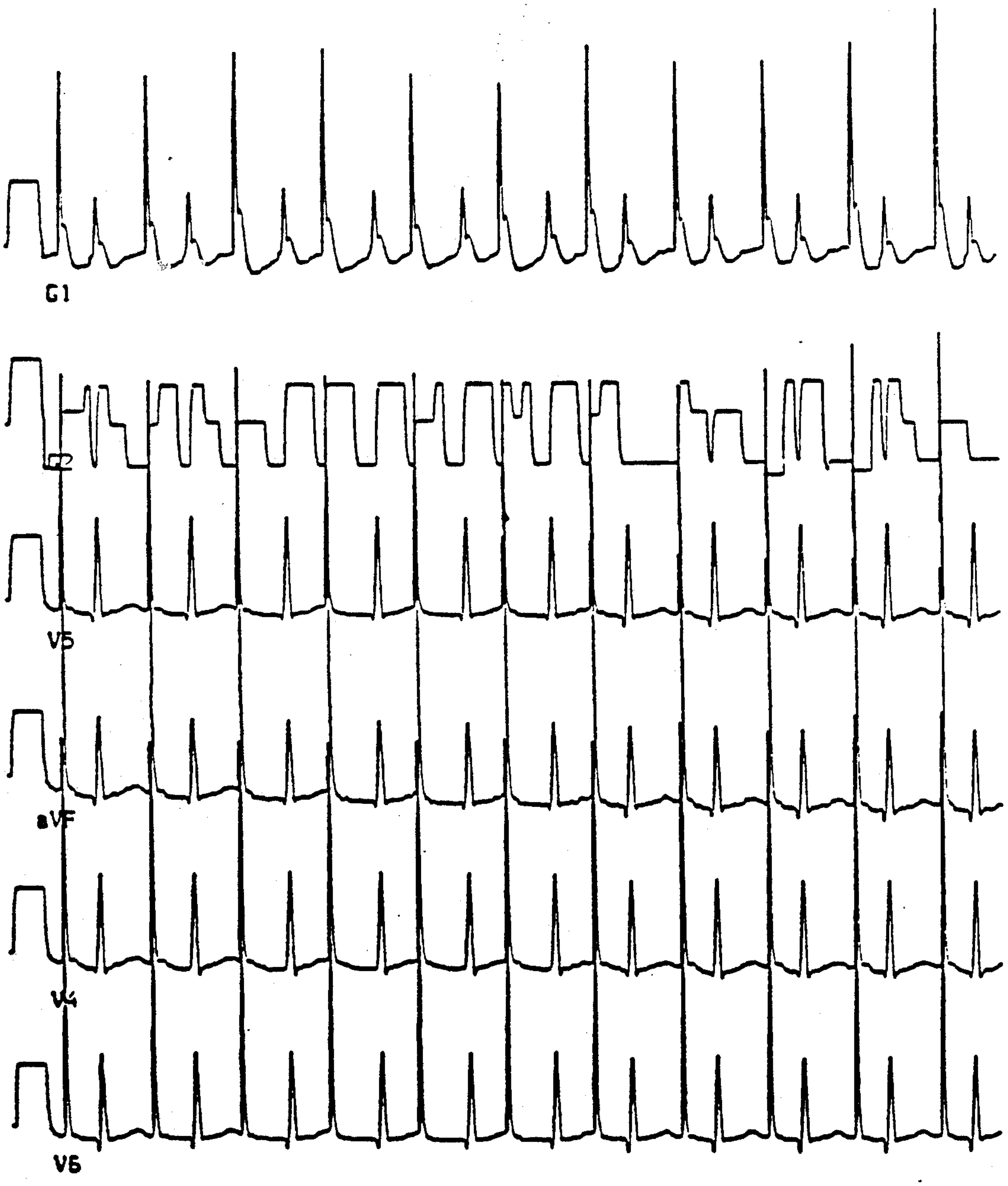

In FIG. 10B, the same exercise electrocardiograph unit was used in connection with a transesophageal paced heart. For pacing purposes, a conventional two element esophageal electrode as noted previously was used. The Arzco Model 7 stimulator previously noted was also used. The system was arranged as generally indicated in FIG. 9 without the suppressor 34 between the patient and the electrocardiograph 48.

The pacing heart rate was 130 beats per minute. As can be seen in FIG. 10B, the shape signal G2 of the computerized system has been distorted by the presence of large pacing artifacts (the large pulses in FIG. 10B) in the surface electrode leads which occur during pacing stress. Thus, the computerized system could not function properly and no ST-segment measurements were properly reported. Also, the heart rate determined by the system was incorrectly reported as 194 bpm. This did not correspond to the pacing heart rate of 130 bpm.

Figure 10C:
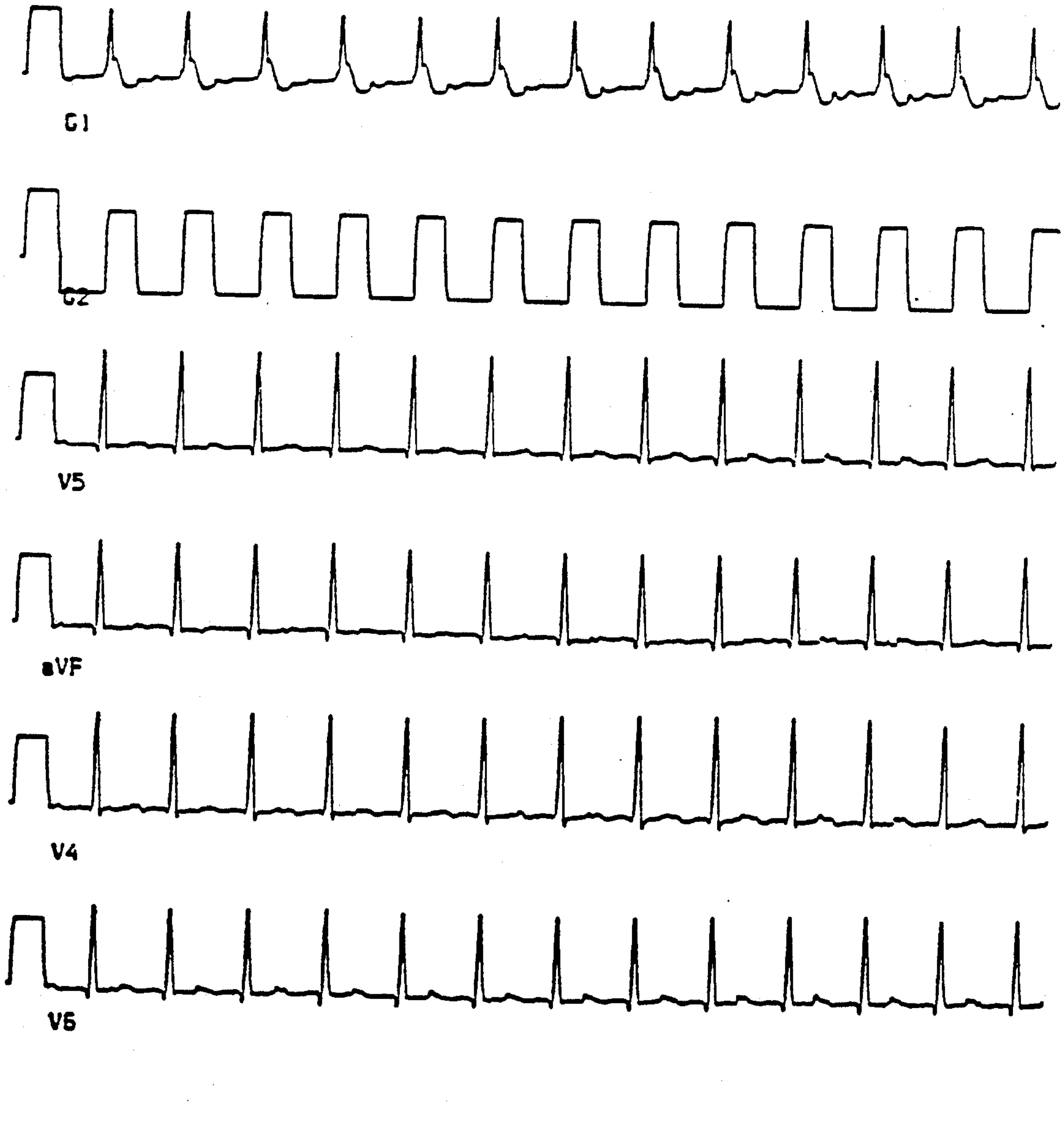

FIG. 10C illustrates the operation of the stimulator 30 and the same exercise electrocardiograph system coupled to the suppressor 34 as in FIG. 9. The large pacing artifacts have been suppressed. The signal G2 is similar in shape to the signal G2 in FIG. 10A. Each pulse in the signal G2 corresponds to the QRS complex detected in the surface electrodes.

The pacing rate when the graphs of FIG. 10C were generated was 130 beats per minute.

In the FIG. 10C, the heart rate was correctly determined by the electrocardiograph as 127 bpm close to the pacing rate of 130 bpm.

Figure 10D:
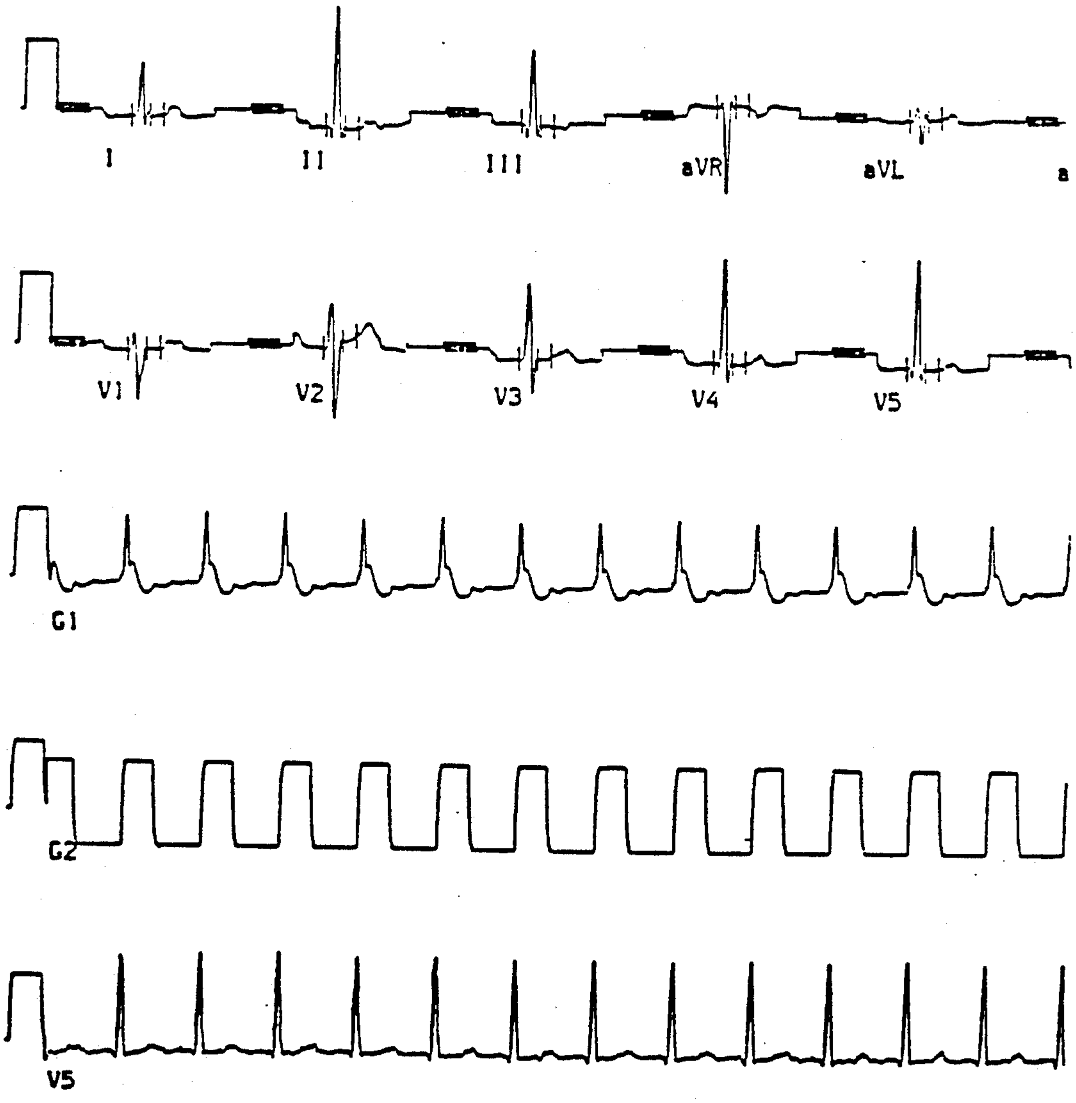

FIG. 10D is similar to FIG. 10C. FIG. 10D was generated with a system as in FIG. 9. In addition, FIG. 10D illustrates the ST-segment measurements in the top 2 waveforms which the electrocardiograph reported during a pacing session at 130 bpm with the suppressor 34 operating. In this instance, the heart rate was reported by the electrocardiograph as 129 beats per minute. This was very close to the pacing rate of 130 beats per minute.

Hence, the suppressor 34 enables the use of commercially available electrocardiographs in conjunction with transesophageal pacing. This heart stress modality can be used with those patients who cannot perform an adequate conventional dynamic exercise stress test.

It will also be understood that alternate types of circuitry could be used without departing from the spirit and scope of the present invention. For example, instead of sample and hold circuits, digital circuits could be used to store a digitized input data value. That value could be converted to analog form and presented to an output data line.

Figure 11:
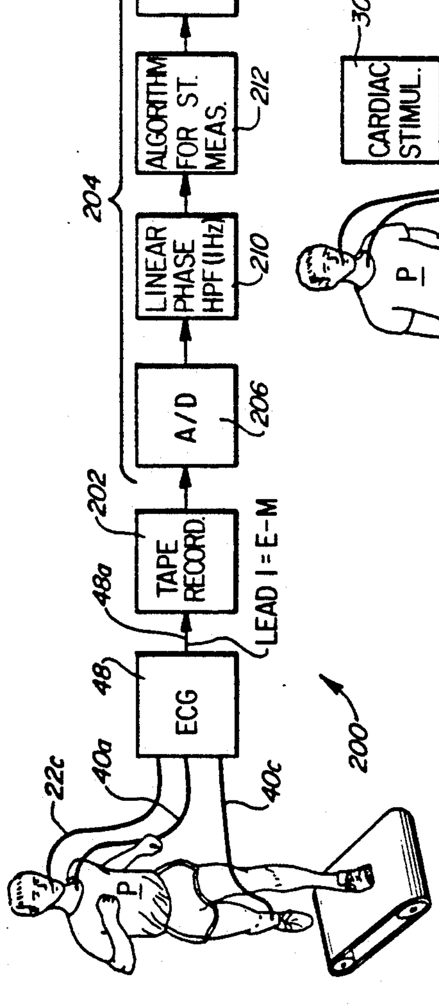
FIG. 11 is a block diagram of a system in accordance with the present invention for automatic detection of posterior ischemia usable with an exercisable subject.

A system 200 is illustrated in the block diagram of FIG. 11. The system 200 can be used in conjunction with an exercisable subject P for the purpose of automatically detecting the presence or absence of posterior ischemia. The system 200 includes the electrocardiograph 48 which is coupled to a swallowable three element esophageal electrode of the type illustrated in FIGS. 2 or 3 previously discussed.

The electrocardiograph 48 is coupled to the swallowable electrode by the line 22*c*. In addition, it is coupled to the subject P by the line 40*a* and the line 40*c* respectively attached to the manubrium electrode 39*a* and the right leg electrode 39*c* as previously discussed.

Output from the electrocardiograph 48 is recorded on an instrument tape recorder 202 to permit off-line processing. A computer system 204 includes an input analog to digital converter 206 to receive prerecorded signals from the tape recorder 202. The computer 204 also includes an output digital to analog converter 208.

The computer 204 functions with a control program to implement a digital linear phase high pass filter 210. The filter 210 has a 1 hertz cut-off frequency and is provided to eliminate low frequency baseline variation. The baseline variation can be generated or due to peristalsis, respiration and/or cardiac contractions.

Design methods for the filter 210 are well-known and are described for example in signal processing text books such as: Oppenheim and Schafer, *Digital Signal Processing*, Prentice-Hall Inc., Englewood Cliffs, NJ 1975, and Ahmed and Natarajan, *Discrete-time Signals and Systems*, Reston Publishing Co., Reston, VA 1983.

Digitized and filtered signals output from the filter 210 are then processed further by measurement element 212. Measurement element 212 could also be implemented as a portion at the control program for the computer 204. The measurement element 212 determines selected points of the digitized and filtered wave form and then processes, using a variety of available techniques the selected regions or points of the digitized signal so as to generate an indicium of the presence or absence of the posterior ischemia.

The digitized and filtered output can then be reconverted to an analog signal in the digital to analog converter 208 for manual analysis if desired.

Hence with respect to FIG. 11, the subject P stresses the heart while running on the treadmill. The stressed heart generates electrical signals which can be detected off of the posterior region thereof using the conductor 22*c* which is coupled to the sensing electrode located in the esophagus. Signals from the esophageal electrode 18, 18*a* and the manubrium electrode 39*a* can be preliminarily processed in the electrocardiograph 48 as discussed previously. Those signals can then be digitized, filtered and analyzed for the presence or absence of the posterior ischemia.

Any conventionally available electrocardiograph with sufficient dynamic range can be used as the cardiograph 48. The tape recorder 202 could be a high fidelity FM instrumentation type of tape recorder such as a Hewlett-Packard Model 3964A. The programmed digital computer 204 could be implemented using an IBM PC/AT type computer of equivalent. The analog to digital converter 206 and digital to analog converter 208 could be implemented using Tecmar Lab Master type units.

Figure 12:
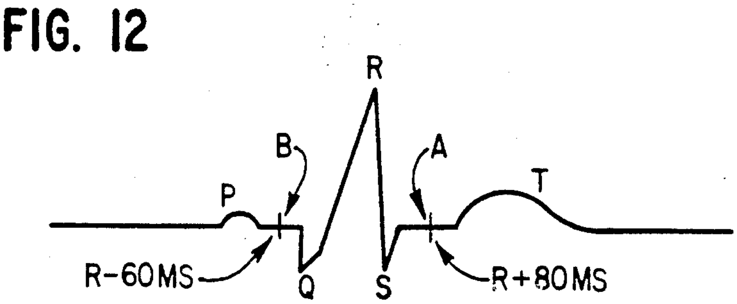
FIG. 12 is a plot of a typical QRS wave form illustrating various measurement regions.

FIG. 12 is a diagram of typical QRS signal of the type present on lead 1, 48*a* of the cardiograph 48. This is a well-known type of signal having regions identified as the QRS regions of the signal. In the presence instance, as previously described, the lead 1 signals are generated, not as is conventionally done with surface electrodes, but with the esophageal electrode coupled to the conductor 22*c* in combination with the manubrium electrode coupled to the conductor 40*a*.

The waveform of FIG. 12 has two regions A and B defined thereon. Region A includes a point defined to be 80 milliseconds subsequent to the peak of the R pulse. Region B includes a point defined to be 60 milliseconds before the peak of the R point.

It is known that if the values at the 80 millisecond and 60 millisecond points are essentially equal that this is an indication of an absence of a posterior ischemia. It is also known that if the difference between the values at the 80 millisecond point and the 60 millisecond point is not substantially equal to zero that a posterior ischemia may be present in the heart of the subject P. The present method and apparatus utilize these characteristics for the purpose of automatically generating an indicium of the presence or absence of posterior ischemia.

Figure 13:
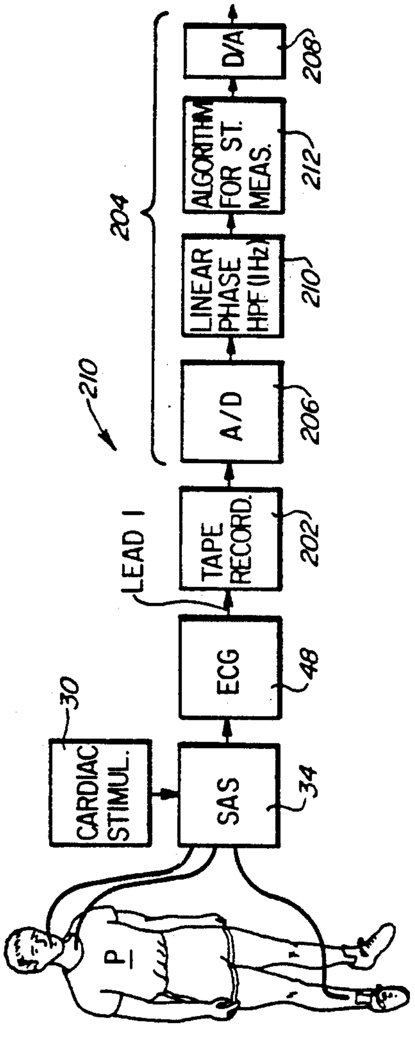
FIG. 13 is a block diagram of a system for automatically detecting posterior ischemia in connection with a subject whose heart is being paced.

FIG. 13 is an alternate system usable for the purpose of detection of posterior ischemia with a subject P who need not be exercising. The advantage of the system 210 is that it utilizes the cardiac stimulator 30 which results in very carefully controllable heart stressing.

This controllable heart stressing can be used with those subjects who are unable to exercise. However, it is also advantageous to use it with subjects who can exercise simply because it results in a very controlled test condition.

The system 210 also includes the artifact suppressor 34 previously discussed so that signals received by the electrocardiograph 48 are not distorted by the pacing signals generated by the stimulator 30. Other elements of the system 210 correspond to the previously discussed elements of the system 200.

Figure 14:
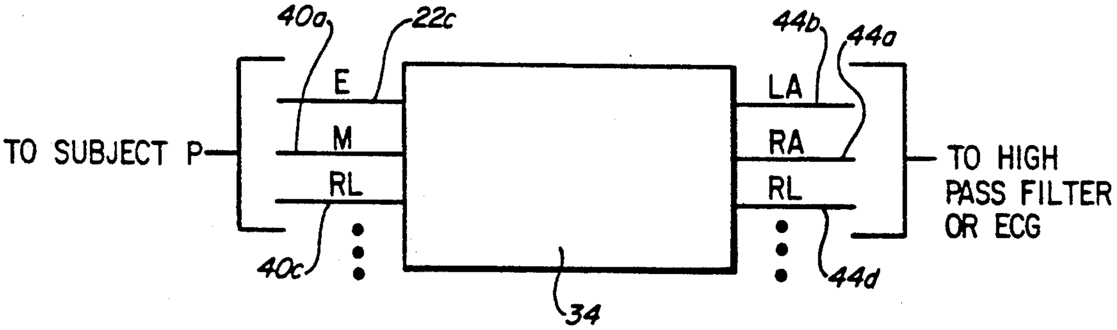
FIG. 14 is a block diagram illustrating various of the connecting leads of the system of FIG. 13.

FIG. 14 illustrates in greater detail the interconnections between the esophageal electrode coupled to conductor 22*c*, the manubrium electrode 39*a* coupled to the conductor 40*a* and the right leg or ground electrode 39*c* coupled to the conductor 40*c* and relates those to the inputs 44*a*, 44*b* and 44*d* to the electrocardiograph 48.

Figure 15:
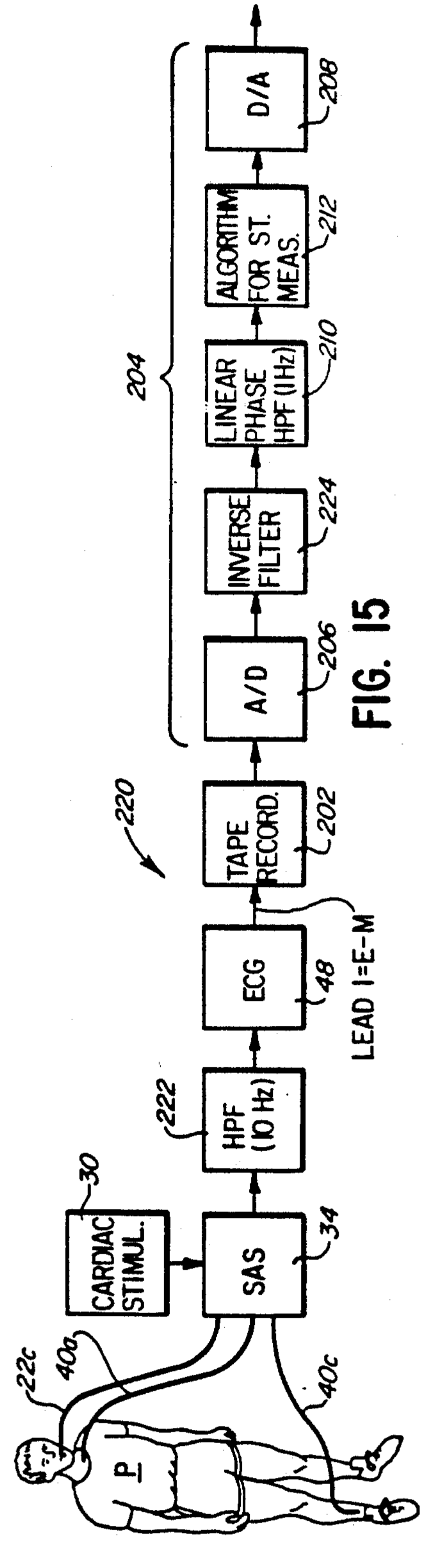
FIG. 15 is a block diagram of an alternate system for detecting posterior ischemia where the subject's heart is being paced.

The system 210 as illustrated does not provide any filtering between the artifact suppressor 34 and the electrocardiogram 48. FIG. 15 is an alternate system 220 including the elements of the system 210 but also providing an analog high pass filter 222 at the output of the transient suppressor 34 and a corresponding digital inverse filter 224 implemented as part of the control program for the computer 204. The high pass filter 222 can be implemented with a resistor and a capacitor.

The system 220 has the advantage that signals from the artifact suppressor 34 are filtered in the high pass 10 Hertz filter 222. As a result, the input signals to the electrocardiograph 48, due to the low frequency filtering of the element 222 will not exceed the dynamic input range of that unit. After the detected signals have been digitized in the analog digital converter 206 an inverse filter 224, implemented as a digital filter in the computer system 204 can be used to reverse the effects of the high pass filter 222. Output from the inverse filter 224, in digital form, can be provided to the linear phase high pass filter 210 for removable of low frequency baseline wander.

The implementation of the inverse filter 224 can be carried out by a well-known process previously described in an article entitled "*Computer Equalization Of Low-Frequency Components In A Tape-Recorded Electrocardiographic Signals*" by Arzbaecher, Woolsey and Brody IEEE Transactions Biomed Eng, pages 252–257, 1967.

The R wave detector consists of a nonrecursive median filter followed by signal subtraction, squaring, thresholding, and blanking processes. The software searches for four consecutive beats that satisfy a regularity criteria as determined by the instantaneous heart rate or RR interval and its relation to a user-specified value for the pacing rate. A tolerance value of 25 ms for the RR interval regularity was used. For ST segment measurements, the baseline fiducial point was taken as the data point 60 ms before and the ST fiducial point as the data point 80 ms after the temporal location of the peak of the captured R wave. ST segment measurements as previously described were performed on the preprocessed ECG signal.

Different methods of ST segment analysis can be used. The first method, single point, was discussed previously. The second and third methods (average and weighted average) arrive at a statistically more accurate measurement by spreading the measurement over a 16-ms observation window (either uniformly weighted, or non-uniformly but symmetrically weighted) centered over the baseline and ST fiducial points. The fourth and fifth methods (linear least-squares and parabolic least-squares) take into account the morphology of he ST segment which is assumed to be either a straight or a parabolic segment. In all methods, ST slope is calculated over a 40-ms window centered over the ST fiducial point within the ST segment.

Attached hereto as an Appendix is a listing of a group of computer programs for implementing the linear phase high pass filter 210, the measurement process for the ST segment measurement 212 and the inverse filter 224. These programs are written in "C", a well-known programming language. In the enclosed Attachment A, the program Filter.C implements the linear phase high pass filter (1 Hertz) element 210. The program Median.C performs the above-noted median filtering on the digitized input data. The programs Filter.C and Median.C implement the above-noted R wave detection. In accordance with the present invention, a single nonrecursive filter with window size 25 was used.

The group of programs named Inverse.C, Cut.C, Paste.C and Equal.C taken together implement the inverse filter element 224. The program ST-SEG-P.C implements the automatic measurement of the ST segment for the purposes of determining the presence or absence of the posterior ischemia.

Additional details of the implementation of the elements 210, 212 and 224, as well as these various alternative forms of analysis, are described in a dissertation entitled *Computer Analysis of The Electrocardiogram For Detection of Myocardial Ischemia During Transesophageal Atrial Pacino Stress* written by H. Jadvar and published August, 1988 by The University of Michigan. That dissertation is hereby incorporated herein by reference.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

APPENDIX 27-1

FILTER.C 5-02-88 4:29pm Page 1

```
/**********************************************************************

      Preprocessor for surface or esophageal ECG during
            Transesophageal Atrial Pacing Stress

  Usage: filter infile outfile filter_no r_B_A_code(0/1) w_B_A_code(0/1)
         <filter_no.    1        dc_filter, HPF (1 Hz)
                        2        HPF (30 Hz)
                        3        squaring, thresholding, blanking (300 ms) pace
                        4        squaring, thresholding, blanking (200 ms) qrs
                        5        gen squaring, thresholding, blanking (200 ms) pace,qrs
                        6        BPF (5-15 Hz)
                        7        5-point Hanning filter
                        8        5-point derivative
                        9        beginning and end of file w/ -2047
                        10       3-point Smoothing (Hanning) Filter
                        11       dc filter
                        12       inversion   >
       B = binary, A = ASCII

  Author: Hossein Jadvar
  Date:   January 1988
**********************************************************************/

#include <stdio.h>
#include <stdlib.h>
#include <math.h>

#define MAXNUM      32257    /* 32257 129 s max, int data at 250 Hz*/
#define PTSSCT      512      /* 512 of input data at a time       */
#define FILLEN      511      /* length of filter, even sym, odd N */
#define FFTLEN      1024     /* 1024 length of FFT                */
#define BASE        2
#define PI          (double)(4. * atan(1.))
#define SAMPLE_FREQ 250
#define square(x)   x * x

/* declaration of global variables                          */

int    num_points,      /* number of time data points read (adjusted)*/
       num_of_sects;    /* number of data sections (section=PTSSCT)  */
int    data[MAXNUM+FILLEN], data_filt[MAXNUM+FILLEN], thrsh[200];
int    temp1[MAXNUM];
double data_real[FFTLEN], data_imag[FFTLEN],temp_2[FFTLEN],
       h_real[FFTLEN], h_imag[FFTLEN];

/**********************************************************************/
main(argc,argv)
int argc;
char *argv[];
{
   int   i,sign,sect_num,code,r_filecode,w_filecode,
         filt_no,band_reject,no_coeff,window,thresh,blank;

   float lo_cut, hi_cut, f1, f2, fn, div_fact;

   if (argc != 6)
      {
      printf("Wrong usage: filter infile outfile filter_no r_B_A_code (0/1) w_B_A_code(0/1)\n");
      printf("filter_no: 1    dc_filter, HPF (1 Hz)\n");
```

FILTER.C 5-02-88 4:29pm Page 2

```
      printf("             2    HPF (30 Hz)\n");
      printf("             3    squaring, thresholding, blanking (300 ms) pace\n");
      printf("             4    squaring, thresholding, blanking (200 ms) qrs\n");
      printf("             5    gen squaring, thresholding, blanking (200 ms) pace,qrs\n");
      printf("             6    BPF (5-15 Hz)\n");
      printf("             7    5-point Hanning filter\n");
      printf("             8    5-point derivative\n");
      printf("             9    beginning and end of file w/ -2047\n");
      printf("             10   3-point smoothing (Hanning) filter\n");
      printf("             11   dc filter\n");
      printf("             12   inversion\n");
      printf("B = binary file, A = ASCII file\n");
      exit(1);
      }

   filt_no = atoi(argv[3]);
   r_filecode = atoi(argv[4]);
   w_filecode = atoi(argv[5]);
/* initialize();      */
   read_data(argv[1],r_filecode);
   fn = (float) SAMPLE_FREQ/2.;
   switch(filt_no) {
      case 1 :
         /* Case for dc filtering and HPF (1 Hz) bain stablization */

         printf("\ndc filtering...\n");
         dc_filter();
         f1=1; f2=125;
         lo_cut=f1/fn;
         hi_cut=f2/fn;
         band_reject=0;
         no_coeff=255;
         window=1;
         printf("\nDesigning High-Pass Filter fc=1 Hz...\n");
         filt(lo_cut,hi_cut,band_reject,no_coeff,window);
         sign=-1;
         fft(sign);
         break;

      case 2 :
         /* Case HPF (30 Hz) for Pace */

         f1=30; f2=125;
         lo_cut=f1/fn;
         hi_cut=f2/fn;
         band_reject=0;
         no_coeff=255;
         window=1;
         printf("\nDesigning High-Pass Filter fc=30 Hz...\n");
         filt(lo_cut,hi_cut,band_reject,no_coeff,window);
         sign=-1;
         fft(sign);
         break;

      case 3 :
         /* Case for squaring, thresholding, and blanking (pace) */

         div_fact=120.;
         printf("\nSquaring...division factor=%d. (pace)\n",(int)div_fact);
         squ(div_fact);
```

```
FILTER.C    5-02-88 4:29pm                                        Page 3
        thresh=20; blank=75;
        printf("\nThresholding...thresh factor=%d, blank period=%d ms. (pace)\n",
                thresh,(int)((float)blank*1000./(float)SAMPLE_FREQ));
        threshold_2(thresh,blank);
        code=1;
        write_out(argv[2],w_filecode,code);
        exit(0);

    case 4 :
        /* Case for squaring, thresholding, and blanking (QRS) */

        div_fact=128.;
        printf("\nSquaring...division factor=%d. (qrs)\n",(int)div_fact);
        squ(div_fact);
        thresh=20; blank=50;
        printf("\nThresholding...thresh factor=%d, blank period=%d ms. (qrs)\n",
                thresh,(int)((float)blank*1000./(float)SAMPLE_FREQ));
        threshold_2(thresh,blank);
        code=1;
        write_out(argv[2],w_filecode,code);
        exit(0);

    case 5 :
        /* Case for gen squaring, thresholding, and blanking (pace,QRS) */

        div_fact=128.;
        printf("\nSquaring...division factor=%d. (pace,qrs)\n",(int)div_fact);
        squ(div_fact);
        blank=50;
        threshold_1(blank);
        code=1;
        write_out(argv[2],w_filecode,code);
        exit(0);

    case 6 :
        /* Case for BPF (5-15 Hz) for QRS */

        printf("\nDesigning Bandpass Filter...fc1=5 Hz, fc2=15 Hz\n");
        f1=5; f2=15;
        lo_cut=f1/fn;
        hi_cut=f2/fn;
        band_reject=0;
        no_coeff=255;
        window=1;
        filt(lo_cut,hi_cut,band_reject,no_coeff,window);
        sign=-1;
        fft(sign);
        break;

    case 7 :
        /* Case for 5-point hanning filter */

        printf("\nFive-point Hanning filter...\n");
        han_derv(0.125,0.25,0.25,0.25,0.125);
        code=1;
        write_out(argv[2],w_filecode,code);
        exit(0);

    case 8 :
        /* Case for taking 5-point derivatve */
```

```
FILTER.C    5-02-88 4:29pm                                        Page 4
        printf("\nFive-point derivatve...\n");
        han_derv(-0.2,-0.1,0.,0.1,0.2);
        code=1;
        write_out(argv[2],w_filecode,code);
        exit(0);

    case 9 :
        /* Case for marking the beginning and the end of input data file */

        data[0]=data[num_points-1]=-2047.;
        printf("\nStart and end of input file marked with -2047...\n",argv[2]);
        code=1;
        write_out(argv[2],w_filecode,code);
        exit(0);

    case 10 :
        /* Case for smoothing the data (3-point Hanning filter) */

        printf("\nSmoothing the data (3-point Hanning)...\n");
        han_derv(0.,0.25,0.5,0.25,0.);
        code=1;
        write_out(argv[2],w_filecode,code);
        exit(0);

    case 11 :
        /* Case for do filtering the data... */

        printf("\ndo filtering...\n");
        do_filter();
        code=1;
        write_out(argv[2],w_filecode,code);
        exit(0);

    case 12 :
        /* Case for inverting a signal */

        printf("\nInverting the signal...\n");
        code=2;
        write_out(argv[2],w_filecode,code);
        exit(0);

    default:
        printf("\nCase is not assigned. Use 1 to 12.\n");
        exit(0);
            }
    h_coeff();

    printf("\n********* Filtering starts (freq res = %.3f Hz)*********\n",
        (float)SAMPLE_FREQ/(float)FFTLEN);

    for (sect_num=0; sect_num < num_of_sects; sect_num+=2)
        {
        if(num_of_sects - sect_num == 1)
          printf("\nSECTION NO. %d.............%d SECTIONS LEFT.\n",
                (sect_num+1),(num_of_sects - sect_num - 1));
        else
          printf("\nSECTION NOs. %d & %d.......%d SECTION(S) LEFT.\n",
                (sect_num+1),(sect_num+2),(num_of_sects - sect_num - 2));
        printf("\nSectioning and padding the data...\n");
```

```
FILTER.C   5-02-88 4:29pm                                              Page 5
      section_pad(sect_num);
 /*
      printf("\n");
      for (i=0; i<FFTLEN; i++) {
      printf("%d %f %f\n", i, data_real[i], data_imag[i]); }
 */
      printf("\nForward Fourier Transform...\n");
      sign=-1;
      fft(sign);
 /*
      for (i=0; i < FFTLEN; i++) {
      printf("%d %f %f\n", i,data_real[i], data_imag[i]); }
 */
      printf("\nFiltering ...\n");
      convolve();

      printf("\nInverse Fourier Transform...\n");
      sign=1;
      fft(sign);
/*
      for (i=0; i < FFTLEN; i++) {
      printf("%d %f %f\n", i, data_real[i], data_imag[i]); }
      printf("\n");
*/
      printf("\nOverlap and Add...\n");
      ovlp_add(sect_num);
/*
      for (i=0; i < (num_points+PTSSCT); i++) {
      printf("%d %f\n",i,data_filt[i]);}
*/
      }

   printf("\n*************Filtering completed***************\n");

   assign();

   code = 0;
   write_out(argv[2],w_filecode,code);
}
/*******************************************************************/
h_coeff()
{
   int i;
   for(i=0; i<FFTLEN; i++)          {
      h_real[i]=data_real[i];
      h_imag[i]=data_imag[i];
      data_real[i]=data_imag[i]=0; }
}
/*******************************************************************/
squ(factor)
float factor;
{
   int i;
   float temp;

   for(i=0; i<num_points; i++) {
      temp = square((float)data[i])/factor;
/*    printf("%d\t%d\t%f\n",i,data[i],temp); */
      data[i] = (int)temp;
                        }
```

```
FILTER.C   5-02-88 4:29pm                                              Page 6
}
/*******************************************************************/
threshold_1(m)
int m;
{
   int i,j,h,index,th_lvl;
   long sum;

   j=h=0;
   sum=0;
   for(i=0; i<num_points; i++) {
     if(h <= abs(data[i])) h = abs(data[i]);
     else {
        thrsh[j] = i;
        h=0;
        j++;    }                }

   for(i=0; i<j; i++) {
     index = thrsh[i];
     sum += (long)(abs(data[index])); }

   th_lvl= (int)(sum / (long)j);
   printf("\nThresholding...(general)\n");
   printf("Threshold level is %d (%ld divided by %d).\n",th_lvl,sum, j);
   for(i=0; i<num_points; i++) {
     if(abs(data[i]) > th_lvl)  {
        data[i] = 2047;
        for(j=i+1; j<i+m; j++)
            data[j]=0;           }
     else data[i]=0;           }
}
/*******************************************************************/
threshold_2(th,m)
int th,m;
{
   int i,j,h,min,max;

   min=2047; max=-2047; /* th=threshold factor, blanking period=m*4 ms */
   for (i=0; i<num_points; i++) {
     if (data[i] < min) min = data[i];
     if (data[i] > max) max = data[i]; }
   h = min + (max - min)/th;
   /* printf("\nmin=%d max=%d h=%d th=%d m=%d\n\n",min,max,h,th,m); */

   for (i=0; i<num_points; i++) {
     if (data[i]>h) {
         data[i]=2047;
         for (j=i+1; j<i+m; j++)
             data[j]=0;
                }
     else data[i]=0;            }
}
/*******************************************************************/
initialise()
{
   int i;
   printf("\nInitializing the data arrays...\n");
   for (i=0; i < (MAXNUM + FILLEN); i++)
       {
       data[i] = data_filt[i] = 0;
```

```
FILTER.C    5-02-88 4:29pm                                    Page 7
        }
   }
/*********************************************************************/
read_data(infile,frcode)
int  frcode;
char *infile;
{
   int i, temp, check;
   FILE *fpi;

   if (frcode == 1)   {
       if ((fpi=fopen(infile, "r")) == NULL)
       {
         printf("error -> unable to open input ascii file %s\n",infile);
         exit(1);
       }
       printf("\nReading the input ascii file %s...\n",infile);
       for(i=0; (fscanf(fpi,"%d", &temp) != EOF) && (i < MAXNUM); i++)
       {
         data[i] = temp;
/*       printf("data[%d] = %d\n",i,data[i]);  */
       }
       num_points = i; }

   else {
       if ((fpi=fopen(infile, "rb")) == NULL) {
         printf("error -> unable to open input binary file %s\n",infile);
         exit(1); }

       printf("\nReading the input binary file %s...\n",infile);
       for(i=0; i<MAXNUM && !feof(fpi); i++)
         data[i]=(int)getw(fpi);
       num_points=i; }

   if(num_points<PTSSCT) { num_of_scts=1; goto close; }

   if((num_points % PTSSCT) !=0) {
       num_points = num_points - (num_points % PTSSCT); }
   num_of_scts = Num_points / PTSSCT;
   printf("\nData input completed. %d data points read.\n",num_points);

close: check=fclose(fpi);
       if (check != 0) {
          printf("error -> unable to close input file %s\n",infile);
          exit(1);      }
}
/*********************************************************************/
section_pad(m)
int m;
{
   int i;
   for(i=0; i < PTSSCT; i++)    {
        data_real[i] = (double) data[i+PTSSCT*m];
      if(num_of_scts - m != 1)
        data_imag[i] = (double) data[i+PTSSCT*(m+1)];
      else data_imag[i] = 0.;  }
   for(i=PTSSCT; i<FFTLEN; i++)
      data_real[i] = data_imag[i] = 0.;
}
/*********************************************************************/
```

```
FILTER.C    5-02-88 4:29pm                                    Page 8
fft(sign)
int sign;
{
   int    i,j,k,m,
          power,
          distance,
          step,
          stage;

   double temp_x,temp_y,w_x,w_y,
          const,
          theta;

   power = 0; j = 1;
   do {
      j *= 2;
      power++;
      } while (j < FFTLEN);

   for (i = 0; i < FFTLEN; i++)
       {
       j = 0; m = FFTLEN;
       for (k = 0; k < power; k++)
          {
          m /= 2;
          if ((i >> k) & BASE)  j += m;
          }
      if (i < j)
          {
          temp_x       = data_real[j];
          temp_y       = data_imag[j];
          data_real[j] = data_real[i];
          data_imag[j] = data_imag[i];
          data_real[i] = temp_x      ;
          data_imag[i] = temp_y      ;
          }
      }

   for (stage=0; stage < power; stage++)
      {
      distance = pow(2.,(double)stage);
      step     = 2 * distance;
      for (k = 0; k < distance; k++)
          {
          theta = ((double)(sign * k)) * PI / (double) distance;
          w_x = cos(theta);
          w_y = sin(theta);
          for (i = k; i < FFTLEN; i += step)
              {
              j = i + distance;
              temp_x = w_x * data_real[j] - w_y * data_imag[j];
              temp_y = w_x * data_imag[j] + w_y * data_real[j];
              data_real[j] = data_real[i] - temp_x;
              data_imag[j] = data_imag[i] - temp_y;
              data_real[i] = data_real[i] + temp_x;
              data_imag[i] = data_imag[i] + temp_y;
              }
          }
      }
```

```
FILTER.C    5-02-89 4:29pm                                    Page 9
    const = (sign == -1) ? 1. : (1./FFTLEN) ;

    for (i = 0; i < FFTLEN; i++)
        {
        data_real[i] *= const;
        data_imag[i] *= const;
        }
}
/*****************************************************************/
dc_filter()
{
  int     i;
  double sum, mean;

  sum = 0.;

  for (i=0; i < num_points; i++) {
       sum += (double)data[i];   }
  mean = sum / (double) num_points;
  printf("mean (dc value) = %f\n", mean);
  for (i=0; i < num_points; i++) {
       data[i] -= (int)mean;  }
}
/*****************************************************************/
han_derv(q0,q1,q2,q3,q4)
float q0,q1,q2,q3,q4;
{
  int i;
  float temp;

/*printf("q0=%f\tq1=%f\tq2=%f\tq3=%f\tq4=%f\n",q0,q1,q2,q3,q4);*/
  for(i=2; i<num_points-2; i++)
      temp1[i]=(int)(((float)data[i-2])*q0+((float)data[i-1])*q1+
                ((float)data[i])*q2+((float)data[i+1])*q3+((float)data[i+2])*q4);

  for(i=2; i<num_points-2; i++)
      data[i] = temp1[i];
}
/*****************************************************************/
assign()
{
  int i;
  for (i=0; i < (num_points + FILLEN); i++)
      data[i] = data_filt[i];
}
/*****************************************************************/
convolve()
{
   int    i;
   double temp_real, temp_imag;

   for (i=0; i < FFTLEN; i++)
       {
       temp_real = data_real[i] * h_real[i] - data_imag[i] * h_imag[i];
       temp_imag = data_real[i] * h_imag[i] + data_imag[i] * h_real[i];
       data_real[i] = temp_real;
       data_imag[i] = temp_imag;
       }
}
/*****************************************************************/
```

```
FILTER.C    5-02-89 4:29pm                                    Page 10
ovlp_add(m)
int m;
{
   int i;
   for (i=0; i < (FILLEN + PTSSCT - 1); i++)       {
        data_filt[i+PTSSCT*m] += (int) data_real[i];
      if((num_of_scts - m) != 1)
        data_filt[i+PTSSCT*(m+1)] += (int) data_imag[i]; }
}
/*****************************************************************/
write_out(outfile,fwcode,c)
char *outfile;
int  fwcode,c;
{
   int  i,check,temp_out;
   FILE *fpo;

   if(fwcode == 0) {
      if((fpo = fopen(outfile, "wb")) == NULL)
      {
        printf("error -> unable to open binary output file %s\n",outfile);
        exit(1);
      }
      printf("\nWriting the output into binary file %s...\n",outfile);
      for (i=0; i < num_points; i++)           {
        if (c==0) data_filt[i] = data[i+(FILLEN-1)/2];
        if (c==1) data_filt[i] = data[i];
        if (c==2) data_filt[i] = -data[i];
        if (data_filt[i] > 2047) data_filt[i] = 2047; }
      fwrite(data_filt,sizeof(int),num_points,fpo);
              }
   else {
      if((fpo = fopen(outfile, "w")) == NULL)
      {
        printf("error -> unable to open ascii output file %s\n",outfile);
        exit(1);
      }
      printf("\nWriting the output into ascii file %s...\n",outfile);
      for (i=0; i < num_points; i++) {
        if (c==0) temp_out = data[i+(FILLEN-1)/2];
        if (c==1) temp_out = data[i];
        if (c==2) temp_out = -data[i];
        if (temp_out > 2047) temp_out = 2047;
        fprintf(fpo, "%6d%c", temp_out,(i % 10 == 9 ? '\n' : ' '));
                                           }
        }

   check=fclose(fpo);
   if (check != 0)
      {
      printf("error -> unable to close output file %s\n",outfile);
      exit(1);
      }
}
/*****************************************************************/
filt(v1,v2,br,p,wnd)
double v1,v2;
int    br,p,wnd;
{
      int i;
```

```
FILTRA.C   5-02-88 4:39pm                                   Page 11

     temp_2[0] = v2 - v1;
     if (br == 1) temp_2[0] = 1 - temp_2[0];

     for (i=1; i<(p+1); i++)
        {
        temp_2[i] = (sin(v2*i*PI))/(i*PI) - (sin(v1*i*PI))/(i*PI);
        if (br == 1) {
           temp_2[i] = -temp_2[i]; }
        }
    if (wnd == 1) {
       for (i=0; i<(p+1); i++) {
          temp_2[i] = temp_2[i] * (0.54 + 0.46 * (cos(i*PI/p)));}
              }
    for (i=0; i<(p+1); i++)
        {
        data_real[i] = temp_2[p-i];
        data_imag[i] = 0.;
        }
    for (i=1; i<(p+1); i++)
        {
        data_real[p+i] = data_real[p-i];
        data_imag[p+i] = 0.;
        }
    for (i=(2*p+1); i<FFTLEN; i++)
        {
        data_real[i] = data_imag[i] = 0.;
        }
```

```
MEDIAN.C    4-17-88 11:52pm                                              Page 1
/*****************************************************************************
 This program median filters (nonrecursive) its input.

Usage: median infile outfile windowsize filecode(0/1) r_B_A w_B_A windowsize: size of the median filter data window; must be odd.
        filecode: 0 for straight filtered data, 1 for input - output,
        r_B_A: 0 for binary input file, 1 for ascii
        w_B_A: 0 for binary output file, 1 for ascii Author: Hossein Jadvar
 Date:   Jan 1988
*****************************************************************************/
#include <stdio.h>
#include <stdlib.h>

#define MAXNUM          32767  /* max 32767 (64KB) no of int data (2 bytes) */ int     num_points,r_filecode,w_filecode;
int     data_in[MAXNUM],data_out[MAXNUM],data_temp[MAXNUM];

main(argc,argv)
int argc;
char *argv[];
{
       int      i,wss,code;

if (argc != 7) {
         printf("\nUsage: median infile outfile wndsze fcode(0/1) r_B_A w_B_A\n");
         printf("       wndsze: size (odd) of the median filter data window\n");
         printf("       fcode: 0 for straight filtered data, 1 for input - output\n");
         printf("       r_B_A: 0 for binary input file, 1 for ascii\n");
         printf("       w_B_A: 0 for binary output file, 1 for ascii\n");
         exit(1);       } r_filecode = atoi(argv[5]);
       w_filecode = atoi(argv[6]);

read_in(argv[1],r_filecode);

wss = atoi(argv[3]);
       printf("\nMedian filtering...window size is %d.\n",wss);
       median(wss);

code = atoi(argv[4]);
       write_out(argv[2],w_filecode,code);

/*     for(i=0; i<MAXNUM; i++) {
         printf("%d\t%d\t%d\n",i,data_in[i],data_out[i]);}
*/
}
/*************************************************************************/
median(n)
int n;
{
       int *r,*p,*q,i,j,k,l;

p=data_out; q=data_in; r=data_temp;
       k=(n-1)/2;
```

```
MEDIAN.C    4-17-88 11:52pm                                              Page 2
       for(i=0; i<k; i++)
         *(p+i)=*(q+i);

for(i=0; i<num_points; i++)
         *(r+i)=0;

for(i=0; i<n; i++)
         for(j=i+1; j<n; j++)
         {
           if(*(q+i) > *(q+j))
                *(r+i)=*(r+i) + 1;
           else
                *(r+j)=*(r+j) + 1;
         } for(i=0; i<n; i++)
         if(*(r+i)==k) *(p+k)=*(q+i);

for(i=k+1; i<num_points-k; i++)
         {
           l = i-(k+1);
           for(j=1; j<n; j++)
                {
                     if(*(q+l) <= *(q+l+j))
                          *(r+l+j) = *(r+l+j) - 1;
                     if(*(q+l+j) > *(q+l+n))
                          *(r+l+j) = *(r+l+j) + 1;
                     else
                          *(r+l+n) = *(r+l+n) + 1;
                }
                for(j=i-k; j<i-k+n; j++)
                     if(*(r+j)==k) *(p+i)=*(q+j);
         }
      for(i=num_points-k; i<num_points; i++)
         *(p+i)=*(q+i);
}
/*************************************************************************/
read_in(infile,frcode)
int  frcode;
char *infile;
{
   int i, temp, check;
   FILE *fpi;

if (frcode == 1)   {
      if ((fpi=fopen(infile, "r")) == NULL)
      {
        printf("error -> unable to open input ascii file %s\n",infile);
        exit(1);
      }
      printf("\nReading the input ascii file %s...\n",infile);
      for(i=0; (fscanf(fpi,"%d", &temp) != EOF) && (i < MAXNUM); i++)
      {
        data_in[i] = temp;
/*      printf("data_in[%d] = %d\n",i,data_in[i]);  */
      }
      num_points = i; } else {
      if ((fpi=fopen(infile, "rb")) == NULL) {
```

```
MEDIAN.C    4-17-88 11:52pm                                          Page 5
         printf("error -> unable to open input binary file %s\n",infile);
         exit(1); }

    printf("\nReading the input binary file %s...\n",infile);
    for(i=0; i<MAXNUM && !feof(fpi); i++)
       data_in[i]=(int)getw(fpi);
    num_points=i; }

    printf("\nData input completed. %d data points read.\n",num_points);

    check=fclose(fpi);
    if (check != 0) {
       printf("error -> unable to close input file\n");
       exit(1); }
}
/*********************************************************************/
write_out(outfile,fwcode,c)
char *outfile;
int  fwcode,c;
{
   int  i,check,temp_out;
   FILE *fpo;

   if (c == 1) {
      for (i=0; i<num_points; i++)
      data_out[i] = data_in[i]-data_out[i];
                }

   if(fwcode == 0) {
      if((fpo = fopen(outfile, "wb")) == NULL)
      {
        printf("error -> unable to open binary output file %s\n",outfile);
        exit(1);
      }
      printf("\nWriting the output into binary file %s...code=%d\n",outfile,c);
      fwrite(data_out,sizeof(int),num_points,fpo);
                  }
   else {
      if((fpo = fopen(outfile, "w")) == NULL)
      {
        printf("error -> unable to open ascii output file %s\n",outfile);
        exit(1);
      }
      printf("\nWriting the output into ascii file %s...code=%d\n",outfile,c);
      for (i=0; i < num_points; i++)
        fprintf(fpo, "%6d%c",data_out[i],(i % 10 == 9 ? '\n' : ' '));
        }

   check=fclose(fpo);
   if (check != 0)
      {
      printf("error -> unable to close output file %s\n",outfile);
      exit(1);
      }
}
```

```
ST_SEG_P.C   5-04-88 4:11pm                                              Page 1
/*************************************************************************
 This program determines sustained capture and then calculates beat-by-beat
 and algebraic mean (over 5 beats) ST level and slope, and R wave amplitude.
 Five different computer methods (single-point, 16-ms average, 16-ms weighted
 average, 16-ms parabolic least-squares, and 16-ms linear least-squares)
 are employed in the ST level measurements.  The ST slope measurements employ
 calculation of direct line between R+60 ms (J point), and R+100 ms (STend
 point) as well as linear LS and parabolic LS between the same two points.
 The ST fiducial point is centered at R+80 ms in the ST segment.
 The baseline fiducial point is centered at R-60 ms in the PR segment.
 The additional ST level shift is calculated if rest ECG is available.
 The program can handle stress ECGs whether or not they are contaminated
 with pace artifacts (such as leads V1, II, V5, etc.) or not contaminated
 with pace artifacts (such as leads EVM and CM5). Other features calculated
 and reported are instantaneous RR-interval and heart rate, pace-R interval
 (indirect indicator of AV delay), and sinus node recovery time upon loss of
 sustained capture.

 Usage: st_seg_p 1 <pace_r> <qrstrgfile> <datafile> <rstatfile> <outtrgfile>
                   <r_B_A> <w_B_A>
        [For stress ECG with no pace artifacts]

        st_seg_p 2 <p<r?> <postrgfile> <qrstrgfile> <datafile> <rstatfile>
                   <outtrgfile> <r_B_A> <w_B_A>
        [For stress ECG contaminated with pace artifacts]

        <pace_r>: pacing rate when there are no artifacts
        <p<r?>: 2 for when pace artf > R and 1 when pace artf < R
        <r_B_A>: Read in binary (0) or ascii format (1)
        <w_B_A>: Write in binary (0) or ascii format (1)

 Author: Hossein Jadvar
 Date:   January 1988
*************************************************************************/
#include <stdio.h>
#include <stdlib.h>
#include <math.h>

#define MAXNUM        32767  /* max 131 s int data at 250 Hz */
#define SAMPLE_FREQ   250    /* in Hz */
#define FIT           2      /* 2*FIT+1 pts fit for linear and parab STlvl */
#define GAIN          10     /* 10 mm/mv */
#define BASE          (60 * SAMPLE_FREQ /1000)     /* 60 ms before R */
#define ST            (80 * SAMPLE_FREQ / 1000)    /* 80 ms after R */
#define J             (60 * SAMPLE_FREQ / 1000)    /* 60 ms after R */
#define CAP           5      /* post or pre ST or BASE delta */
#define PACE_WNDW     20     /* +- 80 ms at 250 Hz window for finding peak*/
#define QRS_WNDW      15     /* +- 60 ms at 250 Hz window for finding peak*/
#define LOW_RR        0.95   /* lower bound coeff for inst RR or HR, capt */
#define HIGH_RR       1.05   /* upper bound coeff for inst RR or HR, capt */
#define LOW_PR        0.95   /* lower bound coeff for PR interval */
#define HIGH_PR       1.05   /* upper bound coeff for PR interval */
#define DELTA_RR      0.025  /* +-limit (s) for RR interval during capture */
#define DELTA_HR      10      /* +-limit for HR during capture */
#define ECG_G         1000.  /* gain of the ECG machine */
#define TAPE_G        0.5    /* tape recorder gain */
#define NUM           5.     /* no of average beats for ST mean */
#define AD_V_RNG      10000. /* 10 V, i.e. +-5 V AD range */
#define AD_C_RNG      4096.  /* 12 bit resolution */
#define sqr(x)        x * x
```

```
ST_SEG_P.C   5-04-88 4:11pm                                              Page 2

int     num_points,tot_r_cap_num,r_cap_num,linear_code,st_avg_num,
        np_p_code,r_p_code,r_filecode,w_filecode;
int     pace[MAXNUM],qrs[MAXNUM],data_org[MAXNUM],data[MAXNUM],trg_loc[MAXNUM],
        pace_loc[400],qrs_loc[400],qrs_pk_loc[400],pace_pk_loc[400],
        r_cap_pk_loc[400],hr[400],
        r_cap_num_div[25],r_cap_num_reset[25],cap_beat[200],st_avg_bt[40];
int     pace_num,qrs_num,prcode,div,
        sinus_code,num_of_sinus,sinus_bt_no[25];
float   pr,rr[400],sinus_rec[25],rest_st[5],
        st_lvl_avg_p[40],st_lvl_avg_pal[40],st_lvl_avg_pw[40],
        st_lvl_avg_pr[40],st_slp_avg_paw[40],st_slp_avg_pr_l[40];
char    *mes;

main(argc,argv)
int argc;
char *argv[];
{
      int     i,file_code,type,ppm;
      float   pp;

      r_cap_num=tot_r_cap_num=sinus_code=num_of_sinus=div=st_avg_num=0;
      np_p_code=atoi(argv[1]);
      r_p_code=atoi(argv[2]);

      if(argc != 9 && argc != 10)   {
         printf("\nUsage:\n");
         printf("st_seg_p 1 p_rate qrstrg infile st_rst_f outtrg r_B_A w_B_A\n");
         printf("st_seg_p 2 p>r?(2/1) pacetrg qrstrg infile st_rst_f outtrg r_B_A
                 w_B_A\n");
         exit(1);                    }

      if((np_p_code != 1) && (np_p_code != 2)) {
         printf("\nUse either code 1 for non-spiked or 2 for spiked stress ECG.\n");
         exit(1);    }
      else if(np_p_code == 2 && r_p_code != 1 && r_p_code != 2) {
         printf("\nUse r_p_code of 1 for p<r or 2 for p>r w/ np_p_code=2\n");
         exit(1);    }

      if(np_p_code==1)    {
         if(argc != 9) {
           printf("\nUsage: st_seg_p 1 p_rate qrstrg in_f strst_f outtrg r_B_A(0/1)
                  w_B_A(0/1)\n");
           exit(1);      }
         else {
           r_filecode = atoi(argv[7]);
           w_filecode = atoi(argv[8]);
           for(file_code=3; file_code<argc-3; file_code++) {
              if(r_filecode == 0) {
                printf("\nReading binary file %s...\n",argv[file_code]);
                read_b_data(argv[file_code],file_code-1); }
              else {
                printf("\nReading ascii file %s...\n",argv[file_code]);
                read_data(argv[file_code],file_code-1);          } } } }

      if(np_p_code==2)    {
         if(argc != 10) {
           printf("\nUsage: st_seg_p 2 p>r?(2/1) pacetrg qrstrg in_f strst_f
                  outtrg r_B_A(0/1) w_B_A(0/1)\n");
           exit(1);    }
```

```
ST_RNG_P.C    5-04-88 4:11pm                                        Page 3
      else {
        r_filecode = atoi(argv[8]);
        v_filecode = atoi(argv[9]);
        for(file_code=2; file_code<argc-4; file_code++) {
          if(r_filecode == 0) {
            printf("\nReading binary file %s...\n",argv[file_code+1]);
            read_b_data(argv[file_code+1],file_code-1); }
          else {
            printf("\nReading ascii file %s...\n",argv[file_code+1]);
            read_data(argv[file_code+1],file_code-1);        } } } }

/* Mark the beginning and end of data in the trig file */
/*    trg_loc[0] = trg_loc[num_points-1] = -2047; */

/* Smooth the data for pace and qrs peak detection and ST measurements;
   the R amplitude measurements use the original data */
    if(np_p_code==2) {
      printf("\nSmoothing...(3 pt Hanning filter)...\n");
      hann(0.,0.25,0.5,0.25,0.); }
    else {
      printf("\nSmoothing...(5 pt Hanning filter)...\n");
      hann(0.125,0.25,0.25,0.25,0.125); }

/* Find and mark the location of peak of qrs & pace artifacts detected */
    if(np_p_code==2) {          /* processing spike contaminated stress ECG */
      if(r_p_code==2) {         /* pace artf >= qrs complex */
        pace_pk_find_lg();
        qrs_pk_find_sm();  }
      else            {         /* pace artf < qrs_complex */
        qrs_pk_find_lg();
        pace_pk_find_sm(); }  }
    else                        /* processing nonspike stress ECG */
      qrs_pk_find_lg();

/* Report general info about the input data */
    printf("\nTotal number of points in the record = %d\n",num_points);
    printf("\nTotal record length = %.3f seconds\n",((float)
            num_points/(float)SAMPLE_FREQ));
    printf("\nTotal no of QRS complexes detected = %d\n",qrs_num);
    if(np_p_code==2) {
      printf("\nTotal no of pace spikes detected = %d\n",pace_num);
      printf("\npace\tpace_f\tpace_pk\tpace_t(s)\tpace_rate(ppm)\n");
      printf("----------------------------------------------------\n");
      printf("1\t%d\t%d\t%.3f\t\t---\n",pace_loc[0],pace_pk_loc[0],
            ((float)pace_pk_loc[0]/(float)SAMPLE_FREQ));
      for(i=2; i<(pace_num+1); i++) {
        pp = (float)(pace_pk_loc[i-1]-pace_pk_loc[i-2])/(float)SAMPLE_FREQ;
        ppm = ceil((double)(60. / pp));
        printf("%d\t%d\t%d\t%.3f\t\t%d\n",i,pace_loc[i-1],pace_pk_loc[i-1],
              ((float)pace_pk_loc[i-1]/(float)SAMPLE_FREQ),ppm);
                                   }
                   }
    printf("\nbeat\tQRS_f\tQRS_pk\tQRS_t (s)\n");
    printf("----------------------------------------\n");
    for(i=1; i<(qrs_num+1); i++) {
      printf("%d\t%d\t%d\t%.3f\n",i,qrs_loc[i-1],qrs_pk_loc[i-1],
      ((float)qrs_pk_loc[i-1]/(float) SAMPLE_FREQ));
                                 }
/* Determine sustained capture */
    if(np_p_code==1)
```

```
ST_RNG_P.C    5-04-88 4:11pm                                        Page 4
      capture_np(r_p_code);
    else
      capture_p();

/* Take care of situation when there is no sinus node recovery in the record */
    if(div==0)                                {
      r_cap_num_div[div]=tot_r_cap_num;
      r_cap_num_reset[div+1]=0;               }

/* Take care of situation when record ends in sustained capture */
    if(cap_beat[tot_r_cap_num-1]==qrs_num)    {
      r_cap_num_div[div] = r_cap_num;
      r_cap_num_reset[div+1]=tot_r_cap_num;
      div++;                                  }

/* Report info about the captured beats */
    printf("\nTotal no of captured beats detected = %d\n\n",tot_r_cap_num);
    if(tot_r_cap_num==0) {
       printf("SUSTAINED 1:1 CAPTURE WAS NEVER DETECTED!\n");
       type=0;
       goto end;          }
    printf("Percent captured/total no of beats = %%%d\n",
          (100*tot_r_cap_num/qrs_num));
    if(div!=0) {
       printf("\nbeat\tsinus_rec(s)\n");
       printf("------------------------\n");
       for(i=0; i<num_of_sinus; i++)
          printf("%d\t%.3f\n",sinus_bt_no[i],sinus_rec[i]);
              }

/* Perform the ST measurements */
    for(type=1; type<6; type++) {
    printf("\n***********************************************************\n");
    printf("\nBASE PT-R-%d ms, STbegin=J-R+%d ms, ST-R+%d ms, STend-R+%d ms.\n",
          (BASE*1000/SAMPLE_FREQ),(J*1000/SAMPLE_FREQ),(ST*1000/SAMPLE_FREQ),
          ((ST+CAP)*1000/SAMPLE_FREQ));
    printf("\nThe ST resolution is +- %.3f mV (+- %f mV) wrt body potential.\n",
          (AD_V_RNG/AD_C_RNG/TAPE_G/ECG_G/2.),(AD_V_RNG/AD_C_RNG/TAPE_G/ECG_G/2.));
    printf("\nThe average resting ECG ST level is %.3f mV.\n",rest_st[type-1]);

      st_avg_num=0;
      if(type==1) printf("\nST_R MEASUREMENTS (SINGLE POINT)\n");
      if(type==2) printf("\nST_R MEASUREMENTS (AVERAGE)\n");
      if(type==3) printf("\nST_R MEASUREMENTS (WEIGHTED AVERAGE)\n");
      if(type==4) printf("\nST_R MEASUREMENTS (PARABOLIC LS)\n");
      if((type==1)||(type==2)||(type==3)||(type==4)) {
        linear_code = 0;
        printf("\no_bt\tstL\tst$\tstLa\tst$a\tr_ampl\n");
        printf("\t(mV)\t(mV/s)\t(mV)\t(mV/s)\t(mV)\n");          }
      if(type==5) {
        linear_code=1;
        printf("\nST_R MEASUREMENTS (LINEAR LS)\n");
        printf("\no_bt\tstL\tst$\tr_coeff\tstLa\tst$a\tr_ampl\n");
        printf("\t(mV)\t(mV/s)\t\t(mV)\t(mV/s)\t(mV)\n");
                  }
      printf("------------------------------------------------------------\n");
      if(div==0)  {
        st_r(type,div);
        continue; }
      for(i=0; i<div; i++) {
```

ST_BRG_P.C 5-04-88 4:11pm

```
            st_r(type,i);
            if(i!=(div-1))
              printf("----------Reset averaged ST measurements----------\n");
            else break;         }   }

end:  if(mp_p_code == 1) {
        if(w_filecode == 0)        {
          printf("\nWriting trig & feature locations into binary file %s...\n",
                argv[6]);
          write_b_data(argv[6]); }
        else {
          printf("\nWriting trig & feature locations into ascii file %s...\n",
                argv[6]);
          write_data(argv[6]); } }

      else {
        if(w_filecode == 0)        {
          printf("\nWriting trig & feature locations into binary file %s...\n",
                argv[7]);
          write_b_data(argv[7]); }
        else {
          printf("\nWriting trig & feature locations into ascii file %s...\n",
                argv[7]);
          write_data(argv[7]); } }

      if(type==0) goto stop;

      printf("\n*********** AVERAGE ST SUMMARY REPORT (OVER EVERY %d BEATS) ***********\n",
            (int)NOM);
      printf("*** ST LEVEL ***\n");
      printf("The ST resolution is +- %.3f mv (+- %f mV) wrt body potential.\n",
            (AD_V_RNG/AD_C_RNG/TAPE_G/ECG_G/2.),(AD_V_RNG/AD_C_RNG/TAPE_G/ECG_G/2.));
      printf("1) ST1_p - ST level, single-point, [ST-R+%d ms]-[BASE-R-%d ms].\n",
            (ST*1000/SAMPLE_FREQ),(BASE*1000/SAMPLE_FREQ));
      printf("2) ST1_a_l - ST level, avg & linear LS, 16ms window centered over pts in (1).\n");
      printf("3) ST1_w - ST level, weighted avg [.1,.2,.4,.2,.1], same as (2).\n");
      printf("4) ST1_pr - ST level, parabolic LS, same as (2).\n");
      printf("\nn_bt\tST1_p\tST1_a_l\tST1_w\tST1_pr\n");
      printf("\t(mV)\t(mV)\t(mV)\t(mV)\n");
      printf("----------------------------------------\n");
      for(i=0; i<st_avg_num; i++) {
        printf("%d\t%.3f\t%.3f\t%.3f\t%.3f\n",st_avg_bt[i],st_lvl_avg_p[i],
              st_lvl_avg_pal[i],st_lvl_avg_pw[i],st_lvl_avg_pr[i]); }
      printf("\n*** ST SLOPE ***\n");
      printf("5) STs_pw - ST slope, point & avg & wgt avg, line [STbegin-R+%d ms] to [STend-R+%d ms].\n",
            (J*1000/SAMPLE_FREQ),((ST+CAP)*1000/SAMPLE_FREQ));
      printf("6) STs_pr_l - ST slope, parabolic & linear LS, same as (5).\n");
      printf("\nn_bt\tSTs_paw\tSTs_pr_l\n");
      printf("\t(mV/s)\t(mV/s)\n");
      printf("-----------------------------\n");
      for(i=0; i<st_avg_num; i++)     {
        printf("%d\t%.3f\t%.3f\t\n",st_avg_bt[i],st_slp_avg_paw[i],
              st_slp_avg_pr_l[i]); }

stop: printf("\nEND OF TAPIS_ST ANALYSIS!\n\n");
}
/*****************************************************************/
hann(q0,q1,q2,q3,q4)
float q0,q1,q2,q3,q4;
{
```

ST_BRG_P.C 5-04-88 4:11pm

```
    int i;

    for(i=2; i<num_points-2; i++)
      data[i]=(int)(q0 * (float)data_org[i-2] +
                    q1 * (float)data_org[i-1] +
                    q2 * (float)data_org[i] +
                    q3 * (float)data_org[i+1] +
                    q4 * (float)data_org[i+2]);
}
/*****************************************************************/
pace_pk_find_sm()
{
    int i,j,k,l,pace_pk_index,init_pace_index;

    pace_num=j=k=0;

/* Store the location index of the pace fiducial marks */
    for(i=0; i<num_points; i++) {
      if(pace[i] == 2047) {
        pace_loc[pace_num]=i;
        pace_num++;        }          }

    if(pace_loc[0]<=PACE_WNDW) {
      pace_pk_index=pace_loc[0];
      pace_pk_loc[0]=pace_pk_index;
      trg_loc[pace_pk_index]=2047;
      j=1; }
    if(pace_loc[pace_num-1]>=(num_points-PACE_WNDW)) {
      pace_pk_index=pace_loc[pace_num-1];
      pace_pk_loc[pace_num-1]=pace_pk_index;
      trg_loc[pace_pk_index]=2047;
      k=1; }

/* Find the location index of the peaks of the pace artifacts */
    for(i=j; i<pace_num-k; i++)          {
      pace_pk_index=pace_loc[i];
      if(trg_loc[pace_pk_index]==1000) pace_pk_index=pace_loc[i]+5;
      init_pace_index = pace_pk_index;
      for(l=init_pace_index; l<(init_pace_index+PACE_WNDW+1); l++)
        if(abs(data[l]) > abs(data[l-1]) &&
           abs(data[l]) >= abs(data[l+1]) &&
           abs(data[l]) > abs(data[pace_pk_index]) &&
           trg_loc[l]!=1000)
             pace_pk_index = l;
      trg_loc[pace_pk_index]=2047;
      pace_pk_loc[i]=pace_pk_index;  }
}
/*****************************************************************/
pace_pk_find_lg()
{
    int i,j,k,l,pace_pk_index,big;

    pace_num=big=j=k=0;

/* Store the location index of the pace fiducial marks */
    for(i=0; i<num_points; i++) {
      if(pace[i] == 2047) {
        pace_loc[pace_num]=i;
        pace_num++;        }          }
```

```
ST_ABG_P.C   5-04-88 4:11pm                                    Page 7
      if(pace_loc[0]<=PACE_WNDW) {
         pace_pk_index=pace_loc[0];
         pace_pk_loc[0]=pace_pk_index;
         trg_loc[pace_pk_index]=2047;
         j=1; }
      if(pace_loc[pace_num-1]>=(num_points-PACE_WNDW)) {
         pace_pk_index=pace_loc[pace_num-1];
         pace_pk_loc[pace_num-1]=pace_pk_index;
         trg_loc[pace_pk_index]=2047;
         k=1; }

/* Find the location index of the peaks of the pace artifacts */
      for(i=j; i<pace_num-k; i++)          {
         pace_pk_index = pace_loc[i];
         for(l=pace_loc[i]-PACE_WNDW; l<(pace_loc[i]+PACE_WNDW+1); l++)
            if(abs(data[l]) >= big) {
               big=abs(data[l]);
               pace_pk_index = l;    }
         big=0;
         trg_loc[pace_pk_index]=2047;
         pace_pk_loc[i]=pace_pk_index;  }
}
/*********************************************************************/
qrs_pk_find_sm()
{
      int i,j,k,l,r_pk_index,init_r_index,pace_index,dc;
      long sum;

      qrs_num=pace_index=j=k=0;

/* Store the location index of the QRS fiducial marks */
      for(i=0; i<num_points; i++) {
         if(qrs[i] == 2047)  {
           qrs_loc[qrs_num]=i;
           qrs_num++;          }             }

      if(qrs_loc[0]<=QRS_WNDW) {
         r_pk_index=qrs_loc[0];
         qrs_pk_loc[0]=r_pk_index;
         trg_loc[r_pk_index]=1000;
         j=1; }
      if(qrs_loc[qrs_num-1]>=(num_points-QRS_WNDW)) {
         r_pk_index=qrs_loc[qrs_num-1];
         qrs_pk_loc[qrs_num-1]=r_pk_index;
         trg_loc[r_pk_index]=1000;
         k=1; }

/* Find the location index of the QRS peaks (R wave) */
      for(i=j; i<qrs_num-k; i++)         {
         sum=0;
         r_pk_index=qrs_loc[i];
         if(trg_loc[r_pk_index-2]==2047 ||
            trg_loc[r_pk_index-1]==2047 ||
            trg_loc[r_pk_index]==2047)
               r_pk_index=qrs_loc[i]+3;
         else if(trg_loc[r_pk_index+1]==2047 ||
            trg_loc[r_pk_index+2]==2047)
               r_pk_index=qrs_loc[i]+5;
         init_r_index = r_pk_index;
```

```
ST_ABG_P.C   5-04-88 4:11pm                                    Page 8
/* Find the dc in QRS window first...*/
         for(l=init_r_index-QRS_WNDW; l<(init_r_index+QRS_WNDW+1); l++)
            if(trg_loc[l]==2047) pace_index=l;

         for(l=init_r_index-QRS_WNDW; l<(init_r_index+QRS_WNDW+1); l++)
            if(l!=pace_index-2 && l!=pace_index-1 && l!=pace_index &&
               l!=pace_index+1 && l!=pace_index+2)
               sum += data[l];
         dc = sum/(long)(2*QRS_WNDW+1);

         for(l=init_r_index-QRS_WNDW; l<(init_r_index+QRS_WNDW+1); l++) {
/*
            printf("i=%d\tl=%d\td1-1=%d\td1=%d\td1+1=%d\n",i,l,
                  data[l-1],data[l],data[l+1]);
*/
            if(abs(data[l]-dc) > abs(data[l-1]-dc) &&
               abs(data[l]-dc) >= abs(data[l+1]-dc) &&
               abs(data[l]-dc) > abs(data[r_pk_index]-dc) &&
               trg_loc[l] != 2047)
                  r_pk_index = l;  }
         trg_loc[r_pk_index]=1000;
         qrs_pk_loc[i]=r_pk_index;
/*
         printf("\nr_pk_index=%d\tqrsloc=%d\tqrs_pk_loc=%d\ttrgloc=%d\n",
               r_pk_index,qrs_loc[i],qrs_pk_loc[i],trg_loc[r_pk_index]);
*/
                                       }
}
/*********************************************************************/
qrs_pk_find_lg()
{
      int i,j,k,l,r_pk_index,big,dc;
      long sum;

      qrs_num=big=j=k=0;

/* Store the location index of the qrs fiducial marks */
      for(i=0; i<num_points; i++) {
         if(qrs[i] == 2047) {
           qrs_loc[qrs_num]=i;
           qrs_num++;        }           }

      if(qrs_loc[0]<=QRS_WNDW) {
         r_pk_index=qrs_loc[0];
         qrs_pk_loc[0]=r_pk_index;
         trg_loc[r_pk_index]=1000;
         j=1; }
      if(qrs_loc[qrs_num-1]>=(num_points-QRS_WNDW)) {
         r_pk_index=qrs_loc[qrs_num-1];
         qrs_pk_loc[qrs_num-1]=r_pk_index;
         trg_loc[r_pk_index]=1000;
         k=1; }

/* Find the location index of the peaks of the qrs complex */
      for(i=j; i<qrs_num-k; i++)          {
         sum=0;
         r_pk_index = qrs_loc[i];

         for(l=qrs_loc[i]-QRS_WNDW; l<(qrs_loc[i]+QRS_WNDW+1); l++)
            sum += data[l];
```

```
ST_EKG_P.C    5-04-88 4:11pm                                          Page 9
        dc = sum / (long)(2*QRS_WNDW+1);

        for(l=qrs_loc[i]-QRS_WNDW; l<(qrs_loc[i]+QRS_WNDW+1); l++)
             if(abs(data[l]-dc) >= big) {
                big=abs(data[l]-dc);
                r_pk_index = l;    }
        big=0;
        trg_loc[r_pk_index]=1000;
        qrs_pk_loc[i]=r_pk_index;   }
}
/*************************************************************************/
capture_p()

/*Capture: If (1) the inst HRs are within +-DELTA_HR bpm (or RR intervals within
                 +-DELTA_RR ms or RR or HR within a percentage) for 4
                 consecutive beats, i.e. 3 inst HRs as calculated from the
                 4 beats,
             (2) the associated pace artifact for an R wave is in a
                 window 120 ms beyond the previous R wave and 80 ms before the
                 present R wave,
             (3) the 3 pace-R time for the last 3 beats must be within 5%
                 of each other,
           Then, the 4th beat is considered as captured. (i.e. learning period
           of 3 beats before report of capture).

NOTE: Any group of captured beats associated w/ 2nd degree AV block of the type
      m/n (n<5, m<4) will not be considered as captured beats (eg. 2/1, 3/2).
      Therefore, AV block of the type 5/4 & 6/5 will have 1 and 2 beats
      reported as captured, respectively.
*/
{
      int i,j;
      j=0;  /* initialize the index for pace_pk_loc */
      printf("\nbeat\tHR(bpm)\tRR(s)\tPR(s)\tCAPTURE?\n");
      printf("------------------------------------------------\n");
      printf("1\t---\t---\n");
      for(i=1; i<qrs_num; i++)   {
         rr[i]=(float)(qrs_pk_loc[i]-qrs_pk_loc[i-1])/(float) SAMPLE_FREQ;
         hr[i]=ceil((double)(60. / rr[i]));

         if((i>2) && (((rr[i]-rr[i-2]) <= DELTA_RR) &&
           ((rr[i]-rr[i-2]) >= -(DELTA_RR))) && (((rr[i]-rr[i-1]) <=
           DELTA_RR) && ((rr[i]-rr[i-1]) >= -(DELTA_RR))))
         {
/*
         if((i>2) && (((hr[i]-hr[i-2]) <= DELTA_HR) &&
           ((hr[i]-hr[i-2]) >= -(DELTA_HR))) && (((hr[i]-hr[i-1]) <=
           DELTA_HR) && ((hr[i]-hr[i-1]) >= -(DELTA_HR))))
           {

         if((i>2) && (LOW_RR*(float)abs(hr[i]-hr[i-2]) <=
                               (float)abs(hr[i]-hr[i-1])) &&
                     (HIGH_RR*(float)abs(hr[i]-hr[i-2]) >=
                               (float)abs(hr[i]-hr[i-1])))
           {

         if((i>2) && (LOW_RR*(float)fabs((double)(rr[i]-rr[i-2])) <=
                               (float)fabs((double)(rr[i]-rr[i-1]))) &&
                     (HIGH_RR*(float)fabs((double)(rr[i]-rr[i-2])) >=
                               (float)fabs((double)(rr[i]-rr[i-1]))))
```

```
ST_EKG_P.C    5-04-88 4:11pm                                          Page 10
           {
*/
            while ((j<pace_num) && (pace_pk_loc[j] <= qrs_pk_loc[i]))
               j++;
            if(j==0)
               {
                  prcode=0;
                  mes=" ";
                  goto there;
               }
            else j=j-1; /* find first pace artifact before current R wave */
/* printf("\nAfter RR check\n"); */
            if(((qrs_pk_loc[i-3]+ST+CAP+CAP/2) < pace_pk_loc[j-2]) &&
                ((qrs_pk_loc[i-2]-BASE-CAP) > pace_pk_loc[j-2]) &&
                ((qrs_pk_loc[i-2]+ST+CAP+CAP/2) < pace_pk_loc[j-1]) &&
                ((qrs_pk_loc[i-1]-BASE-CAP) > pace_pk_loc[j-1]) &&
                ((qrs_pk_loc[i-1]+ST+CAP+CAP/2) < pace_pk_loc[j]) &&
                ((qrs_pk_loc[i]-BASE-CAP) > pace_pk_loc[j]))
                {
/* printf("\nAfter check 1 (pace between ST and BASE)\n"); */
                  if(((qrs_pk_loc[i-2]-pace_pk_loc[j-2]) <=
                      (int)(HIGH_PR*(float)(qrs_pk_loc[i]-pace_pk_loc[j]))) &&
                     ((qrs_pk_loc[i-2]-pace_pk_loc[j-2]) >=
                      (int)(LOW_PR*(float)(qrs_pk_loc[i]-pace_pk_loc[j]))) &&
                     ((qrs_pk_loc[i-1]-pace_pk_loc[j-1]) <=
                      (int)(HIGH_PR*(float)(qrs_pk_loc[i]-pace_pk_loc[j]))) &&
                     ((qrs_pk_loc[i-1]-pace_pk_loc[j-1]) >=
                      (int)(LOW_PR*(float)(qrs_pk_loc[i]-pace_pk_loc[j]))))
                     {
/* printf("\nAfter check 2 (AV block)\n"); */
                     if(((qrs_pk_loc[i]+J-CAP) <= pace_pk_loc[j+1]) &&
                        ((qrs_pk_loc[i]+ST+CAP+CAP/2) >= pace_pk_loc[j+1]))
                       goto here;
                     else {
                       mes="CAPTURE";
                       pr=(float)(qrs_pk_loc[i]-pace_pk_loc[j])/
                          (float)SAMPLE_FREQ;
                       r_cap_pk_loc[tot_r_cap_num]=qrs_pk_loc[i];
                       cap_beat[tot_r_cap_num]=i+1;
                       tot_r_cap_num++;
                       r_cap_num++;
                       sinus_code=1;
                       prcode=1;
                          }        /*end else*/
                     }             /*end 3rd_if*/
                   */
                     {
                     if(((qrs_pk_loc[i]+J-CAP) <= pace_pk_loc[j+1]) &&
                        ((qrs_pk_loc[i]+ST+CAP+CAP/2) >= pace_pk_loc[j+1])) {
                       mes="CAPTURE, AV BLK --> ARTF ON ST SEG. NO ST!";
                       goto here1;  }
                     else {
                        mes="CAPTURE, POSSIBLE AV BLK DEVELOPING!";
                        pr=(float)(qrs_pk_loc[i]-pace_pk_loc[j])/
                           (float)SAMPLE_FREQ;
                        r_cap_pk_loc[tot_r_cap_num]=qrs_pk_loc[i];
                        cap_beat[tot_r_cap_num]=i+1;
                        tot_r_cap_num++;
                        r_cap_num++;
                        sinus_code=1;
```

```
PT_RMG_P.C   5-04-88 4:11pm                                          Page 11
                        prcode=1;
                          }              /*end else*/
                      }                  /*end else 3rd_if*/
                  }                      /*end 2nd_if*/
              else
                  {
/* printf("Before check for artf on pr or st\n"); */
                    if((((qrs_pk_loc[i-2]-BASE-CAP) <= pace_pk_loc[j-2]) &&
                        ((qrs_pk_loc[i-2]-BASE+CAP) >= pace_pk_loc[j-2]) &&
                        ((qrs_pk_loc[i-1]-BASE-CAP) <= pace_pk_loc[j-1]) &&
                        ((qrs_pk_loc[i-1]-BASE+CAP) >= pace_pk_loc[j-1]) &&
                        ((qrs_pk_loc[i]-BASE-CAP) <= pace_pk_loc[j]) &&
                        ((qrs_pk_loc[i]-BASE+CAP) >= pace_pk_loc[j])) ||
                       (((qrs_pk_loc[i-2]+J-CAP) <= pace_pk_loc[j-1]) &&
                        ((qrs_pk_loc[i-2]+ST+CAP+CAP/2) >= pace_pk_loc[j-1]) &&
                        ((qrs_pk_loc[i-1]+J-CAP) <= pace_pk_loc[j]) &&
                        ((qrs_pk_loc[i-1]+ST+CAP+CAP/2) >= pace_pk_loc[j])))
/* printf("Before here tag\n"); */
  here:                 mes="CAPTURE, ARTF ON PR OR ST SEG. NO ST!";
  here1:                prcode = 0;
                        if(sinus_code==1) {
                        r_cap_num_div[div] = r_cap_num;
                        r_cap_num=0;
                        r_cap_num_reset[div+1]=tot_r_cap_num;
                        div++;
                        sinus_code=0;       }
                        goto there;
                      }                   /*end 2sif*/
                    else if(((qrs_pk_loc[i-2]-BASE+CAP) < pace_pk_loc[j-2]) &&
                            (pace_pk_loc[j-2] <= qrs_pk_loc[i-2]) &&
                           ((qrs_pk_loc[i-1]-BASE+CAP) < pace_pk_loc[j-1]) &&
                            (pace_pk_loc[j-1] <= qrs_pk_loc[i-1]) &&
                           ((qrs_pk_loc[i]-BASE+CAP) < pace_pk_loc[j]) &&
                            (pace_pk_loc[j] <= qrs_pk_loc[i]))
                         {
                         if(((qrs_pk_loc[i]+J-CAP) <= pace_pk_loc[j+1]) &&
                            ((qrs_pk_loc[i]+ST+CAP+CAP/2) >= pace_pk_loc[j+1]))
                           {
                           mes="CAPTURE W/ LARGE AV DELAY, ST ARTF, NO ST!";
                           goto here1;
                           }
                         else {
                           pr=(float)(qrs_pk_loc[i]-pace_pk_loc[j-i])/
                                (float)SAMPLE_FREQ;
                           mes="CAPTURE W/ SIGNIFICANT AV DELAY";
                           r_cap_pk_loc[tot_r_cap_num]=qrs_pk_loc[i];
                           cap_beat[tot_r_cap_num]=i+1;
                           tot_r_cap_num++;
                           r_cap_num++;
                           sinus_code=1;
                           prcode=1;
                              }
                         }
                    else if(((qrs_pk_loc[i-3]+J-CAP) > pace_pk_loc[j-2]) &&
                            (qrs_pk_loc[i-3] <= pace_pk_loc[j-2]) &&
                           ((qrs_pk_loc[i-2]+J-CAP) > pace_pk_loc[j-1]) &&
                            (qrs_pk_loc[i-2] <= pace_pk_loc[j-1]) &&
                           ((qrs_pk_loc[i-1]+J-CAP) > pace_pk_loc[j]) &&
                            (qrs_pk_loc[i-1] <= pace_pk_loc[j]))
                         {
```

```
PT_RMG_P.C   5-04-88 4:11pm                                          Page 12
                         if(((qrs_pk_loc[i]+J-CAP) <= pace_pk_loc[j+1]) &&
                            ((qrs_pk_loc[i]+ST+CAP+CAP/2) >= pace_pk_loc[j+1]))
                           {
                           mes="CAPTURE W/ LARGE AV DELAY, ST ARTF, NO ST!";
                           goto here1;
                           }
                         else {
                           pr=(float)(qrs_pk_loc[i]-pace_pk_loc[j])/
                               (float)SAMPLE_FREQ;
                           mes="CAPTURE W/ SIGNIFICANT AV DELAY";
                           r_cap_pk_loc[tot_r_cap_num]=qrs_pk_loc[i];
                           cap_beat[tot_r_cap_num]=i+1;
                           tot_r_cap_num++;
                           r_cap_num++;
                           sinus_code=1;
                           prcode=1;
                              }
                         }
                    else  {
                      if(((qrs_pk_loc[i]+J-CAP) <= pace_pk_loc[j+1]) &&
                         ((qrs_pk_loc[i]+ST+CAP+CAP/2) >= pace_pk_loc[j+1]))
                         {
                         mes="POSBL --> CAP OR CAP < P_RATE, ST ARTF, NO ST!";
                         goto here1;
                         }
                      else  {
                           mes="POSBL --> SUST CAPT OR CAPT < PACE RATE. NO ST!";
                           goto here1;
                           }
                          }
                                         /*end else_2ndif*/
            }                            /*end 1st_if*/
          }
        else
          {
          mes=" ";
          prcode = 0;
          if(sinus_code==1) {
          r_cap_num_div[div] = r_cap_num;
          r_cap_num=0;
          r_cap_num_reset[div+1]=tot_r_cap_num;
          div++;
          sinus_bt_no[num_of_sinus]=i+1;
          sinus_rec[n·· of_sinus++]=rr[i];
          sinus_code=v;      }
          }                                        /*end else 1st_if*/

there:    if(prcode==0)
            printf("%d\t%d\t%.3f\t\t%s\n",(i+1),hr[i],rr[i],mes);
          else
            printf("%d\t%d\t%.3f\t%.3f\t%s\n",(i+1),hr[i],rr[i],pr,mes);
                                 }              /*end for*/
}
/**********************************************************************/
capture_np(p_rate)
/*
Capture: (1) the inst HRs must be within DELTA_HR bpm (or RR intervals within
             +-DELTA_RR ms) for 4 consecutive beats, i.e. 3 inst HRs as
             calculated from the 4 beats.
*/
int p_rate;
```

ST_SEG_P.C 5-04-88 4:11pm Page 13

```
{
      int i;
      printf("\nbeat\tRR(bpm)\tRR(s)\tCAPTURE?\n");
      printf("----------------------------------\n");
      printf("1\t---\t---\n");
      for(i=1; i<qrs_num; i++)  {
         rr[i]=(float)(qrs_pk_loc[i]-qrs_pk_loc[i-1])/(float) SAMPLE_FREQ;
         hr[i]=ceil((double)(60. / rr[i]));

         if((i>2) && (((rr[i]-rr[i-2]) <= DELTA_RR) &&
           ((rr[i]-rr[i-2]) >= -(DELTA_RR))) && (((rr[i]-rr[i-1]) <=
           DELTA_RR) && ((rr[i]-rr[i-1]) >= -(DELTA_RR))))
         {
/*
         if((i>2) && (((hr[i]-hr[i-2]) <= DELTA_HR) &&
           ((hr[i]-hr[i-2]) >= -(DELTA_HR))) && (((hr[i]-hr[i-1]) <=
           DELTA_HR) && ((hr[i]-hr[i-1]) >= -(DELTA_HR))))
             {

         if((i>2) &&  (LOW_RR*(float)hr[i-2]<=(float)hr[i]) &&
                      (HIGH_RR*(float)hr[i-2]>=(float)hr[i]) &&
                      (LOW_RR*(float)hr[i-1]<=(float)hr[i]) &&
                      (HIGH_RR*(float)hr[i-1]>=(float)hr[i]))
           {

         if((i>2) &&  (LOW_RR*rr[i-2]<=rr[i]) &&
                      (HIGH_RR*rr[i-2]>=rr[i]) &&
                      (LOW_RR*rr[i-1]<=rr[i]) &&
                      (HIGH_RR*rr[i-1]>=rr[i]))
           {
*/
             if(((p_rate-DELTA_HR) <= hr[i]) && (hr[i] <= (p_rate+DELTA_HR))) {
                mes="CAPTURE";
                r_cap_pk_loc[tot_r_cap_num]=qrs_pk_loc[i];
                cap_beat[tot_r_cap_num]=i+1;
                tot_r_cap_num++;
                r_cap_num++;
                sinus_code=1; }
             else
                mes="POSBL CAPT < PACE RATE OR GOING INTO SUST CAPT";
           }
         else {
                mes=" ";
                if(sinus_code==1) {
                r_cap_num_div[div] = r_cap_num;
                r_cap_num=0;
                r_cap_num_reset[div+1]=tot_r_cap_num;
                div++;
                sinus_bt_no[num_of_sinus]=i+1;
                sinus_rea[num_of_sinus++]=rr[i];
                sinus_code=0;     }
              }
     printf("%d\t%d\t%.3f\t%s\n", (i+1),hr[i],rr[i],mes);
                                   }            /*end for*/
}
/*******************************************************************/
st_r(t,d)
int t,d;
{
    int     base_cent,st_cent,j_point,qrs_pk,beat,reset_lvl,st_pcode,i,j;
```

ST_SEG_P.C 5-04-88 4:11pm Page 14

```
     long    sigma_x,sigma_x2,sigma_y,sigma_xy,x,avg_x;
     float   base_slp,base_incp,st_lvl_mv,st_slp_mv,st_lvl_avg,st_slp_avg,
             st_slp,st_incp,base,st,r_ampl,st_lvl_sum,st_slp_sum;
     double r,r1,r2,r3,avg_y,temp,temp1,temp2;
     int s;

     st_lvl_sum = st_slp_sum = 0.;

     for(i=0; i<r_cap_num_div[d]; i++) {
        reset_lvl = r_cap_num_reset(d);
        beat = cap_beat[reset_lvl+i];
        qrs_pk = r_cap_pk_loc[reset_lvl+i];
        base_cent=qrs_pk-BASE;
        st_cent=qrs_pk+ST;
        j_point=qrs_pk+J;
/*
     printf("R=%d\n\n",data_org[qrs_pk]);
     for (s=base_cent-2; s<base_cent+3; s++)
        printf("base[%d]=%d\n",s,data[s]);
     printf("\n");
     for (s=j_point; s<(st_cent+CAP+1); s++)
        printf("st[%d]=%d\n",s,data[s]);
     printf("\n");
*/
        switch(t) {
        case 1 : /**************** SINGLE-POINT ST ********************/
        st_lvl_mv=(float)(data[st_cent]-data[base_cent])
                 *AD_V_RNG/AD_C_RNG/TAPE_G/ECG_G-reset_st[0];
/*
        st_slp_mv=(float)(data[st_cent+FIT]-data[st_cent-FIT])
                 /(2.*FIT)*AD_V_RNG/AD_C_RNG/TAPE_G/ECG_G*(float)SAMPLE_FREQ;
*/
        st_slp_mv=(float)(data[st_cent+CAP]-data[j_point])/(ST+CAP-J)*AD_V_RNG
                 /AD_C_RNG/TAPE_G/ECG_G*(float)SAMPLE_FREQ;

        r_ampl=(float)(data_org[qrs_pk]-data[base_cent])*AD_V_RNG/AD_C_RNG/TAPE_G
              /ECG_G;
        break;

        case 2 : /**************** AVERAGE ST ****************/
        base=(float)(data[base_cent-2]+data[base_cent-1]+data[base_cent]
             +data[base_cent+1]+data[base_cent+2])/5.;
        st=(float)(data[st_cent-2]+data[st_cent-1]+data[st_cent]
             +data[st_cent+1]+data[st_cent+2])/5.;
        st_lvl_mv = (st-base)*AD_V_RNG/AD_C_RNG/TAPE_G/ECG_G-reset_st[1];
/*
        st_slp_mv =  (float)(data[st_cent+FIT]-data[st_cent-FIT])/(2.*FIT)
                 *AD_V_RNG/AD_C_RNG/TAPE_G/ECG_G*(float)SAMPLE_FREQ;
*/
        st_slp_mv=(float)(data[st_cent+CAP]-data[j_point])/(ST+CAP-J)*AD_V_RNG
                 /AD_C_RNG/TAPE_G/ECG_G*(float)SAMPLE_FREQ;

        r_ampl=((float)data_org[qrs_pk]-base)*AD_V_RNG/AD_C_RNG/TAPE_G/ECG_G;
        break;

        case 3 : /**************** WEIGHTED AVERAGE ST *************/
                 /****************(0.1,0.2,0.4,0.2,0.1)*************/
        base=(0.1*(float)data[base_cent-2]+0.2*(float)data[base_cent-1]
             +0.4*(float)data[base_cent]+0.2*(float)data[base_cent+1]
             +0.1*(float)data[base_cent+2]);
```

ST_RNG_P.C   5-04-88 4:11pm   Page 15

```
        st=(0.1*(float)data[st_cent-2]+0.2*(float)data[st_cent-1]+
            0.4*(float)data[st_cent]+0.2*(float)data[st_cent+1]+
            0.1*(float)data[st_cent+2]);
        st_lvl_mv = (st-base)*AD_V_RNG/AD_C_RNG/TAPE_G/ECG_G-rest_st[2];
/*
        st_slp_mv = (float)(data[st_cent+FIT]-data[st_cent-FIT])/(2.*FIT)
                    *AD_V_RNG/AD_C_RNG/TAPE_G/ECG_G*(float)SAMPLE_FREQ;
*/
        st_slp_mv=(float)(data[st_cent+CAP]-data[j_point])/(ST+CAP-J)*AD_V_RNG/AD_C_RNG/
                  TAPE_G/ECG_G*(float)SAMPLE_FREQ;

        r_ampl=((float)data_org[qrs_pk]-base)*AD_V_RNG/AD_C_RNG/TAPE_G/ECG_G;
        break;

        case 4 : /**************** PARABOLIC LS ST ****************/
        base=(-3.*(float)data[base_cent-2]+12.*(float)data[base_cent-1]+
              17.*(float)data[base_cent]+12.*(float)data[base_cent+1]-
              3.*(float)data[base_cent+2])/35.;
        st=(-3.*(float)data[st_cent-2]+12.*(float)data[st_cent-1]+
            17.*(float)data[st_cent]+12.*(float)data[st_cent+1]-
            3.*(float)data[st_cent+2])/35.;
        st_lvl_mv = (st-base)*AD_V_RNG/AD_C_RNG/TAPE_G/ECG_G-rest_st[3];

        st_slp_mv=(-5.*(float)data[st_cent+CAP-10]-4.*(float)data[st_cent+CAP-9]
                   -3.*(float)data[st_cent+CAP-8]-2.*(float)data[st_cent+CAP-7]
                   -(float)data[st_cent+CAP-6]+(float)data[st_cent+CAP-4]
                   +2.*(float)data[st_cent+CAP-3]+3.*(float)data[st_cent+CAP-2]
                   +4.*(float)data[st_cent+CAP-1]+5.*(float)data[st_cent+CAP])
                   /110.*AD_V_RNG/AD_C_RNG/TAPE_G/ECG_G*(float)SAMPLE_FREQ;
/*
        st_slp_mv=(-2.*(float)data[st_cent-2]-(float)data[st_cent-1]
                   +(float)data[st_cent+1]+2.*(float)data[st_cent+2])
                   /10.*AD_V_RNG/AD_C_RNG/TAPE_G/ECG_G*(float)SAMPLE_FREQ;
*/
        r_ampl=((float)data_org[qrs_pk]-base)*AD_V_RNG/AD_C_RNG/TAPE_G/ECG_G;
        break;

        case 5 : /**************** LINEAR LS ST ****************/
        base_slp=base_incp=0.;
        x=sigma_x=sigma_x2=sigma_y=sigma_xy=0;
        for(j=base_cent-FIT; j<(base_cent+FIT+1); j++) {
           sigma_y += (long)data[j];
           sigma_xy += ((long)data[j] * x);
           sigma_x += x;
           sigma_x2 += sqr(x);
           x++;                                        }
        avg_y = (double)sigma_y/(double)(2*FIT+1);
        avg_x = sigma_x / (2*FIT+1);
        base_slp=(float)((double)(2*FIT+1)*(double)sigma_xy-sigma_x*(double)sigma_y)
                  /((double)(2*FIT+1)*sigma_x2 - sqr(sigma_x));
        base_incp=(float)(avg_y-(double)avg_x*(double)base_slp);
        base = base_slp*(float)avg_x + base_incp;

        x=sigma_y=sigma_xy=0;
        st_slp=st_incp=0.;
        for(j=st_cent-FIT;j<(st_cent+FIT+1); j++)      {
           sigma_y += (long)data[j];
           sigma_xy += ((long)data[j]*x);
           x++;                                        }
        avg_y = (double) sigma_y / (double)(2*FIT+1);
```

ST_RNG_P.C   5-04-88 4:11pm   Page 16

```
        st_slp_mv=(float)((double)(2*FIT+1)*(double)sigma_xy-sigma_x*(double)sigma_y)
                  /((double)(2*FIT+1)*sigma_x2-sqr(sigma_x));
        st_incp=(float)(avg_y-(double)avg_x*(double)st_slp_mv);
        st = st_slp_mv * (float)avg_x + st_incp;
        st_lvl_mv=(st-base)*AD_V_RNG/AD_C_RNG/TAPE_G/ECG_G-rest_st[4];

        x=sigma_x=sigma_x2=sigma_y=sigma_xy=0;
        for(j=j_point;j<(st_cent+CAP+1); j++)      {
           sigma_y += (long)data[j];
           sigma_xy += ((long)data[j]*x);
           sigma_x += x;
           sigma_x2 += sqr(x);
           x++;                                    }
        avg_y = (double) sigma_y / (double)(st_cent+CAP-j_point+1);
        avg_x = sigma_x / (st_cent+CAP-j_point+1);

        r = r1 = r2 = r3 = 0.;
        temp = temp1 = temp2 = 0.;
        s = 0;
        for(j=j_point; j<(st_cent+CAP+1); j++)      {
           temp1 = (double)(s-avg_x);
           temp2 = (double)data[j] - avg_y;
           r1 += (temp1 * temp2);
           r2 += sqr(temp1);
           r3 += sqr(temp2);
           s++;                                     }
        temp = r2 * r3;
        if (temp == 0.)
           r = 0.;
        else
           r = r1 / sqrt(temp);

        st_slp_mv=(float)((double)(st_cent+CAP-j_point+1)*(double)sigma_xy-
                  (double)sigma_x*(double)sigma_y)/
                  ((double)(st_cent+CAP-j_point+1)*(double)sigma_x2-
                  (double)sqr(sigma_x));
        st_slp_mv = st_slp_mv * AD_V_RNG/AD_C_RNG/TAPE_G/ECG_G*
                    (float)SAMPLE_FREQ;

        r_ampl=((float)data_org[qrs_pk]-base)*AD_V_RNG/AD_C_RNG/TAPE_G/ECG_G;
        break;    }

/*  Denote the pr, j, st, and st+CAP  points in trig file */
    trg_loc[base_cent] = trg_loc[st_cent]=-750;
    trg_loc[j_point] = trg_loc[st_cent+CAP]= -500;

/*  Calculate the averaged ST level and slope */
    if((i % (int) NUM) == ((int) NUM - 1)) {
        st_avg_bt[st_avg_num]=beat;
        st_lvl_avg = (st_lvl_sum + st_lvl_mv) / NUM;
        st_slp_avg = (st_slp_sum + st_slp_mv) / NUM;
        switch(t) {
        case 1:
           st_lvl_avg_p[st_avg_num]=st_lvl_avg;
           break;
        case 2:  case 5:
           st_lvl_avg_pl[st_avg_num]=st_lvl_avg;
           break;
        case 3:
```

```
ST_SEG_P.C    5-04-88 4:11pm                                          Page 17
            st_lvl_avg_pw[st_avg_num]=st_lvl_avg;
            break;
        case 4:
            st_lvl_avg_pr[st_avg_num]=st_lvl_avg;
            break; }
        switch(t) {
        case 1:  case 2:  case 3:
            st_slp_avg_paw[st_avg_num]=st_slp_avg;
            break;
        case 4: case 5:
            st_slp_avg_pr_l[st_avg_num]=st_slp_avg;
            break; }
        st_avg_num++;
        st_lvl_sum = st_slp_sum = 0.;
        st_pcode = 1;                          }
    else                    {
        st_lvl_sum += st_lvl_mv;
        st_slp_sum += st_slp_mv;
        st_pcode = 0; }

/*  Report the results */
    if(linear_code==0) {
        if(st_pcode == 1)
          printf("%d\t%.3f\t%.3f\t%.3f\t%.3f\t%.3f\n",beat,st_lvl_mv,st_slp_mv,
               st_lvl_avg,st_slp_avg,r_ampl);
        if(st_pcode == 0)
          printf("%d\t%.3f\t%.3f\t\t\t%.3f\n",beat,st_lvl_mv,st_slp_mv,
               r_ampl);  }

    if(linear_code==1) {
        if(st_pcode == 1)
          printf("%d\t%.3f\t%.3f\t%.2f\t%.3f\t%.3f\t%.3f\n",beat,st_lvl_mv,
               st_slp_mv,r,st_lvl_avg,st_slp_avg,r_ampl);
        if(st_pcode == 0)
          printf("%d\t%.3f\t%.3f\t%.2f\t\t\t%.3f\n",beat,st_lvl_mv,st_slp_mv,
               r,r_ampl);}
                              } /* end for */
}
/**********************************************************************/
read_data(infile,code)
char *infile;
int  code;
{
        int   i,temp,check;
        float ftemp;
        FILE  *fpi;

        if((fpi=fopen(infile,"r")) == NULL) {
             printf("error -> unable to open input ascii file %s.\n",infile);
             exit(1);                     }

        if (code == 1) {
           for(i=0; ((fscanf(fpi,"%d",&temp)!=EOF) && (i<MAXNUM)); i++)
              pace[i] = temp;            }

        else if (code == 2) {
           for(i=0; ((fscanf(fpi,"%d",&temp)!=EOF) && (i<MAXNUM)); i++)
              qrs[i] = temp;             }

        else if (code == 3) {
```

```
ST_SEG_P.C    5-04-88 4:11pm                                          Page 18
           for(i=0; (fscanf(fpi, "%d",&temp) != EOF) && (i<MAXNUM); i++)
              data_org[i] = temp;
              num_points = i;           }

        else if (code == 4) {
           for(i=0; (fscanf(fpi,"%f",&ftemp) != EOF); i++)
              rest_st[i]=ftemp;         }

        else { printf("\nWrong read ascii code (1-4)!\n"); exit(1); }

        check = fclose(fpi);
        if(check != 0) {
           printf("error -> unable to close input ascii file %s.\n",infile);
           exit(1);     }
}
/**********************************************************************/
read_b_data(infile,code)
char *infile;
int  code;
{
        int   i,check;
        FILE  *fpi;

        if((fpi=fopen(infile,"rb")) == NULL) {
             printf("error -> unable to open input binary file %s.\n",infile);
             exit(1);                   }

        if (code == 1)
           for(i=0; i<MAXNUM && !feof(fpi); i++)
              pace[i]=(int)getw(fpi);

        else if (code == 2)
           for(i=0; i<MAXNUM && !feof(fpi); i++)
              qrs[i]=(int)getw(fpi);

        else if (code == 3)   {
            for(i=0; i<MAXNUM && !feof(fpi); i++)
              data_org[i]=(int)getw(fpi);
            num_points=i;     }

        else if (code == 4)
           for(i=0; i<6 && !feof(fpi); i++)
              rest_st[i]=(float)getw(fpi);

        else { printf("\nWrong code for read binary (1-4)!\n"); exit(1); }

        check = fclose(fpi);
        if(check != 0) {
           printf("error -> unable to close input binary file %s.\n",infile);
           exit(1);     }
}
/**********************************************************************/
write_data(outfile)
char *outfile;
{
        int i,check;
        FILE *fpo;

        if((fpo = fopen(outfile,"w")) == NULL) {
           printf("error -> unable to open output ascii file %s.\n",outfile);
```

```
        exit(1);                          }

    for(i=0; i<num_points; i++)
        fprintf(fpo,"%6d%s",trg_loc[i],(i % 10 == 9 ? '\n' : ' '));

    check = fclose(fpo);
    if(check != 0) {
        printf("error -> unable to close output ascii file %s.\n",outfile);
        exit(1);    }
}
/*******************************************************************/
write_b_data(outfile)
char *outfile;
{
    int i,check;
    FILE *fpo;

    if((fpo = fopen(outfile,"wb")) == NULL) {
        printf("error -> unable to open output binary file %s.\n",outfile);
        exit(1);                          }

    fwrite(trg_loc,sizeof(int),num_points,fpo);

    check = fclose(fpo);
    if(check != 0) {
        printf("error -> unable to close output binary file %s.\n",outfile);
        exit(1);    }
}
```

```
ST_SEG_R.C   5-04-88 3:50pm                                                     Page 1
/*****************************************************************************
 This program calculates an average resting ECG ST level over all (normal)
 beats by five different computer methods.  These values are written into
 a file.  This file can be read by another program (which processes stress
 ECG) to calculate additional ST level shifts.

 Usage:  st_seg_r 0 <reststfile> <w_B_A>
         [For when either no rest ECG is available or calculation of
          additional ST level shift in the later processing stages is not
          desired.  ST level of 0.000 mV is assumed for all five methods]

         st_seg_r 1 <reststfile> <qrstrigfile> <datafile> <w_B_A> <r_B_A> <trgfile>
         [For when calculation of resting ECG ST level is desired]

         <w_B_A, r_B_A: 0=binary, 1=ascii for writing and reading files>

Author: Hossein Jadvar
Date:   January 1988
*****************************************************************************/

#include <\msc\include\stdio.h>
#include <\msc\include\stdlib.h>
#include <\msc\include\math.h>

#define MAXNUM          32767  /* 131 s, min 2.048 s at 250 Hz */
#define SAMPLE_FREQ     250    /* in Hz */
#define FIT             2      /* 2*FIT+1 pts fit for linear and parab STlvl */
#define GAIN            10     /* 10 mm/mv */
#define CAP             5      /* for end of ST, STend=100 ms after R */
#define BASE            (60 * SAMPLE_FREQ /1000)      /* 60 ms before R */
#define ST              (80 * SAMPLE_FREQ / 1000)   /* 80 ms after R */
#define J               (60 * SAMPLE_FREQ / 1000)     /* 60 ms after R */
#define QRS_WNDW        15     /* +- 60 ms at 250 Hz window for finding peak*/
#define ECG_G           1000.  /* gain of the ECG machine */
#define TAPE_G          0.5    /* tape recorder gain */
#define AD_V_RNG        10000. /* 10 V, i.e. +-5 V AD range */
#define AD_C_RNG        4096.  /* 12 bit resolution */
#define sqr(x)          x * x

int     num_points,qrs_num,linear_code,nr_r_code;

int     qrs[MAXNUM],data[MAXNUM],data_org[MAXNUM],
        qrs_loc[200],qrs_pk_loc[200],trg_loc[MAXNUM];

float   rest_st[5];
char    *mes;

main(argc,argv)
int argc;
char *argv[];
{
      int    i,file_code,r_filecode,w_filecode,type;

      nr_r_code=atoi(argv[1]);

      if(argc!=4 && argc!=8) {
         printf("\nUsage:\n");
         printf("st_seg_r 0 st_r_f w_B_A(0/1)\n");
         printf("st_seg_r 1 st_r_f qrstrg_f data_f w_B_A r_B_A trg_f\n");
         exit(1);            }
```

```
ST_SEG_R.C   5-04-88 3:50pm                                                     Page 2

      if((nr_r_code != 0) && (nr_r_code != 1)) {
         printf("\nUse either code 0 (no rest ECG) or 1 (rest ECG).\n");
         exit(1);                                   }

      if(nr_r_code==0)       {
         if(argc != 4) {
           printf("\nUsage: st_seg_r 0 st_r_f w_B_A(0/1)\n");
           exit(1);      }
         else {
            printf("\nNO REST ECG GIVEN, REST ST LEVEL = 0 mV.\n");
            w_filecode = atoi(argv[3]);
            goto here; }    }

      if(nr_r_code==1) {
         if(argc != 8) {
           printf("\nUsage: st_seg_r 1 st_r_f qrstrg_f data_f w_B_A r_B_A
                   trg_f\n");
           exit(1);      }
         else {
           r_filecode = atoi(argv[6]);
           w_filecode = atoi(argv[5]);
              if(r_filecode == 0) {
                 for(file_code=1; file_code<3; file_code++) {
                    printf("\nReading binary file %s...\n",argv[file_code+2]);
                    read_b_data(argv[file_code+2],file_code); }  }
              else {
                 for(file_code=1; file_code<3; file_code++) {
                    printf("\nReading ascii file %s...\n",argv[file_code+2]);
                    read_data(argv[file_code+2],file_code);    }  }  }  }

/* Smooth the data for pace and qrs peak detection and ST measurements;
   the R amplitude measurements use the original data */
      printf("\nSmoothing...(3 pt Hanning filter)...\n");
      hann(0.,0.25,0.5,0.25,0.);

/* Find and mark the location of peak of R waves detected */
      qrs_pk_find();

/* Report general info about the input data */
      printf("\nTotal number of points in the record = %d\n",num_points);
      printf("\nTotal record length = %.3f seconds\n",((float)
             num_points/(float)SAMPLE_FREQ));
      printf("\nTotal no of QRS complexes detected = %d\n",qrs_num);

/* Print the locations of the R wave fiducial marks and peaks */
      printf("\nbeat\tQRS_f\tQRS_pk\tQRS_t  (s)\n");
      printf("----------------------------------------\n");
      for(i=1; i<(qrs_num+1); i++) {
         printf("%d\t%d\t%d\t%.3f\n",i,qrs_loc[i-1],qrs_pk_loc[i-1],
         ((float)qrs_pk_loc[i-1]/(float) SAMPLE_FREQ));
                                    }
/* In case of rest ECG, calculate avg ST levels and write to argv[4] */
      for(type=1; type<6; type++) {
         printf("\n*********************************************************\n");
         printf("\nBASE PT IS AT R-%d ms, STbegin=R+%d ms, ST=R+%d ms &
                STend=R+%d ms.\n",(BASE*1000/SAMPLE_FREQ),
                (J*1000/SAMPLE_FREQ),(ST*1000/SAMPLE_FREQ),
                ((ST+CAP)*1000/SAMPLE_FREQ));
         printf("\nThe ST resolution is +- %.3f mV (+- %f) wrt body potential.\n",
```

```
ST_SBG_R.C    5-04-88 3:56pm                                          Page 3
            (AD_V_RNG/AD_C_RNG/TAPE_G/ECG_G/2.),
            (AD_V_RNG/AD_C_RNG/TAPE_G/ECG_G/2.));
      if(type==1) printf("\nREST ST_R MEASUREMENTS  (SINGLE POINT)\n");
      if(type==2) printf("\nREST ST_R MEASUREMENTS  (AVERAGE)\n");
      if(type==3) printf("\nREST ST_R MEASUREMENTS  (WEIGHTED AVERAGE)\n");
      if(type==4) printf("\nREST ST_R MEASUREMENTS  (PARABOLIC LS)\n");
      if((type==1)||(type==2)||(type==3)||(type==4)) {
         linear_code = 0;
         printf("\nbt\tstL\tstS\tr_ampl\n");
         printf("\t(mV)\t(mV/s)\t(mV)\n");              }
      if(type==5) {
         linear_code=1;
         printf("\nREST ST_R MEASUREMENTS  (LINEAR LS)\n");
         printf("\nbt\tstL\tstS\tr_coeff\tr_ampl\n");
         printf("\t(mV)\t(mV/s)\t\t(mV)\n");
                 }
      printf("----------------------------------------------------------\n");

      st_rat(type);
      printf("\nAverage rest ST level is %.3f mV.\n\n",rest_st[type-1]);
                              }  /* end for */
      if(w_filecode == 0) {
         printf("\nWriting avg resting ST levels into binary file %s...\n", argv[2]);
         write_b_data(argv[2],1);
         printf("\nWriting trig and feature locations into binary file %s...\n", argv[7]);
         write_b_data(argv[7],2); }
      else {
         printf("\nWriting avg resting ST levels into ascii file %s...\n", argv[2]);
         write_data(argv[2],1);
         printf("\nWriting trig and feature locations into ascii file %s...\n", argv[7]);
         write_data(argv[7],2); }
      goto end;

here:   if(w_filecode == 0) {
         printf("\nWriting avg resting ST levels into binary file %s...\n", argv[2]);
         write_b_data(argv[2],1); }
      else {
         printf("\nWriting avg resting ST levels into ascii file %s...\n", argv[2]);
         write_data(argv[2],1); }

end:    printf("\nEND OF REST ST MEASUREMENTS!\n");
}
/**********************************************************************/
hann(q0,q1,q2,q3,q4)
float q0,q1,q2,q3,q4;
{
    int i;

    for(i=2; i<num_points-2; i++)
       data[i]=(int)(q0 * (float)data_org[i-2] +
                     q1 * (float)data_org[i-1] +
                     q2 * (float)data_org[i] +
                     q3 * (float)data_org[i+1] +
                     q4 * (float)data_org[i+2]);
}
/**********************************************************************/
qrs_pk_find()
{
    int i,j,k,l,r_pk_index,big,dc;
    long sum;
```

```
ST_SBG_R.C    5-04-88 3:56pm                                          Page 4

    qrs_num=big=j=k=0;

/* Store the location index of the qrs fiducial marks */
    for(i=0; i<num_points; i++) {
       if(qrs[i] == 2047) {
         qrs_loc[qrs_num]=i;
         qrs_num++;        }              }

    if(qrs_loc[0]<=QRS_WNDW) {
       r_pk_index=qrs_loc[0];
       qrs_pk_loc[0]=r_pk_index;
       trg_loc[r_pk_index]=1000;
       j=1; }
    if(qrs_loc[qrs_num-1]>=(num_points-QRS_WNDW)) {
       r_pk_index=qrs_loc[qrs_num-1];
       qrs_pk_loc[qrs_num-1]=r_pk_index;
       trg_loc[r_pk_index]=1000;
       k=1; }

/* Find the location index of the peaks of the qrs complex */
    for(i=j; i<qrs_num-k; i++)          {
       sum=0;
       r_pk_index = qrs_loc[i];

       for(l=qrs_loc[i]-QRS_WNDW; l<(qrs_loc[i]+QRS_WNDW+1); l++)
           sum += data[l];
       dc = sum / (long)(2*QRS_WNDW+1);

       for(l=qrs_loc[i]-QRS_WNDW; l<(qrs_loc[i]+QRS_WNDW+1); l++)
            if(abs(data[l]-dc) >= big) {
               big=abs(data[l]-dc);
               r_pk_index = l;    }
       big=0;
       trg_loc[r_pk_index]=1000;
       qrs_pk_loc[i]=r_pk_index;   }
}
/**********************************************************************/
st_rat(t)
int t;
{
    int     s;
    int     base_cent,st_cent,j_point,qrs_pk,beat,i,j;
    long    sigma_x,sigma_x2,sigma_y,sigma_xy,x,avg_x;
    float   base_slp,base_incp,st_lvl_mv,st_slp_mv,st_lvl_avg,st_slp_avg,
            st_slp,st_incp,base,st,r_ampl,st_lvl_sum,st_slp_sum;
    double  r,r1,r2,r3,avg_y,temp,temp1,temp2;

    st_lvl_sum = st_slp_sum = 0.;

    for(i=0;i<qrs_num; i++)              {
       beat=i+1;
       qrs_pk=qrs_pk_loc[i];
       base_cent=qrs_pk-BASE;
       st_cent=qrs_pk+ST;
       j_point=qrs_pk+J;
/*
    for(s=base_cent-2; s<(base_cent+3); s++)
       printf("base_dat[s]=%d\n",data[s]);
    printf("\n");
```

```
ST_SEG_R.C    3-04-88 3:56pm                                        Page 5
     for(s=j_point; s<(st_cent+3); s++)
        printf("st_dat[s]=%d\n",data[s]);
*/
        switch(t) {
        case 1 : /**************** SINGLE-POINT ST *********************/
        st_lvl_mv=(float)(data[st_cent]-data[base_cent])
                  *AD_V_RNG/AD_C_RNG/TAPE_G/ECG_G-rest_st[0];
/*
        st_slp_mv=(float)(data[st_cent+FIT]-data[st_cent-FIT])
                  /(2.*FIT)*AD_V_RNG/AD_C_RNG/TAPE_G/ECG_G*(float)SAMPLE_FREQ;
*/
        st_slp_mv=(float)(data[st_cent+CAP]-data[j_point])/(ST+CAP-J)*AD_V_RNG/AD_C_RNG/
                  TAPE_G/ECG_G*(float)SAMPLE_FREQ;

        r_ampl=(float)(data_org[qrs_pk]-data[base_cent])*AD_V_RNG/AD_C_RNG/TAPE_G
              /ECG_G;
        break;

        case 2 : /**************** AVERAGE ST ****************/
        base=(float)(data[base_cent-2]+data[base_cent-1]+data[base_cent]
             +data[base_cent+1]+data[base_cent+2])/5.;
        st=(float)(data[st_cent-2]+data[st_cent-1]+data[st_cent]
           +data[st_cent+1]+data[st_cent+2])/5.;
        st_lvl_mv = (st-base)*AD_V_RNG/AD_C_RNG/TAPE_G/ECG_G-rest_st[1];
/*
        st_slp_mv = (float)(data[st_cent+FIT]-data[st_cent-FIT])/(2.*FIT)
                  *AD_V_RNG/AD_C_RNG/TAPE_G/ECG_G*(float)SAMPLE_FREQ;
*/
        st_slp_mv=(float)(data[st_cent+CAP]-data[j_point])/(ST+CAP-J)*AD_V_RNG/AD_C_RNG/
                  TAPE_G/ECG_G*(float)SAMPLE_FREQ;

        r_ampl=((float)data_org[qrs_pk]-base)*AD_V_RNG/AD_C_RNG/TAPE_G/ECG_G;
        break;

        case 3 : /**************** WEIGHTED AVERAGE ST *************/
                 /****************(0.1,0.2,0.4,0.2,0.1)*************/
        base=(0.1*(float)data[base_cent-2]+0.2*(float)data[base_cent-1]
             +0.4*(float)data[base_cent]+0.2*(float)data[base_cent+1]
             +0.1*(float)data[base_cent+2]);
        st=(0.1*(float)data[st_cent-2]+0.2*(float)data[st_cent-1]+
           0.4*(float)data[st_cent]+0.2*(float)data[st_cent+1]+
           0.1*(float)data[st_cent+2]);
        st_lvl_mv = (st-base)*AD_V_RNG/AD_C_RNG/TAPE_G/ECG_G-rest_st[2];
/*
        st_slp_mv = (float)(data[st_cent+FIT]-data[st_cent-FIT])/(2.*FIT)
                  *AD_V_RNG/AD_C_RNG/TAPE_G/ECG_G*(float)SAMPLE_FREQ;
*/
        st_slp_mv=(float)(data[st_cent+CAP]-data[j_point])/(ST+CAP-J)*AD_V_RNG/AD_C_RNG/
                  TAPE_G/ECG_G*(float)SAMPLE_FREQ;

        r_ampl=((float)data_org[qrs_pk]-base)*AD_V_RNG/AD_C_RNG/TAPE_G/ECG_G;
        break;

        case 4 : /**************** PARABOLIC LS ST ****************/
        base=(-3.*(float)data[base_cent-2]+12.*(float)data[base_cent-1]+
             17.*(float)data[base_cent]+12.*(float)data[base_cent+1]-
             3.*(float)data[base_cent+2])/35.;
        st=(-3.*(float)data[st_cent-2]+12.*(float)data[st_cent-1]+
           17.*(float)data[st_cent]+12.*(float)data[st_cent+1]-
           3.*(float)data[st_cent+2])/35.;
```

```
ST_SEG_R.C    3-04-88 3:56pm                                        Page 6
        st_lvl_mv = (st-base)*AD_V_RNG/AD_C_RNG/TAPE_G/ECG_G-rest_st[3];

        st_slp_mv=(-5.*(float)data[st_cent+CAP-10]-4.*(float)data[st_cent+CAP-9]
                  -3.*(float)data[st_cent+CAP-8]-2.*(float)data[st_cent+CAP-7]
                  -(float)data[st_cent+CAP-6]+(float)data[st_cent+CAP-4]
                  +2.*(float)data[st_cent+CAP-3]+3.*(float)data[st_cent+CAP-2]
                  +4.*(float)data[st_cent+CAP-1]+5.*(float)data[st_cent+CAP])
                  /110.*AD_V_RNG/AD_C_RNG/TAPE_G/ECG_G*(float)SAMPLE_FREQ;
/*
        st_slp_mv=(-2.*(float)data[st_cent-2]-(float)data[st_cent-1]
                  +(float)data[st_cent+1]+2.*(float)data[st_cent+2])
                  /10.*AD_V_RNG/AD_C_RNG/TAPE_G/ECG_G*(float)SAMPLE_FREQ;
*/
        r_ampl=((float)data_org[qrs_pk]-base)*AD_V_RNG/AD_C_RNG/TAPE_G/ECG_G;
        break;

        case 5 : /**************** LINEAR LS ST ********************/
        base_slp=base_incp=0.;
        x=sigma_x=sigma_x2=sigma_y=sigma_xy=0;
        for(j=base_cent-FIT; j<(base_cent+FIT+1); j++) {
           sigma_y += (long)data[j];
           sigma_xy += ((long)data[j] * x);
           sigma_x += x;
           sigma_x2 += sqr(x);
           x++;                                       }
        avg_y = (double)sigma_y/(double)(2*FIT+1);
        avg_x = sigma_x / (2*FIT+1);
        base_slp=(float)((double)(2*FIT+1)*(double)sigma_xy-sigma_x*(double)sigma_y)
                 /((double)(2*FIT+1)*sigma_x2 - sqr(sigma_x));
        base_incp=(float)(avg_y-(double)avg_x*(double)base_slp);
        base = base_slp*(float)avg_x + base_incp;

        x=sigma_y=sigma_xy=0;
        st_slp=st_incp=0.;
        for(j=st_cent-FIT;j<(st_cent+FIT+1); j++)      {
           sigma_y += (long)data[j];
           sigma_xy += ((long)data[j]*x);
           x++;                                        }
        avg_y = (double) sigma_y / (double)(2*FIT+1);

        st_slp_mv=(float)((double)(2*FIT+1)*(double)sigma_xy-sigma_x*(double)sigma_y)
                  /((double)(2*FIT+1)*sigma_x2-sqr(sigma_x));
        st_incp=(float)(avg_y-(double)avg_x*(double)st_slp_mv);
        st = st_slp_mv * (float)avg_x + st_incp;
        st_lvl_mv=(st-base)*AD_V_RNG/AD_C_RNG/TAPE_G/ECG_G-rest_st[4];

        x=sigma_x=sigma_x2=sigma_y=sigma_xy=0;
        for(j=j_point;j<(st_cent+CAP+1); j++)      {
           sigma_y += (long)data[j];
           sigma_xy += ((long)data[j]*x);
           sigma_x += x;
           sigma_x2 += sqr(x);
           x++;                                    }
        avg_y = (double) sigma_y / (double)(st_cent+CAP-j_point+1);
        avg_x = sigma_x / (st_cent+CAP-j_point+1);

        r = r1 = r2 = r3 = 0.;
        temp = temp1 = temp2 = 0.;
        n = 0;
        for(j=j_point; j<(st_cent+CAP+1); j++)      {
```

```
ST_SEG_R.C    5-04-88 3:56pm                                    Page 7
            temp1 = (double)(s-avg_x);
            temp2 = (double)data[j] - avg_y;
            r1 += (temp1 * temp2);
            r2 += sqr(temp1);
            r3 += sqr(temp2);
            s++;                                   }
        temp = r2 * r3;
        if (temp == 0.)
            r = 0.;
        else
            r = r1 / sqrt(temp);

        st_slp_mv=(float)((double)(st_cent+CAP-j_point+1)*(double)sigma_xy-(double)sigma_x
                    *(double)sigma_y)/((double)(st_cent+CAP-j_point+1)*(double)sigma_x2-
                    (double)sqr(sigma_x));
        st_slp_mv = st_slp_mv * AD_V_RNG/AD_C_RNG/TAPE_G/ECG_G*
                      (float)SAMPLE_FREQ;

        r_ampl=((float)data_org[qrs_pk]-base)*AD_V_RNG/AD_C_RNG/TAPE_G/ECG_G;
        break;     }

/*  Denote the pr, j, and st points in trig file */
    trg_loc[base_cent]=trg_loc[st_cent]=-750;
    trg_loc[j_point]=trg_loc[st_cent+CAP]=-500;

/*  Calculate the sum of ST level and slope */
        st_lvl_sum += st_lvl_mv;
        st_slp_sum += st_slp_mv;

/*  Report the results */
    if(linear_code==0)
         printf("%d\t%.3f\t%.3f\t%.3f\n",beat,st_lvl_mv,st_slp_mv,r_ampl);

    if(linear_code==1)
         printf("%d\t%.3f\t%.3f\t%.2f\t%.3f\n",beat,st_lvl_mv,st_slp_mv,
                r,r_ampl);
                                            }
    printf("\nThe sum of %d rest st levels is %.3f mV.\n",qrs_num,st_lvl_sum);
    rest_st[t-1]=(st_lvl_sum/(float)qrs_num);
}
/*********************************************************************/
read_data(infile,code)
char *infile;
int  code;
{
      int   i,temp,check;
      FILE *fpi;

      if((fpi=fopen(infile,"r")) == NULL) {
           printf("error -> unable to open input ascii file %s.\n",infile);
           exit(1);                        }
      if (code == 1) {
         for(i=0; ((fscanf(fpi,"%d",&temp)!=EOF) && (i<MAXNUM)); i++)
            qrs[i] = temp;            }
      if (code == 2) {
         for(i=0; (fscanf(fpi,"%d",&temp) != EOF) && (i<MAXNUM); i++)
            data_org[i] = temp;
            num_points = i;           }

      check = fclose(fpi);
```

```
ST_SEG_R.C    5-04-88 3:56pm                                    Page 8
      if(check != 0) {
         printf("error -> unable to close input ascii file %s.\n",infile);
         exit(1);     }
}
/*********************************************************************/
read_b_data(infile,code)
char *infile;
int  code;
{
      int   i,check;
      FILE  *fpi;

      if((fpi=fopen(infile,"rb")) == NULL) {
           printf("error -> unable to open input binary file %s.\n",infile);
           exit(1);                        }

      if (code == 1)
         for(i=0; i<MAXNUM && !feof(fpi); i++)
            qrs[i]=(int)getw(fpi);

      else if (code == 2) {
         for(i=0; i<MAXNUM && !feof(fpi); i++)
            data_org[i]=(int)getw(fpi);
         num_points=i;     }

      else { printf("\nWrong code for read binary (1-2)!\n"); exit(1); }

      check = fclose(fpi);
      if(check != 0) {
         printf("error -> unable to close input binary file %s.\n",infile);
         exit(1);     }
}
/*********************************************************************/
write_data(outfile,code)
char *outfile;
int code;
{
      int i,check;
      FILE *fpo;

      if((fpo = fopen(outfile,"w")) == NULL) {
         printf("error -> unable to open output ascii file %s.\n",outfile);
         exit(1);                            }

      if(code==1)
         for(i=0; i<5; i++)
            fprintf(fpo,"%.3f%c",rest_st[i],' ');

      if(code==2)
         for(i=0; i<num_points; i++)
            fprintf(fpo,"%6d%c",trg_loc[i],(i%10==9 ? '\n' : ' '));

      check = fclose(fpo);
      if(check != 0) {
         printf("error -> unable to close output ascii file %s.\n",outfile);
         exit(1);
                   }
}
/*********************************************************************/
write_b_data(outfile,code)
```

```
char *outfile;
int code;
{
      int i,check;
      FILE *fpo;

      if((fpo = fopen(outfile,"wb")) == NULL) {
         printf("error -> unable to open output binary file %s.\n",outfile);
         exit(1);                               }

      if(code==1)
         fwrite(rest_st,sizeof(float),5,fpo);

      if(code==2)
         fwrite(try_loc,sizeof(int),num_points,fpo);

      check = fclose(fpo);
      if(check != 0) {
         printf("error -> unable to close output binary file %s.\n",outfile);
         exit(1);    }
}
```

INVERSE.C 4-28-88 7:04am Page 1

```
/*************************************************************************
 This program is the top level program for computer equalization of
 low frequency components of signals that have been high-pass filtered.
 This program calls the programs CUT, EQUAL, and PASTE.

 Usage: inverse <name> <tau>
        <name> is the base name of distorted and restored files,
        eg: distorted disk file=HJ100DIS, restored disk file=HJ100RES
            then <name>=HJ100
        <tau> is the RC time constant of HPF in ms.

 For proper operation provide the name of the distorted file exactly
 as specified above, i.e. provide HJ100 to INVERSE (do not exceed 5
 characters for base name) with HJ100DIS in the disk directory.  The
 restored file will be written into HJ100RES

Author: Hossein Jadvar
Date:   June 1988
*************************************************************************/
#include <stdio.h>
#include <stdlib.h>

main(argc,argv)
int argc;
char *argv[];
{
        int i;
        char name[13], line[128];
        FILE *fp;
        double tau;
/*
        tau = atof(argv[2]);
*/
        if(argc!=3) {
                printf("\nUsage: inverse <name> <tau>\n");
                printf("<name> is base name of distorted or restored file\n");
                printf("eg: use HJ100 when distorted disk file is HJ100DIS\n");
                printf("<tau> is the RC time constant of the HPF in ms.\n\n");
                exit(1); }

        sprintf(line,"cut %sdis 0.5 250",argv[1]);
        puts(line); system(line);

        for(i=1;;i++) {
                sprintf(name,"%sdis.%d",argv[1],i);
                if((fp=fopen(name,"rb"))==NULL) { --i; break; }
                else fclose(fp);
                sprintf(line,"equal junk %sdis.%d %sres.%d 0 0 2 14.7 junk",
                        argv[1], i, argv[1], i);
                puts(line); system(line);
                }

        sprintf(line,"paste %sres %d 0 1",argv[1],i);
        puts(line); system(line);

        sprintf(line,"ren %sdis %sds",argv[1],argv[1]);
        system(line);
        sprintf(line,"ren %sres.tot %srs",argv[1],argv[1]);
        system(line);
        sprintf(line,"del %sdis.*",argv[1]);
```

INVERSE.C 4-28-88 7:04am Page 2

```
        system(line);
        sprintf(line,"del %sres.*",argv[1]);
        system(line);
        sprintf(line,"ren %sds %s_ev.dis",argv[1],argv[1]);
        system(line);
        sprintf(line,"ren %srs %s_ev.res",argv[1],argv[1]);
        system(line);
}
```

```
CUT.C    4-27-88 7:16pm                                              Page 1
/*********************************************************************
 This program cuts a data array of maximum length 32767 samples
 (131 s at 250 Hz) into pieces of <len> second.

 Usage: cut <name> <len> <sample_freq>

        <name> is the name of the file (w/o extension) to be cut into ...
        <name.1> <name.2> .... <name.n>

 Author: Hossein Jadvar
 Date:   May 1988
*********************************************************************/
#include <stdio.h>
#include <stdlib.h>
#include <string.h>

#define  MAXNUM 32767

int data_piece[MAXNUM], data[MAXNUM];
int tot_num_points;

main(argc,argv)
int argc;
char *argv[];
{
   int i,num_of_file,length,sample_freq;
   char buff[5],*pbuff;
   char string[15],template[15],*io_file;

   tot_num_points=0;

   if(argc!=4) {
     printf("\nUsage: cut <name> <len> <sample_freq>\n");
     printf("<len in seconds> & <name.1> <name.2> .... <name.n> will be created.\n");
     exit(1);  }

   sample_freq=atoi(argv[3]);
   length=(int)((float)atof(argv[2])*(float)sample_freq);

   strcpy(template,argv[1]);
   io_file=strcat(template,".");
   strcpy(string,template);

   printf("\nReading the file %s ...\n",argv[1]);
   read_b_data(length,argv[1]);
   num_of_file=tot_num_points/length;
   printf("\n%d files each w/ %d points will be created.\n",num_of_file,length);

   for(i=1; i<num_of_file+1; i++) {
     pbuff=itoa(i,buff,10);
     io_file=strcat(string,pbuff);
     printf("\nWriting %d points into file %s ...\n",length,io_file);
     write_b_data(length,(i-1),io_file);
     strcpy(string,template);
   }
   printf("\nEnd of cutting!\n");
}
/*********************************************************************/
read_b_data(length,infile)
int length;
```

```
CUT.C    4-27-88 7:16pm                                              Page 2
char *infile;
{
      int   i,check;
      FILE  *fpi;

      if((fpi=fopen(infile,"rb")) == NULL) {
           printf("error -> unable to open input binary file %s\n",infile);
           exit(1);  }

      for(i=0; i<MAXNUM && !feof(fpi); i++)
           data[i]=(int)getw(fpi);
      tot_num_points=i-1;
      printf("\ntotal no of points read = %d\n",tot_num_points);

      if((tot_num_points%length)!=0) {
           for(i=0; i<length-(tot_num_points%length); i++)
                data[tot_num_points+i]=0;
           printf("\n%d zero points padded to make an array of %d points\n",
                  (length-(tot_num_points%length)),tot_num_points+(length-
                  (tot_num_points%length)));
           tot_num_points += (length-(tot_num_points%length)); }

      check = fclose(fpi);
      if(check != 0) {
         printf("error -> unable to close input binary file %s\n",infile);
         exit(1);    }
}
/*********************************************************************/
write_b_data(length,index,outfile)
int length,index;
char *outfile;
{
      int i,check;
      FILE *fpo;

      if((fpo = fopen(outfile,"wb")) == NULL) {
         printf("error -> unable to open output binary file %s\n",outfile);
         exit(1);                              }

      for(i=0; i<length; i++)
         putw(data[i+index*length],fpo);

      check = fclose(fpo);
      if(check != 0) {
         printf("error -> unable to close output binary file %s\n",outfile);
         exit(1);    }
}
```

```
PASTE.C   4-27-88 1:53am                                          Page 1
/*********************************************************************
 This program pastes together pieces of data of any length.  The
 maximum length of any piece or the total length of the final
 resultant array is limited to 32767 samples (131 s at 250 Hz).
 The baseline discontinuities between consecutive pieces are taken
 care of by adding the discontinuity to all data points of the last
 piece.

 Usage: paste <name> <num_of_file> <dc_ndc(1/0)> <satcode(ON/1T)>

        <name> is the name of the files to be pasted in the form
        <name.1> <name.2> ... <name.n>

        <num_of_file> is the number of files to be pasted.
        <dc_ndc(0/1)>: 1 no dc filter, 1 dc filter
        <satcode(ON/1T)>: 0 data[i]>2047 --> data[i]=data[i-1]
                          1 data[i]<-2047 --> data[i]=data[i-1]

 In this form, the final array will be written into disk file <name.tot>

 Author: Hossein Jadvar
 Date:   April 1988
*********************************************************************/
#include <stdio.h>
#include <stdlib.h>
#include <string.h>

#define  TRUE   0
#define  FALSE  1
#define  MAXNUM 32767

int data_piece[MAXNUM], data[MAXNUM];
long num_points,tot_num_points,diff;

main(argc,argv)
int argc;
char *argv[];
{
   int i,num_of_file,code,dccode,satcode;
   char buff[5],*pbuff;
   char string[15],template[15],*io_file;

   tot_num_points=0;

   if(argc!=5) {
     printf("\nUsage: paste <name> <num_of_file> <dc_ndc(1/0)> <satcode(ON\\1T)>\n");
     printf("<name.1> <name.2> .... <name.n> and n=<num_of_file>\n");
     printf("Pasted data in <name.tot>\n");
     exit(1);  }

   num_of_file=atoi(argv[2]);
   dccode=atoi(argv[3]);
   satcode=atoi(argv[4]);

   strcpy(template,argv[1]);
   io_file=strcat(template,".");
   strcpy(string,template);

   for(i=1; i<num_of_file+1; i++) {
     pbuff=itoa(i,buff,10);
```

```
PASTE.C   4-27-88 1:53am                                          Page 2
     io_file=strcat(string,pbuff);
     printf("\nReading the file %s ...\n",io_file);
     read_b_data(io_file);
     code=paste_data(satcode);
     if(code==FALSE) {
       printf("Reached the max no. (32767) of data points allowd.\n");
       break; }
     else
       printf("Pasting %ld points, baseline discontinuity=%ld\n",num_points,diff);
     strcpy(string,template);
   }
   if(dccode==1) dc_filter();
   io_file=strcat(string,"tot");
   printf("\nWriting %ld points into file %s ...\n",tot_num_points,io_file);
   write_b_data(io_file);
   printf("\nEnd of pasting!\n");
}
/*********************************************************************/
paste_data(satcode)
int satcode;
{
   long i;

   if((tot_num_points+num_points) > MAXNUM) {
     num_points=MAXNUM-tot_num_points;
     if(num_points==0) return FALSE;        }

   if(tot_num_points==0) diff=0;
   else diff=data[tot_num_points-1]-data_piece[0];

   for(i=0; i<num_points; i++)    {
     data[i+tot_num_points]=(int)((long)data_piece[i]+diff);

   if(satcode==1) {
     if(data[i+tot_num_points]>2047)
        data[i+tot_num_points]=data[i+tot_num_points-1];
     else if(data[i+tot_num_points]<-2047)
        data[i+tot_num_points]=data[i+tot_num_points-1];
                  }
/*
     printf("i=%ld\tdata_po=%d\tdata=%d\tdiff=%ld\n",(i+tot_num_points),data_piece[i],
     data[i+tot_num_points],diff);
*/                                 }
   tot_num_points += num_points;
   return TRUE;
}
/*********************************************************************/
dc_filter()
{
   int i;
   long sum,mean;

   for(i=0;i<tot_num_points;i++)
     sum += (long)data[i];
   mean = sum/(long)tot_num_points;
   printf("\nmean (dc value) = %ld\n",mean);
   for(i=0; i<tot_num_points; i++)
     data[i] -= (int)mean;
}
/*********************************************************************/
```

```
read_b_data(infile)
char *infile;
{
      int   i,check;
      FILE  *fpi;

      if((fpi=fopen(infile,"rb")) == NULL) {
           printf("error -> unable to open input binary file %s\n",infile);
           exit(1);  }

      for(i=0; i<MAXNUM && !feof(fpi); i++)
           data_piece[i]=(int)getw(fpi);
      num_points=(long)i-1;

      check = fclose(fpi);
      if(check != 0) {
         printf("error -> unable to close input binary file %s\n",infile);
         exit(1);    }
}
/*********************************************************************/
write_b_data(outfile)
char *outfile;
{
      int i,check;
      FILE *fpo;

      if((fpo = fopen(outfile,"wb")) == NULL) {
         printf("error -> unable to open output binary file %s\n",outfile);
         exit(1);                          }

      for(i=0; i<tot_num_points; i++)
         putw(data[i],fpo);

/*    fwrite(data,sizeof(int),tot_num_points,fpo); */

      check = fclose(fpo);
      if(check != 0) {
         printf("error -> unable to close output binary file %s\n",outfile);
         exit(1);    }
}
```

```
EQUAL.C   4-27-88 7:11pm                                              Page 1
/*****************************************************************************
 This program equalizes the low-frequency components of electrocardiographic
 data which have been recorded with a HPF greater than 0.05 Hz.  Equalization
 of these components is important in ST segment measurements.

 Usage: equal erg_f filt_f res_f r_B_A w_B_A integ_code tau dcf_erg_f

        erg_f: the erg undistorted file (use JUNK)
        filt_f: distorted file
        res_f: writing the restored file
        r_B_A: 0 for binary input file, 1 for ascii
        w_B_A: 0 for binary output file, 1 for ascii
        integ_code: 0 trps, 1 simpson, 2 bilinear, 3 differential, 4 MacPC
        tau: RC of the HPF in ms
        dcf_erg_f: writing the dc filtered erg undistorted file (use JUNK)

 Author: Hossein Jadvar
 Date:   March 1988
*****************************************************************************/
#include <stdio.h>
#include <stdlib.h>

#define MAXNUM          16383 /* 16383 (64KB) float data (4 bytes)=65.53 s at 250 Hz */
#define SAMPLE_FREQ     250.
#define BETA            0.314 /* 0.05 Hz * 2pi */
#define sqr(x)          x * x

int     num_points,r_filecode,w_filecode,integ_code;
int     temp_in[MAXNUM],temp_out[MAXNUM];
float   data_in[MAXNUM],data_out[MAXNUM],data_res[MAXNUM];
float   data_integ[MAXNUM],temp1[MAXNUM];
float   ALPHA,C1,C2,C3,D1,D2;

main(argc,argv)
int argc;
char *argv[];
{
       int      i;
       float    diff,err;
       float    c1,c2,c3,c4;

      if (argc != 9) {
        printf("\nUsage: equal erg_f filt_f res_f r_B_A w_B_A integ_code tau dcf_erg_f\n");
        printf("        erg_f: the erg undistorted file (JUNK)\n");
        printf("        filt_f: distorted file \n");
        printf("        res_f: the restored file\n");
        printf("        r_B_A: 0 for binary input file, 1 for ascii\n");
        printf("        w_B_A: 0 for binary output file, 1 for ascii\n");
        printf("        integ_code: 0 trps, 1 simp, 2 bilin, 3 diffr, 4 MacPC\n");
        printf("        tau: RC of the HPF in ms.\n");
        printf("        dcf_erg_f: writing dc filtered erg undist file (JUNK)\n");
        exit(1);      }

       r_filecode = atoi(argv[4]);
       w_filecode = atoi(argv[5]);
       integ_code = atoi(argv[6]);
       ALPHA = 1000./(float)atof(argv[7]);
       err=0.;
       c1=2.-(BETA/SAMPLE_FREQ);
       c2=2.+(BETA/SAMPLE_FREQ);
```

```
EQUAL.C   4-27-88 7:11pm                                              Page 2
       c3=2.+(ALPHA/SAMPLE_FREQ);
       c4=2.-(ALPHA/SAMPLE_FREQ);
       C1=c1/c2;    C2=c3/c2;    C3=c4/c2;
       D1=1./(1.+(BETA/SAMPLE_FREQ));
       D2=(1.+(ALPHA/SAMPLE_FREQ))*D1;

/*
       printf("\nr_code=%d\tw_code=%d\tinteg=%d\talpha=%f\n",r_filecode,
               w_filecode,integ_code,(1000./alpha));
       read_in(argv[1],r_filecode,1);
*/
       read_in(argv[2],r_filecode,2);
/*
       printf("\ndc filtering the original signal...\n");
       do_filter(1);

       printf("\nWriting the dc filtered undistorted signal into %s.\n",
               argv[8]);
       write_out(data_in,argv[8]);
*/
       printf("\ndc filtering the distorted signal...\n");
       do_filter(2);
/*
       printf("\nSmoothing the dc filtered distorted signal...\n");
       hann(0.125,0.25,0.25,0.25,0.125);
*/
       if(integ_code==0) {
         printf("\nIntegrating the dc filtered distorted signal...(Trapezoid).\n");
         integ_trps(); }
       else if(integ_code==1) {
         printf("Integrating the dc filtered distorted signal...(Simpson).\n");
         integ_simp(); }
       else if(integ_code==2) {
         printf("Using bilinear transformation...\n");
         bilin();
         goto here; }
       else if(integ_code==3) {
         printf("Using differential transformation method...\n");
         diffr();
         goto here; }
       else if(integ_code==4) {
         printf("Using the Mac PC method...\n");
         macpc();
         goto here; }
       else
         printf("\nWrong integ_code. (1-4).\n");
/*
       printf("\ndc filtering the integral signal...\n");
       do_filter(3);
*/
       printf("\nAdding the distorted signal and its weighted integral...\n");
       for(i=0; i<num_points; i++) {
/*       printf("data_out=%f\tdata_integ=%f\n",data_out[i],data_integ[i]); */
         data_res[i] = data_out[i] + data_integ[i];   }

here:  printf("\ndc filtering the restored signal...\n");
       do_filter(4);

       printf("\nWriting the restored data in file %s.\n",argv[3]);
       write_out(data_res,argv[3]);
```

```
EQUAL.C   4-27-88 7:13pm                                                    Page 3
/*
       for(i=1; i<num_points; i++) {
          diff=data_in[i]-data_res[i];
          printf("d_in=%.3f\td_res=%.3f\tdiff=%.3f\n",data_in[i],data_res[i],diff);
          err +=  sqr(diff); }

       printf("ALPHA=%f\tLS ERR=%f\n",ALPHA,err);
*/
       printf("\nEND OF LOW-FREQUENCY EQUALIZATION...\n");
}
/*************************************************************************/
dc_filter(code)
int code;
{
    int i;
    float  sum,avg,temp;

    sum=avg=0.;
    for(i=0; i<num_points; i++) {
       if(code==1)
          sum += data_in[i];
       else if(code==2)
          sum += data_out[i];
       else if(code==3)
          sum += data_integ[i];
       else
          sum += data_res[i];    }

    avg = sum/(float)num_points;
    printf("dc = %f\n",avg);

    for(i=0; i<num_points; i++) {
       if(code==1) {
          temp = data_in[i];
          data_in[i] -= avg;
/*        printf("data_in=%f\tdata_in_dc=%f\n",temp,data_in[i]); */
                                   }
       else if(code==2)  {
          temp = data_out[i];
          data_out[i] -= avg;
/*        printf("data_out=%f\tdata_out_dc=%f\n",temp,data_out[i]); */
                                   }
       else if(code==3)  {
          temp=data_integ[i];
          data_integ[i] -= avg;
/*        printf("data_integ=%f\tdata_integ_dc=%f\n",temp,data_integ[i]); */
                                   }
       else {
          temp=data_res[i];
          data_res[i] -= avg;
/*        printf("data_res=%f\tdata_res_dc=%f\n",temp,data_res[i]); */
          }
                                   }
}
/*************************************************************************/
integ_trps()
{
    int i;

    for(i=1; i<num_points; i++) {
```

```
EQUAL.C   4-27-88 7:13pm                                                    Page 4
       data_integ[i]=data_integ[i-1]+data_out[i-1]
                  +(ALPHA*0.5/SAMPLE_FREQ)*(data_out[i]-data_out[i-1]);
/*     printf("data_out=%f\tdata_integ=%f\n",data_out[i],data_integ[i]);*/
                                   }
}
/*************************************************************************/
integ_simp()
{
    int i;

    for(i=2; i<num_points; i++)
       data_integ[i]=data_integ[i-2]+0.333*(data_out[i]+
                     4.*data_out[i-1]+data_out[i-2]);
}
/*************************************************************************/
bilin()
{
    int i;

    printf("\nC1=%.3f\tC2=%.3f\tC3=%.3f\n",C1,C2,C3);
    for(i=1;i<num_points; i++) {
       data_res[i]=(C1*data_res[i-1])+(C2*data_out[i])-(C3*data_out[i-1]);
/*     printf("data_res[%d]=%d\n",i,(int)data_res[i]);*/ }
}
/*************************************************************************/
diffr()
{
    int i;

    printf("\nD1=%.3f\tD2=%.3f\n",D1,D2);
    for(i=1; i<num_points; i++) {
       data_res[i]=(D1*data_res[i-1])+(D2*data_out[i])-(D1*data_out[i-1]);
/*     printf("data_res[%d]=%d\n",i,(int)data_res[i]); */ }
}
/*************************************************************************/
macpo()
{
    int i;

    for(i=1; i<num_points; i++) {
       data_res[i]=data_out[i]+data_integ[i-1]*ALPHA/SAMPLE_FREQ;
       data_integ[i]=data_integ[i-1]+data_out[i]; }
}
/*************************************************************************/
hann(q0,q1,q2,q3,q4)
float q0,q1,q2,q3,q4;
{
    int i;

    for(i=4; i<num_points; i++)
       temp1[i]=data_out[i-4]*q0+data_out[i-3]*q1+data_out[i-2]*q2
                +data_out[i-1]*q3+data_out[i]*q4;

    for(i=4; i<num_points; i++)
       data_out[i]=temp1[i];
}
/*************************************************************************/
read_in(infile,frcode,num_file)
int  num_file,frcode;
char *infile;
```

```
EQUAL.C    4-27-88 7:11pm                                        Page 5
{
   int i, check;
   int temp;
   FILE *fpi;
   float *data;

   data = num_file==1 ? data_in : data_out;

   if (freade == 1)    {
      if ((fpi=fopen(infile, "r")) == NULL)
      {
        printf("error -> unable to open input ascii file %s.\n",infile);
        exit(1);
      }
      printf("\nReading the input ascii file %s...\n",infile);
      for(i=0; (fscanf(fpi,"%f", &data[i]) != EOF) && (i < MAXNUM); i++)
/*      printf("data[%d] = %f\n",i,data[i]);*/

      num_points = i; }

   else {
      if ((fpi=fopen(infile, "rb")) == NULL)
      {
        printf("error -> unable to open input binary file\n",infile);
        exit(1);
      }
      printf("\nReading the input binary file %s...\n",infile);

      for (i=0; i<MAXNUM && !feof(fpi); i++) data[i] = (float)getw(fpi);
      num_points = i-1;
      printf("\nRead completed. %d data points read from file %s.\n",num_points,infile);
        }

   check=fclose(fpi);
   if (check != 0)
      {
      printf("error -> unable to close input file\n");
      exit(1);
      }
}
/***********************************************************************/
write_out(data, outfile)
float data[];
char *outfile;
{
    int i,check;
    FILE *fpo;

    if((fpo=fopen(outfile,"wb"))==NULL) {
       printf("error -> unable to open output binary file %s.\n");
       exit(1);     }

    for(i=0; i<num_points; i++) {
/*     if(data[i]>2047 || data[i]<-2047) data[i]=data[i-1]; */
       putw((int)data[i],fpo);   }

    check=fclose(fpo);
    if(check!=0) {
       printf("error -> unable to close output binary file %s\n");
       exit(1);  }
```

```
EQUAL.C    4-27-88 7:11pm                                        Page 6
}
```

What is claimed is:

1. A method of automatically detecting a selected posterior heart condition in a person comprising:

positioning a sensing electrode adjacent a posterior surface of the person's heart;

electrically stressing the heart;

detecting electrical signals from the electrode that have been generated in response to stressing the heart irrespective of the presence of stressing induced artifacts;

filtering the detected signals;

automatically locating a local maximum of the filtered signals;

automatically measuring selected regions of the filtered signals adjacent the local maximum; and generating an indicium indicative of the presence or absence of the selected posterior heart condition.

2. A method as in claim 1 with the step of stressing including:

stressing the heart in response to exercise by the person.

3. A method as in claim 1 including:

positioning at least one stressing electrode adjacent the posterior surface of the heart.

4. A method as in claim 3 including:

providing a selected electrical signal to the stressing electrode thereby stressing the heart in response thereto while suppressing artifacts generated by the selected electrical signal.

5. A method as in claim 3 with said measuring step including:

automatically determining the corresponding values of the filtered signals adjacent the local maximum; and comparing the corresponding values.

6. An apparatus for automatically detecting a selected posterior heart condition in a person comprising:

electrode means, positionable in the person's esophagus adjacent a posterior surface of the person's heart, for sensing electrical signals generated by the heart;

means for electrically stressing the heart;

means for detecting electrical signals from said electrode means that have been generated in response to stressing the heart;

means for recording the detected signals essentially simultaneously with said stressing;

means for processing the detected, recorded, signals;

means for automatically measuring selected regions of the processed signals; and means for generating an indicium indicative of the presence or absence of the selected posterior heart condition.

7. An apparatus as in claim 6 including:

stressing electrode means positionable adjacent the posterior surface of the heart.

8. An apparatus as in claim 7 including:

means for providing a selected electrical signal to said stressing electrode means so as to stress the heart in response thereto.

9. An apparatus as in claim 6 including:

means for filtering the detected electrical signals prior to processing same.

10. An apparatus as in claim 6 with said measuring means including means for measuring selected portions of the processed signals corresponding to an ST segment thereof.

11. An apparatus as in claim 6 with said measuring means including:

means for locating a first region of the processed signal;

means for locating second and third regions, displaced from the first region;

means for determining the corresponding values of a processed signal at the second and third regions; and means for comparing the corresponding values.

12. An apparatus as in claim 11 with said first region locating means including means for identifying a local maximum value of said detected electrical signals.

13. An apparatus as in claim 12 including means for locating said second and third regions on the order of 60 multi-seconds prior to said local maximum and 80 milliseconds after same.

14. An apparatus as in claim 6 including means for suppressing selected stressing related electrical noise signals.

15. An apparatus as in claim 6 with said electrode means including a swallowable body portion.

16. A method of non-invasively and automatically detecting posterior ischemia of a heart comprising:

positioning a sensing electrode adjacent a posterior surface of the person's heart;

stressing the heart;

detecting electrical signals from the electrode that have been generated in response to stressing the heart;

processing the detected signals;

automatically measuring selected regi[illegible] processed signals; and generating an indicium indicative of the presence or absence of the posterior ischemia.

17. A method as in claim 16 including in the stressing step:

positioning at least one stressing electrode adjacent the posterior surface of the heart.

18. A method as in claim 17 including:

providing a selected electrical signal to the stressing electrode thereby stressing the heart in response thereto.

19. A method as in claim 16 including:

filtering the detected electrical signals prior to processing same.

20. A method as in claim 16 with said measuring step including measuring selected portions of the processed signals corresponding to an ST segment.

21. A method as in claim 20 with said measuring step including:

locating a first region of the processed signal;

locating second and third regions, displaced from the first region;

determining the corresponding values of the processed signal at the second and third regions; and comparing the corresponding valves.

22. A method as in claim 21 with said first region corresponding to a local maximum of the processed signal.

23. A method as in claim 22 with the processed signal corresponding to the R wave from the person's heart and the local maximum corresponding to the R pulse maximum.

24. A method as in claim 22 including locating second and third regions displaced in time on the order of 60 milli-seconds and 80 milli-seconds from the local maximum.

25. A method as in claim 20 including forming a difference between selected measured valves.

26. A method of detecting posterior ischemia of a heart comprising:

positioning a multi-element electrode adjacent a posterior surface of the heart;

supplying a selected heart stressing electrical signal to at least selected elements of the electrode;

suppressing artifacts generated by the stressing electrical signal;

detecting stress generated electrical signals from at least one selected element of the electrode;

processing the detected signals;

automatically measuring selected regions of the processed signals; and generating an indicium indicative of the presence or absence of the posterior ischemia.

27. A method as in claim 26 with said processing step including analog filtering of the detected signals.

28. A method a sin claim 26 with said processing step including digital filtering of the detected signals.

29. A method as in claim 28 including means for detecting a local maximum of said processed signals.

30. A method as in claim 29 including digital means for determining values of said processed signals a selected interval prior to said local maximum and a selected interval subsequent to said local maximum.

31. A method as in claim 30 including processing a plurality of values of the processed signals.

32. A method as in claim 30 including determining a plurality of slopes of processed signals.

33. A method as in claim 26 with the processing step including analog filtering of the detected signals followed by digital filtering thereof.

34. A method as in claim 33 with the digital filtering including inverse filtering of the analog filtered signal.

35. An apparatus for automatically detecting posterior ischemia in the heart of a person comprising:

multi-element electrode means, positionable in the person's esophagus, for receiving and transmitting electrical signals;

means, coupled to said electrode means, for supplying selected heart stressing electrical signals to selected elements of said electrode means;

means, coupled to said processing means, for blocking selected electrical signals induced by said heart stressing electrical signals;

means, coupled to said electrode means, for detecting stress generated electrical signals from at least one selected element of said electrode means, concurrent with said stressing;

means for processing the detected signals and generating processed signals corresponding thereto;

means for automatically measuring selected regions of the processed signals; and means for generating an indicium indicative of the presence or absence of the posterior ischemia.

36. An apparatus as in claim 35 including means for filtering said stress generated electrical signals.

37. An apparatus as in claim 36 with said filtering means including an analog filter.

38. An apparatus as in claim 36 with said filtering means including a digital filter.

39. An apparatus as in claim 36 with said filtering means including an analog filter followed by an inverse digital filter.

40. An apparatus as in claim 35 with said processing means including stored program computing means.

41. A method of detecting a selected heart condition using esophageal pacing comprising:

supplying electrical pacing signals from an esophageal site adjacent a posterior surface of the heart;

sensing heart generated, pacing related, electrical signals irrespective of any stressing induced artifacts;

simultaneously recording the pacing signals exclusive of any induced artifacts; and automatically analyzing the recorded pacing signals;

an analysis system for analyzing said recorded signals.

42. An apparatus for detection of a selected posterior heart condition from an esophageal site comprising:

an apparatus, positionable in the esophagus, for generating pacing electrical signals, said apparatus including a conductor for detecting pacing induced, heart generated electrical signals;

a suppression circuit, coupled to said apparatus, for suppressing electrical artifacts induced by said pacing signals;

a recording system for recording said pacing induced signals while generating said pacing signals; and an analysis system for analyzing said recorded signals.

* * * * *

UNITED STATES PATENT AND TRADEMARK OFFICE

CERTIFICATE OF CORRECTION

PATENT NO. : 5,010,888

DATED : April 30, 1991

INVENTOR(S) : Hossein Jadvar, et al.

It is certified that error appears in the above-identified patent and that said Letters Patent is hereby corrected as shown below:

Col. 14, line 10, "he" should be --the--.

Col. 77, line 22, "a sin" should be --as in--.

Col. 78, line 32, after "signals" delete "," and insert --.--.

Col. 78, lines 33&34 delete "an analysis system for analyzing said recorded signals".

Signed and Sealed this

Twentieth Day of April, 1993

*Attest:*

MICHAEL K. KIRK

*Attesting Officer*

*Acting Commissioner of Patents and Trademarks*